(12) United States Patent
Maguire et al.

(10) Patent No.: US 12,161,883 B2
(45) Date of Patent: Dec. 10, 2024

(54) RENOVASCULAR TREATMENT DEVICE, SYSTEM, AND METHOD FOR RADIOSURGICALLY ALLEVIATING HYPERTENSION

(71) Applicant: Varian Medical Systems, Inc., Palo Alto, CA (US)

(72) Inventors: Patrick Maguire, Foster City, CA (US); Edward Gardner, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 920 days.

(21) Appl. No.: 17/190,810

(22) Filed: Mar. 3, 2021

(65) Prior Publication Data

US 2021/0187321 A1   Jun. 24, 2021

Related U.S. Application Data

(63) Continuation of application No. 16/272,948, filed on Feb. 11, 2019, now Pat. No. 10,974,069, which is a
(Continued)

(51) Int. Cl.
*G06T 7/00* (2017.01)
*A61N 5/10* (2006.01)
*A61B 18/00* (2006.01)

(52) U.S. Cl.
CPC ......... *A61N 5/1039* (2013.01); *A61N 5/1042* (2013.01); *A61N 5/1065* (2013.01);
(Continued)

(58) Field of Classification Search
CPC .. A61N 5/1039; A61N 5/1042; A61N 5/1065; A61N 5/1083; A61N 5/1084;
(Continued)

(56) References Cited

U.S. PATENT DOCUMENTS 6,432,067 B1   8/2002   Martin et al.
6,516,211 B1   2/2003   Acker et al.
(Continued)

FOREIGN PATENT DOCUMENTS

WO   0219908   3/2002
WO   2009091997   7/2009
(Continued)

OTHER PUBLICATIONS

European Search Report mailed Apr. 24, 2015 for EP Patent Application No. 120782248.4.
(Continued)

*Primary Examiner* — Ming Y Hon
(74) *Attorney, Agent, or Firm* — Duane Morris LLP

(57) ABSTRACT

A radiosurgical method for treating cardiorenal disease of a patient, the method including directing radiosurgery radiation from outside the patient towards one or more target treatment regions encompassing sympathetic ganglia of the patient so as to inhibit the cardiorenal disease. In an exemplary embodiment, the method further includes acquiring three dimensional planning image data encompassing the first and second renal arteries, planning an ionizing radiation treatment of first and second target regions using the three dimensional planning image data so as to mitigate the hypertension, the first and second target regions encompassing neural tissue of or proximate to the first and second renal arteries, respectively, and remodeling the target regions by directing the planned radiation from outside the body toward the target regions.

20 Claims, 35 Drawing Sheets

Related U.S. Application Data continuation of application No. 16/014,978, filed on Jun. 21, 2018, now abandoned, which is a continuation of application No. 13/506,658, filed on May 9, 2012, now abandoned.

(60) Provisional application No. 61/483,962, filed on May 9, 2011.

(52) U.S. Cl.
CPC ......... *A61N 5/1083* (2013.01); *A61N 5/1084* (2013.01); *G06T 7/0012* (2013.01); *A61B 2018/00404* (2013.01); *A61B 2018/00434* (2013.01); *A61B 2018/00511* (2013.01); *A61N 2005/1061* (2013.01); *G06T 2207/30096* (2013.01)

(58) Field of Classification Search
CPC .......... A61N 2005/1061; G06T 7/0012; G06T 2207/30096; A61B 2018/00404; A61B 2018/00434; A61B 2018/00511
See application file for complete search history.

(56) References Cited

U.S. PATENT DOCUMENTS

| | | | |
|---|---|---|---|
| 6,805,129 | B1 | 10/2004 | Pless et al. |
| 7,617,005 | B2 | 11/2009 | Demarais et al. |
| 7,647,115 | B2 | 1/2010 | Levin et al. |
| 7,653,438 | B2 | 1/2010 | Deem et al. |
| 7,702,378 | B2 | 4/2010 | Bolan et al. |
| 10,974,069 | B2 * | 4/2021 | Maguire .............. A61N 5/1084 |
| 2006/0040390 | A1 | 2/2006 | Minor et al. |
| 2006/0058648 | A1 | 3/2006 | Meier et al. |
| 2006/0212078 | A1 | 9/2006 | Demarais et al. |
| 2006/0258933 | A1 | 11/2006 | Ellis et al. |
| 2006/0265015 | A1 | 11/2006 | Demerais et al. |
| 2008/0147111 | A1 | 6/2008 | Johnson et al. |
| 2008/0177280 | A1 | 7/2008 | Adler et al. |
| 2008/0221804 | A1 | 9/2008 | Jones et al. |
| 2008/0279897 | A1 * | 11/2008 | Xia .......................... A61P 29/00 435/375 |
| 2008/0292054 | A1 | 11/2008 | Rosengren et al. |
| 2009/0180678 | A1 * | 7/2009 | Kuduvalli .............. A61B 6/588 382/154 |
| 2010/0049030 | A1 | 2/2010 | Saunders et al. |
| 2010/0183121 | A1 * | 7/2010 | Riker ..................... G16H 70/20 378/65 |
| 2011/0107270 | A1 * | 5/2011 | Wang ..................... G16H 20/40 703/11 |
| 2011/0166407 | A1 * | 7/2011 | Sumanaweera ...... A61N 5/1077 600/1 |
| 2011/0200171 | A1 * | 8/2011 | Beetel ................... A61N 5/1042 378/65 |
| 2011/0276915 | A1 * | 11/2011 | Freire .................... G06Q 10/00 715/772 |
| 2012/0109018 | A1 * | 5/2012 | Gertner ..................... A61N 7/00 601/2 |
| 2012/0302878 | A1 * | 11/2012 | Liu ........................ A61B 5/064 600/424 |
| 2014/0316758 | A1 * | 10/2014 | Yagi ....................... A61B 5/026 703/9 |

FOREIGN PATENT DOCUMENTS

| | | |
|---|---|---|
| WO | 2011046879 | 4/2011 |
| WO | 2011088399 | 7/2011 |
| WO | 2011091069 | 7/2011 |
| WO | 2012/154219 | 11/2012 |

OTHER PUBLICATIONS

Dibona, Gerald F., "Sympathetic nervous system and the kidney in hypertension", Current Opinion In Nephrology and Hypertension, 2002, 11(2), pp. 197-200.

Krum, Henry, et al., "Catherter-based renal sympathetic denervation for resistant hypertension: a multicentre safety and proof-of-principle cohort study", The Lancet, 2009, 373, No. 9671, 7 pages.

International Search Report and Written Opinion of PCT Application No. PCT/US2012/000241, mailed Aug. 31, 2012, 28 pages.

\* cited by examiner

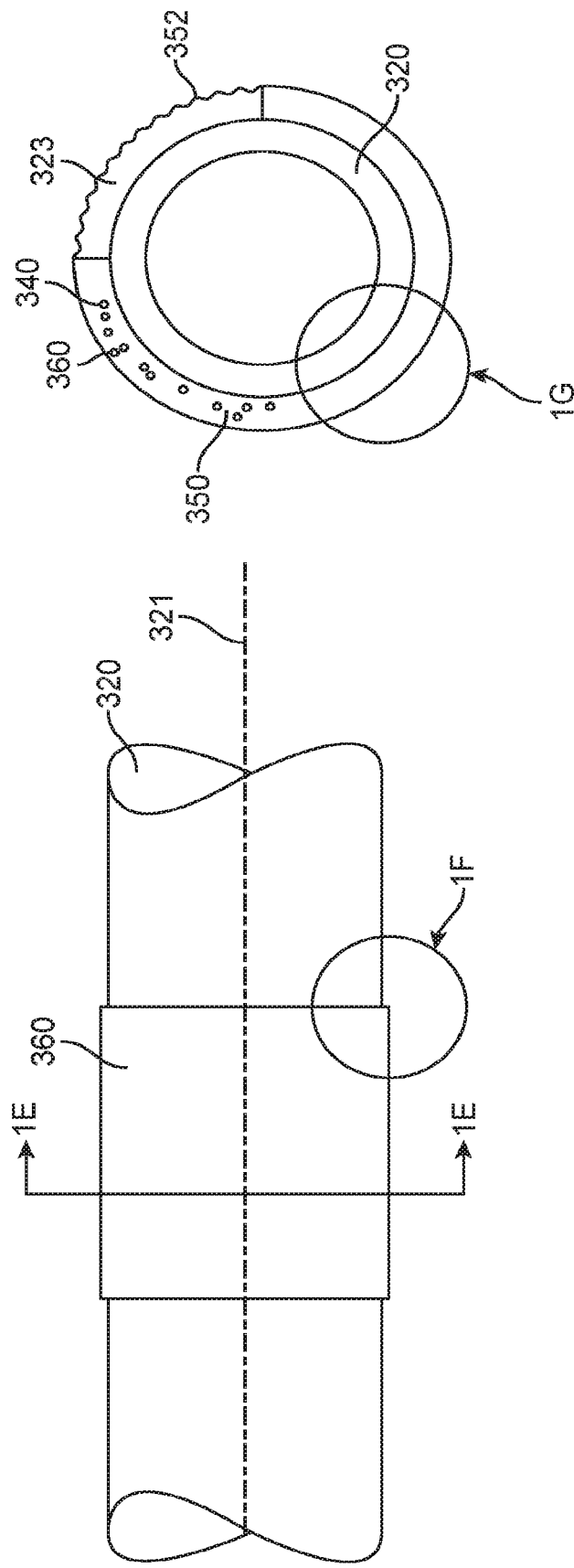

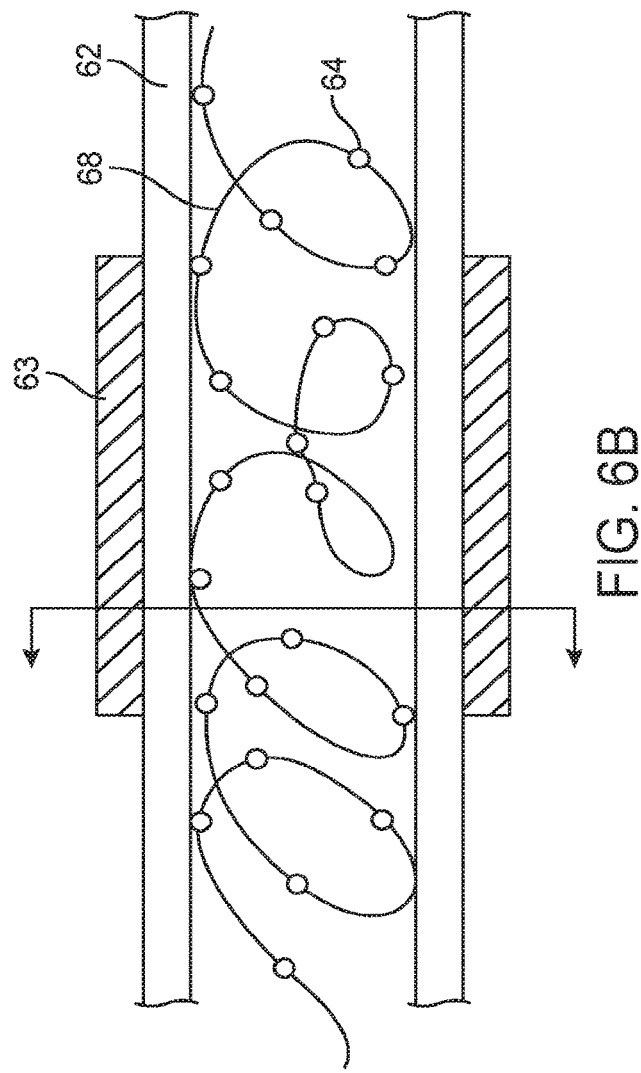
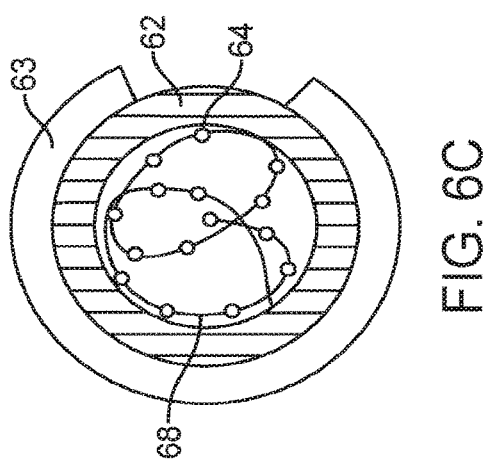
FIG. 6B
FIG. 6C

Treatment Plan Registered To Passive Fiducials

RENOVASCULAR TREATMENT DEVICE, SYSTEM, AND METHOD FOR RADIOSURGICALLY ALLEVIATING HYPERTENSION

CROSS REFERENCE TO RELATED APPLICATION DATA

The present application is a continuation of U.S. Non-Provisional application Ser. No. 16/272,948, filed Feb. 11, 2019, which is a continuation of U.S. Non-Provisional application Ser. No. 16/014,978, filed Jun. 21, 2018, which is a continuation of U.S. Non-Provisional application Ser. No. 13/506,658, filed May 9, 2012, which claims the benefit of U.S. Provisional Application No. 61/483,962 filed May 9, 2011. The full disclosures of which are incorporated herein by reference in their entirety for all purposes.

BACKGROUND OF THE INVENTION

The present invention generally provides improved devices, systems, and methods for treatment of a patient. Exemplary embodiments provide radiosurgical treatment of tissues, including nerves, in a patient body, often to treat a renovascular disease and/or to treat heart failure. Exemplary embodiments may deposit a sufficient ionizing radiation dose at a target region of the renovascular system in general, and renal nerves located proximate to the renal arteries in particular, so as to treat hypertension of the patient body. Along with allowing treatment of tissues which may move at a relatively rapid pace, embodiments of the invention may accommodate significant deformation or relative repositioning of regions of the renovascular system without subjecting the patient to unnecessary long-term trauma or inconvenience, and without unnecessarily constraining the time available for radiosurgical treatment planning.

Kidneys may play a role in the development and maintenance of hypertension. In particular, there is a link between nerves surrounding the renal arteries and hypertension. Particularly, hyperactivity of these nerves is associated with hypertension and, therefore, progression to chronic kidney disease and heart failure. Nephrectomy in patients with end-stage renal disease indicate that renal denervation may be a therapy to treat renovascular hypertension. This may lead to a reduction in the blood pressure of the patient and total systemic resistance. More particularly, denervation may be an effective way to reduce sympathetic outflow to the kidneys, increase urine output (naturiesis and diuresis) and thereby reducing rennin disease without adversely affecting other functions of the kidneys (e.g., glomerular filtration rate and/or renal blood flow. The kidneys and/or the renal nerves may also play a role in other disease states, including congestive heart failure secondary to hypertension and the like, so that renal denervation may be included in other therapies as well.

Ablating the origin of the renal nerves in the sympathetic ganglia has historically been considered very difficult. Pharmacologic assault on nerve functions is associated with systemic complications. The sympathetic renal nerves arborize throughout the walls of the renal arteries, and frustrate access thereto.

Tumors and other targets in the head, spine, abdomen, and lungs have been successfully treated using radiosurgery. During radiosurgery, a series of beams of ionizing radiation are often directed from outside a patient so as to converge at a target region, with the radiation beams often comprising MeV X-ray beams fired from different positions and orientations. The beams can be directed through intermediate tissue toward the target tissue so as to alter the biology of a tumor. The beam trajectories help limit the radiation exposure to the intermediate and other collateral tissues, while the cumulative radiation dose at the target can treat the tumor. The CyberKnife™ radiosurgical system (Accuray Inc.) and the Trilogy™ radiosurgical system (Varian Medical Systems) are two known radiosurgical treatment systems.

Modern radiosurgical systems incorporate imaging into the treatment system so as to verify the position of the target tissue and adjust to minor patient movements. Some systems also have an ability to treat tissues that move during respiration, and this has significantly broadened the number of patients that can benefit from radiosurgery. Unfortunately, some radiosurgical therapies, and particularly those which seek to target and track moving tissues using x-ray imaging, fluoroscopy, or other remote imaging modalities, may subject collateral tissues to significant imaging-related radiation and associated injury.

In light of the above, the present inventors have determined that it is desirable to provide improved devices, systems, and methods for treating hypertension utilizing radiotherapy. It would be particularly beneficial if these improvements were compatible with (and could be implemented by modification of) existing radiosurgical systems, ideally without significantly increasing the exposure of patients to incidental imaging radiation, without increasing the system costs so much as to make these treatments unavailable to many patients, without unnecessarily degrading the accuracy of the treatments, and/or without causing unnecessary collateral damage to the healthy tissues of the patient.

BRIEF SUMMARY OF THE INVENTION

The present invention generally provides improved devices, systems, and methods for treating cardiorenal disease. An exemplary method of treating a cardiorenal disease according to the present invention includes directing radiosurgery radiation from outside a patient towards one or more target treatment regions encompassing sympathetic ganglia of the patient so as to inhibit the cardiorenal disease. More specifically, an exemplary method includes a method for treating hypertension through renal denervation, including directing ionizing radiation onto renal nerves to destroy at least some of the renal nerves.

Embodiments detailed herein include deices, systems and method for renal denervation of one or both renal arteries (unilateral treatment and bilateral treatment, respectively, at one session and/or sequentially). It shall be understood that reference to the singular, as in a renal artery, renal nerves about a renal artery, kidney, etc., encompasses both the singular and plural (e.g., renal arteries, renal nerves about a plurality of renal arteries, a plurality of kidneys), and visa-versa. It is further to be understood that while embodiments may be described herein with reference to renal nerves, the teachings herein and variations thereof are also applicable to the renal ganglia and/or the aortic-reanl ganglia in general. Indeed, the teachings herein and variations thereof are applicable to a wide variety of devices, systems and/or methods that utilize ionizing radiation to partially or completely block neurological communication between one or both kidneys of a patient and a patient's central nervous system, thereby reducing hypertension or the like, including robotic radiosurgical systems, gantry-type radiosurgical systems, and the like.

The renal nerves, owing to their position vis-à-vis the renal arteries, may correspond to moving tissue of a patient, both as a result of respiration of the patient, the pulsation of the aorta and renal artery, and the heartbeat of the patient. With respect to the latter, the temporal rise and fall of blood pressure of the heartbeat cycle may cause the outer diameter of the renal arteries to expand and contract by an amount that is sufficient to move the renal nerves by an amount which may affect the treatment. Embodiments of the invention allow improved radiosurgical treatments of tissues of the renovascular system, often enhancing the capabilities of existing radiosurgical systems for targeting what in at least some instances may be relatively rapidly moving tissues (renal nerves) so as to mitigate hypertension. Treatment of renal nerves may benefit from an implanted position surrogate for identification of the location of the target tissue, with the surrogate optionally comprising a fiducial marker positioned in or near the renal arteries and/or the kidneys using catheterization techniques or direct transcutaneous routes. Novel catheters and/or delivery structures having active fiducials may limit the need for X-rays (and thereby minimize collateral imaging radiation exposure). Enhanced planning and tracking techniques may also be employed, with the radiosurgical renovascular system treatments described herein generally being compatible with many components of existing radiosurgical treatment systems.

According to a first aspect of the present invention, there is a radiosurgical method for treating a patient body having a renovascular system including a first and second renal arteries, the patient having hypertension and/or congestive heart failure. The method comprises acquiring three dimensional planning image data encompassing the first and second renal arteries, planning an ionizing radiation treatment of first and second target regions using the three dimensional planning image data so as to mitigate the hypertension, the first and second target regions encompassing neural tissue of or proximate to the first and second renal arteries, respectively and remodeling the target regions by directing the planned radiation from outside the body toward the target regions. In some embodiments, the ionizing radiation includes electromagnetic waves that ionize atoms or molecules within the body of the patient. Ionizing radiation may include x-rays, gamma rays, photons, protons and/or high-frequency ultraviolet radiation. In other embodiments, the ionizing radiation may include alpha particles, beta particles and neutrons.

When treating hypertension, for example, an appropriate lesion pattern may be identified with the help of a renovascular specialist, who may work with a radiosurgical specialist (such as a radiologist, a radiation or medical physicist, and/or the like) so as to identify the target region in the renovascular system suitable for alleviating the hypertension, the radiation dose gradients so as to avoid collateral damage to sensitive structures, and other details of the treatment plan. Other medical specialists may be consulted for identifying target regions of the heart for implanting of the surrogates, and the like. Typically, the planning of the treatment will comprise defining an estimated lesion of the renovascular system based on the planned radiation, ideally allowing a graphical representation of the estimated lesion to be reviewed as part of the process.

In many embodiments, implanting of the surrogates will comprise advancing at least one elongate flexible body through a blood vessel. The surrogate may be coupled to tissue so that the surrogate exhibits heartbeat- and/or respiratory-induced movement. The implanted surrogate may comprise a non-colinear set of discrete fiducial markers so that a three-dimensional offset orientation between the surrogate and the target area can be determined from an image of the fiducial markers. In some embodiments, implanting of the surrogate may comprise screwing a helical structure of the elongate body into a soft, contractile tissue of the heart. Implanting of the surrogate may also include expanding an expandable body with a lumen or cavity bordered by the tissue, with the expandable body optionally comprising an inflatable balloon, a temporary stent-like structure, or the like, which can be safely and reversibly expanded within a vessel so as to engage the surrounding tissue. In exemplary embodiments, implanting the surrogate may comprise fixing an active three-dimensional position indicator to the tissue, with the position indicator transmitting a position indicating signal that can be used to register a location of the implanted surrogate with the planning image data. In many embodiments, the fiducial(s) will be implanted prior to acquiring planning image data. In other embodiments, an image taken after implanting the surrogate may facilitate registration. For example, when the position indicating signal indicates an offset between the surrogate and a position sensor (or transmitter) disposed outside the body, the position indicating signal can be calibrated using post-implant image data that encompasses the position sensor. In one exemplary embodiment, the image data used for calibrating the position indicating signal comprises post-planning calibration image data, and a calibration position sensing signal is generated while a catheter tip engages a heart tissue. A positional relationship between the sensor and the body is maintained during acquisition of the calibration image data and the generation of the position sensing signal. More generally, the position indicator typically comprises a sensor or signal generator used within ultrasound or electromagnetic position indicating systems. The target region can be treated by directing the planned radiation using a position indicating signal from the position indicator between intermittent tracking verification images. Hence, position surrogates employing such active fiducial systems may limit the need for imaging X-rays (and thereby minimize collateral imaging radiation exposure).

In some embodiments, a fiducial may be placed in soft tissue or bone, optionally in or near the renal nerve. Such a fiducial may be used with spinal tracking for target localization. This fiducial may comprise a temporary wire placed under fluoroscopic guidance, with the wire remaining in place only during CT scanning and the ablation procedure, then being removed. Optional position surrogate structures may also comprise one or more bioresorbable fiducial in or around the vicinity of the renal nerve that could be used for tracking and target localization. In some embodiments the fiducials may be introduced and affixed via peptides, chemicals, proteins (e.g. syaptophysin), antibodies, or even inert conjugates that can carry or be bound to materials that present a high contrast suitable for imaging. Such a fiducial material support structure may bind to a target material, tissue, or moiety in or near the target region, with the imagable material optionally comprising gold particles or nanoparticles other heavy metal with a sufficiently high z number, polymer beads including such materials, and/or the like that can be used for tracking and localization.

The planning image data may comprise computed tomography (CT) data, magnetic resonance imaging (MRI), ultrasound (US), Positron Emission Tomography (PET), Single Positron Emmision Computed Tomography (SPECT), or the like.

A variety of approaches may be used to align a radiation treatment source with the implanted fiducials. For example, alignment image data of the surrogate may be acquired, particularly where the target region is not easily visible. The surrogate images can then be brought into a desired position and orientation by movement of a patient support. Alternative alignment approaches may include providing appropriate offsets for a radiation source supporting robot or the like.

In some embodiments, a heartbeat cycle from the body will be monitored while acquiring the planning image. A time series of three-dimensional image datasets may be acquired, with the datasets distributed throughout the heartbeat cycle so as to indicate renal artery movement with the heartbeat cycle. The planning of the treatment may include identifying radiation sensitive collateral tissues and determining a series of radiation beams suitable for providing a desired radiation dose in the target region without excessively irradiating the collateral tissue, such as the tissue forming the walls of the renal arteries. The remodeling of the target region may be performed by monitoring the heartbeat cycle of the body, and tracking at least a portion of the movement of the tissue in response to the monitored heartbeat cycle and while directing the radiation to the target region. The tracking may use the time series of datasets.

The implanting of the surrogate will often comprise advancing at least one elongate flexible body through a blood vessel and coupling the surrogate to the renal arteries so that the surrogate moves with the heartbeat cycle and respiratory cycle. A time average offset between the surrogate and the target region may be determined using the time series of image datasets. Tracking of the target region may be performed by determining a position of the surrogate, monitoring the heartbeat cycle of the body, and directing the radiation beam to the target region using the monitored heartbeat and respiratory cycles, the determined position of the surrogate, and the time average offset. Hence, deformation of the renal arteries between the surrogate and the target region need not necessarily be tracked by the system.

In exemplary embodiments, the time average offset may be determined for the heart cycle (which is used to determine a renal artery cycle, as is detailed below) by identifying a series of three-dimensional offsets from the time series of image datasets. The time average offset may be applied throughout the heart cycle so that tissue deformation between the surrogate and the target region during the heartbeat cycle is untracked. The time average offset may be further determined by selecting an image dataset from among the time series of datasets. The selected dataset may correspond to a calculated average of the measured series of offsets. The selected offset need not necessarily correspond to a quiescent phase of the heart cycle, nor to the calculated time average offset itself. In other embodiments, the calculated time average of the identified series of offsets may be used directly.

In another aspect, the invention provides a treatment kit for use with a radiosurgical system to treat a patient body. The body has a renovascular system, and the body is afflicted with hypertension and/or cardiac failure. The radiosurgical system has a radiation source for transmitting a plurality of beams of ionizing radiation from outside the patient body per a plan so as to mitigate the hypertension. The radiosurgical system also has a plurality of tracking inputs for synchronizing the radiation beams with movement of a target region of the renovascular system. The kit comprises an electrode couple-able to the patient so as to transmit a heart cycle signal of the patient to a first tracking input of the radiosurgical system. An elongate flexible body of the kit has a proximal end and a distal end insertable though a blood vessel of the patient. Alternatively or in addition to this, the kit may include a percutaneous needle configured to deliver fiducials. A position surrogate may be supported by the distal end of the flexible body so as to be insertable into operational engagement with a renal artery or the renal vein such that the surrogate moves with the renal artery suitably for generating a second tracking input of the radiosurgical system. Optionally, the distal end remains in operational engagement with the renal artery so that the distal end moves with the renal artery during treatment. Alternatively, the surrogate may be retrievable deployed from the distal end and the flexible body may be removed during application of the radiation beams.

The electrode, flexible body, and surrogate will typically be contained in a package, the package often being hermetically sealed and also containing instructions for use of the kit and the like. Additional components of the kit will also typically be included in the package.

The second input of the radiosurgical system may include a remote imaging system. The surrogate may comprise a set of passive, high-contrast fiducial markers having a sufficiently non-colinear configuration when deployed for defining a three-dimensional offset between the surrogate and the target region. The set of fiducials may have a substantially linear insertion configuration, and the surrogate may alternatively comprise an active ultrasound or electromagnetic component. The active surrogate may be included within an ultrasound or electromagnetic system that provides a signal to the second input so as to facilitate tracking of a position of the surrogate (and hence the target region). In many embodiments, a fixation surface may be provided for affixing the distal end of the elongate body to a tissue of the heart, renal artery or vein. The fixation surface may be defined by a radially expandable body, a vacuum seal body, or a helical fixation screw. In an alternative embodiment, passive surrogates are used. Such passive surrogates may be in the form of gold seeds or other substantially non-toxic seeds or other configurations, with respect to the dosages used in the methods herein, with an electron density visible on CT and/or guidance imaging.

Many embodiments of the treatment kit may include a body surface marker affixable to an exposed surface of the patient body so as to facilitate imaging of a respiration movement of the body. For example, light emitting diodes (LEDs) may be mounted to a torso of the patient. The LEDs may be imaged by a standard video camera so as to monitor respiration using standard image processing techniques.

In many embodiments, the electrode may be included in a set of electrocardiogram (EKG) electrodes. An adhesive patch suitable for affixing an ultrasound imaging transducer to a skin of the patient may also be included with the kit. Components for accessing and implanting the surrogate may also be included. For example, an introducer sheath having a proximal end affixable to skin of the patient during the radiation treatments, a distal end insertable into the patient and a lumen therebetween may be provided. The lumen may sealingly receive the elongate body, typically with a valve member of the introducer sheath providing the sealing. Additional ports or channels can be provided so that multiple surrogate-supporting catheters can be positioned simultaneously. In exemplary embodiments, the kit may also include one or more additional components, such as a guidewire, imaging contrast deliverable through a lumen of the elongate body to lumens of the renal arteries, anesthetic skin cleansing solution, a locater needle, a guidewire, and/or the like.

According to another aspect of the present invention, there is a radiosurgical system for treating a patient body with a renal artery and hypertension. The system comprises an image capture device for acquiring three dimensional planning image data from the renal artery and/or a location proximate the renal artery, a radiation source for transmitting a plurality of beams of ionizing radiation from outside the body, and a processor system configured to direct the ionizing radiation beams toward a target region of the renal artery and/or a target region at the location proximate the renal artery such that the radiation beams remodel the target region and the hypertension is mitigated.

In some embodiments, a position surrogate may be positioned and/or implanted from within an inferior vena cava (IVC) of the body prior to acquiring of the planning image data. The IVC position surrogate may be temporary, but will often remain implanted at least throughout planning and radiation delivery (optionally being permanent). Advantageously, an IVC surrogate may comprise a bioresorbable or biodegradable structure. Any inadvertent emboli associated with an IVC position surrogate may be relatively safely directed to the pulmonary vasculature by the bloodflow, and access to the IVC for implantation of prosthetic structures is well established with good patient safety. Surprisingly, in many of the embodiments described herein (including those employing an IVC position surrogate), no position surrogate may be implanted within at least the first renal artery, often within either of the renal arteries. This lack of a surrogate within the renal artery may help avoid challenges of accessing the renal arteries, and perhaps more importantly, may completely avoid potential implant induced-occlusive response of the tissues of the renal arteries (which could otherwise induce associated increase in blood pressure and thereby potential decrease or even overwhelm the hypertension alleviation available via denervation).

In many embodiment, a breathing cycle from the body will be monitored while acquiring the planning image data. The breathing cycle may also be monitored while directing the planned radiation to the target regions. The directing of the planned radiation may be controlled in response to the monitored breathing cycle. For example, the planned radiation may be gated to the breathing (so that radiation is directed only during a portion of the breathing cycle during which the target is in a desired area), and/or by tracking the breathing-induced movement of the target(s) (optionally using modified systems included on commercially available radiosurgical systems for tracking tumor target movement associated with breathing). Advantageously, the directing of the planned radiation may be performed in many of the embodiments described herein (and surprisingly, even including those that employ tracking for breathing-induced motion) without tracking movement of at least the first renal artery in response to a heartbeat cycle of the body (particularly without tracking heartbeat-induced movement of the left renal artery), and often without tracking such movement of both arteries.

The processor of the systems described herein can be configured to control the direction of the radiation to account for breathing-induced movement of the renal artery and/or the location proximate the renal artery. The processor may be configured to control the direction of the radiation without tracking heartbeat-induced movement of the renal artery and/or the location proximate the renal artery. The processor can be configured to control the direction of the radiation in response to the position surrogate within the inferior vena cava and without a position surrogate disposed within the renal artery. In such embodiments, the processor may be configured to provide a margin of less than 2 mm to account for heartbeat-induced movement of the renal artery and/or the location proximate the renal artery, and may optionally be configured to provide a margin of less than 0.5 mm to account for heartbeat-induced movement of the renal artery and/or the location proximate the renal artery (for example, when treating the left artery).

As will be understood, the teachings herein are applicable to any device, system or method that utilizes ionizing radiation to partially or completely block the renal nerve plexus.

BRIEF DESCRIPTION OF THE DRAWINGS

FIGS. 1D-1G depict exemplary target treatment regions with reference to anatomical structure according to an exemplary embodiment of the present invention;

FIGS. 6A-6C show catheter-based fiducials deployed in a lumens of the renal artery so as to provide a tracking surrogate;

FIGS. 9A and 9B schematically illustrate a system and method for registering a catheter tip with a CT dataset so as to calibrate a position sensing system including an active fiducial or the like;

DETAILED DESCRIPTION OF THE INVENTION

The present invention generally provides improved systems, devices, and methods for treatment of tissue to alleviate cardiorenal disease, including hypertension, using radiosurgical systems. The embodiments of the present invention detailed herein and variations thereof may have the therapeutic effect of slowing, including halting, the progression of congestive heart failure via a non-invasive or minimally invasive (in embodiments utilizing catheters or percutaneous needles to implant surrogates, as detailed below) surgical procedure. Some or all embodiments detailed herein and variations thereof may be practiced to mitigate the conjunctive heart failure that sometimes develops following a myocardial infarction.

Figure 1:
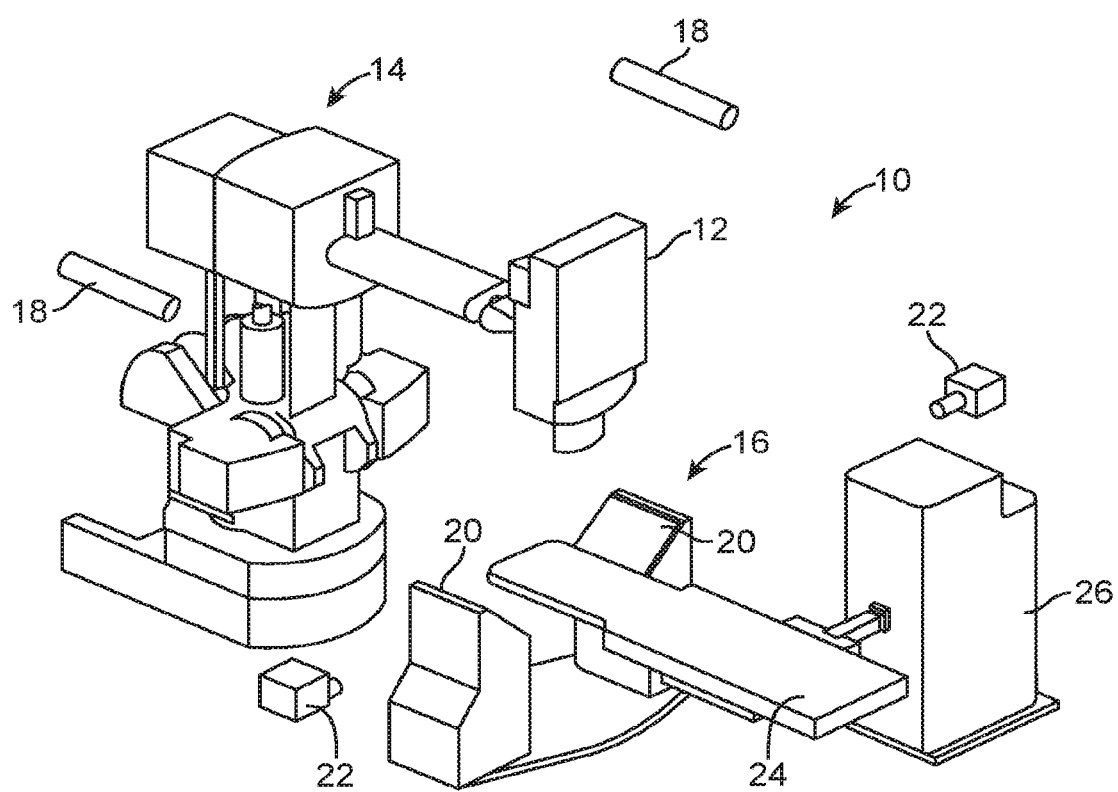
FIG. 1 is an exemplary CyberKnife™ stereotactic radiosurgery system for use in embodiments of the invention.
Figure 1A:
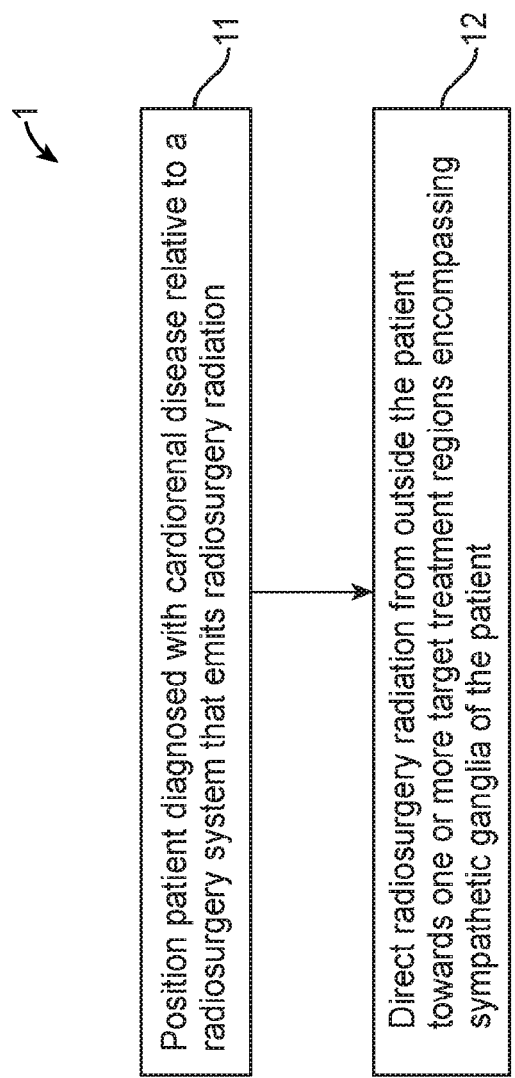
FIG. 1A schematically illustrates a method for treating a target tissue using a radiosurgical system.

FIG. 1A provides an exemplary flowchart 1 of a method for treating cardiorenal disease of a patient, such as hypertension. At step 11, a patient diagnosed with cardiorenal disease, such as hypertension, is positioned relative to a radiosurgery system such as that detailed below with respect to FIG. 1 that emits ionizing radiation. At step 12, radiosurgery radiation (ionizing radiation) is directed from outside the patient by the radiosurgery system towards one or more target treatment regions encompassing sympathetic ganglia of the patient so as to inhibit the cardiorenal disease. In an exemplary embodiment, step 12 is a renal denervation procedure where the radiation deteriorates and/or destroys at least some of the renal nerves surrounding one or both renal arteries of the patient (depending on whether the procedure encompasses a unilateral or bilateral denervation procedure), resulting in the inhibition of hypertension of the patient. More particularly, the radiation directed towards the renal nerves at least partially, including substantially and entirely, reduces the ability of a central nervous system of the patient to communicate with one or both kidneys of the patient. This has the resulting effect of reducing hypertension.

Step 12 may be considered to correspond to renal nerve modulation via radiosurgical ablation of the renal nerves. Again, as noted above, while this embodiment has been described with respect to renal nerves, this embodiment also corresponds to the radiosurgical ablation of the renal plexus and ganglion to reduce hypertension. As will be understood, the result of step 12 (i.e., the direction of the radiation to the target treatment regions encompassing the sympathetic ganglia) blocks or at least down-regulates sympathetic impulses between one or both kidneys of the patent and a central nervous system of the patient. That is, renal nerve activity in the patient is blocked or at least down-regulated. As detailed above, reducing communication between the central nervous system and the kidneys via renal denervation reduces (including eliminates) hypertension, in at least some patients. More specific features the renal denervation procedures according to some exemplary embodiments of the present invention will now be described.

Figure 1B:
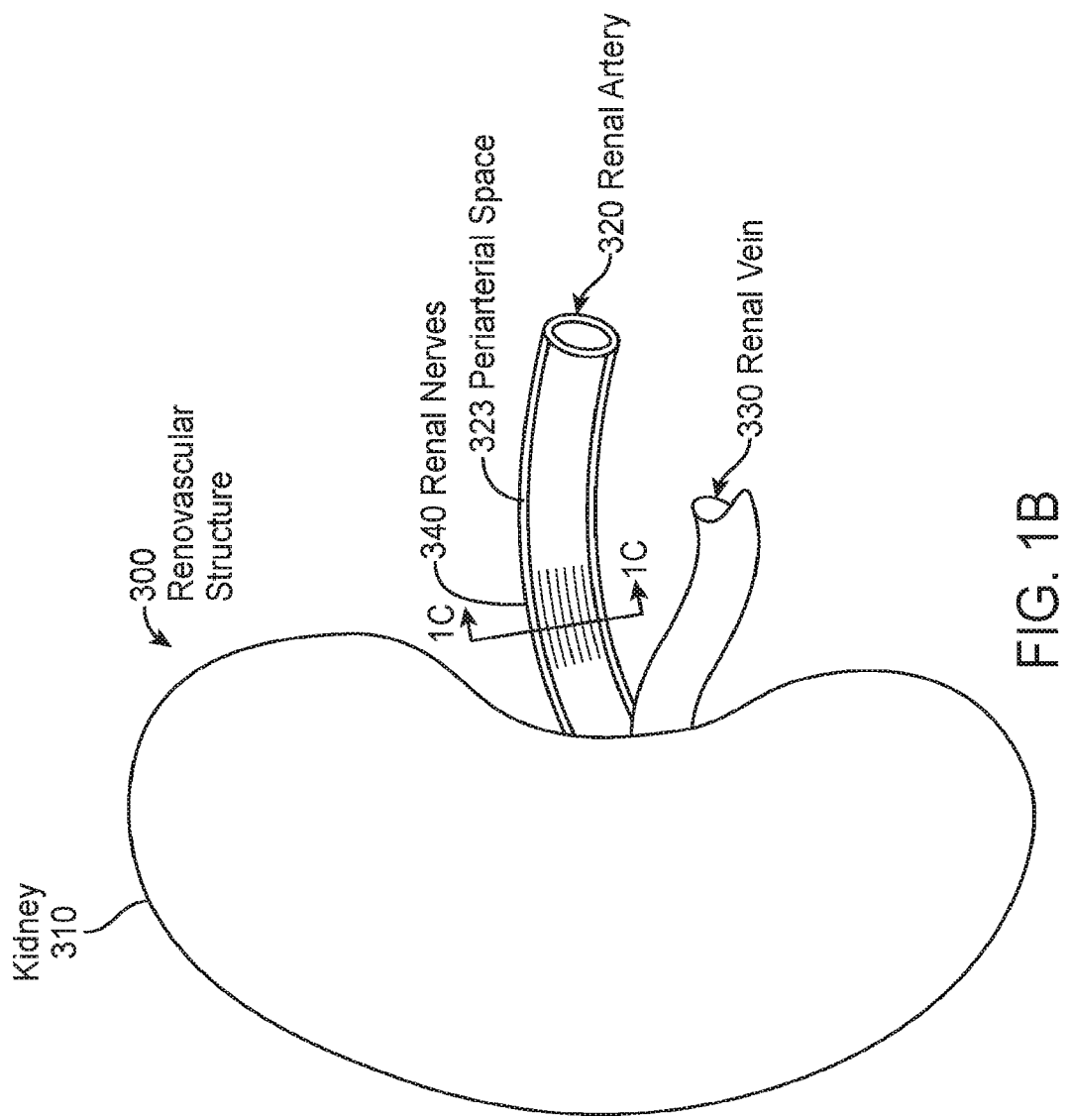
FIGS. 1B and 1C depict an exemplary renovascular structure to which embodiments of the present invention may be applicable.
Figure 1C:
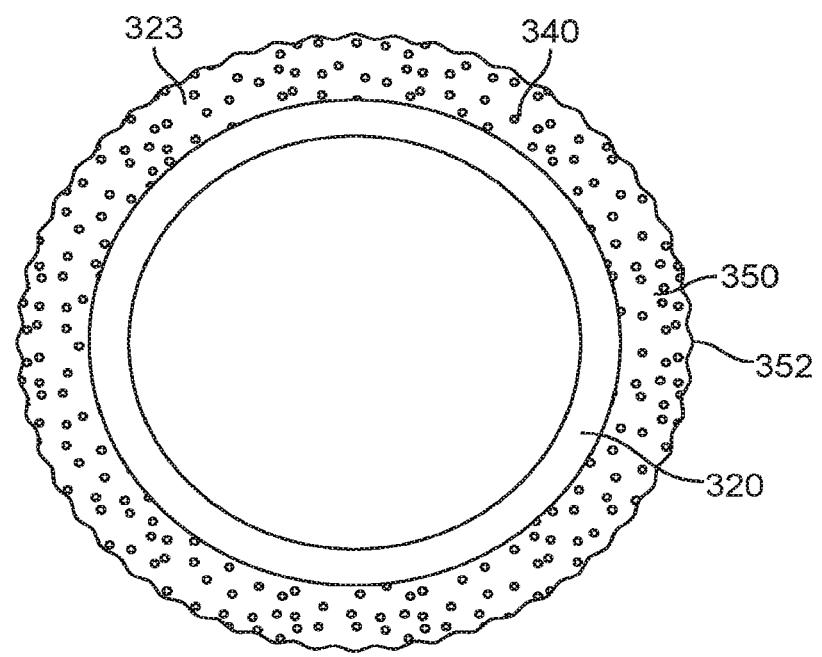
Figure 1G:
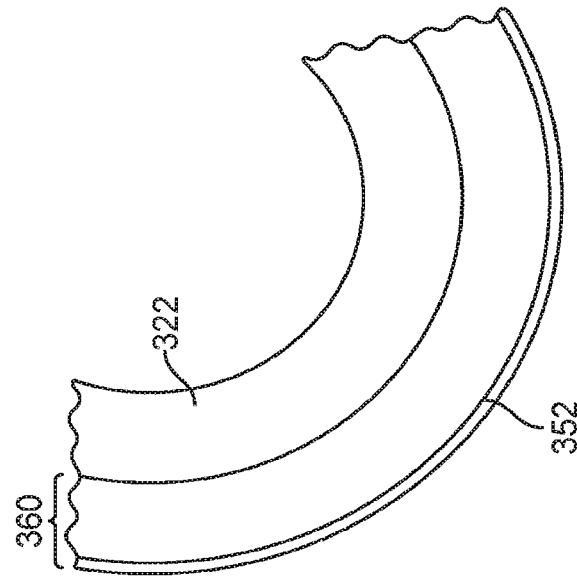
Figure 1F:
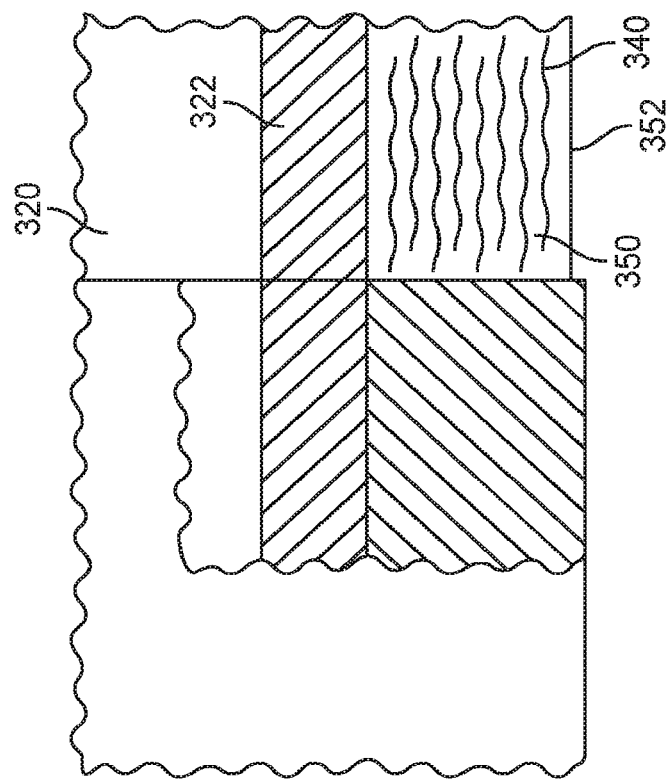

FIG. 1B provides a schematic of a portion of the renovascular structure 300 of a patient. As may be seen in FIG. 1B, the renovascular structure 300 includes kidney 310 (and, if present, the second kidney, which is not shown), renal artery 320 and renal vein 330 (again, if present, the second renal artery and second renal vein). Renal nerves 340, a portion of which are shown in FIG. 1B, are located about the renal artery 320 (and the second renal artery, if present) in the periarterial space 323 of the renal artery 320. FIG. 1C depicts a conceptual unscaled cross-sectional view of the renal artery 320 and renal nerves 340, the renal nerves being surrounded by membrane 350 located in periarterial space 323, the boundary of the membrane which is depicted, again conceptually, as 352. In an exemplary embodiment of the present invention, the target treatment regions of step 12 envelopes renal nerves 340. By envelopes renal nerves 340, it is meant that at least a portion of the renal nerves 340 is enveloped by the treatment region. Accordingly, the treatment region may be limited longitudinally, diametrically and/or laterally with respect to the renal artery 320 while enveloping renal nerves. For example, FIGS. 1D and 1E depict an exemplary three-dimensional treatment region 360 enveloping renal nerves 340. FIG. 1D is a side-view of a renal artery 320, and FIG. 1E is a cross-sectional view of FIG. 1D. FIGS. 1F and 1G depict enlarged views of portions of FIGS. 1D and 1E, respectively. In these views, any anatomical structure taken up by the treatment region is not shown. For example, FIG. 1F depicts renal nerves 340 on the right side of the figure, but the treatment region 360 eclipses those renal nerves on the left side of the figure.

Figure 1I:
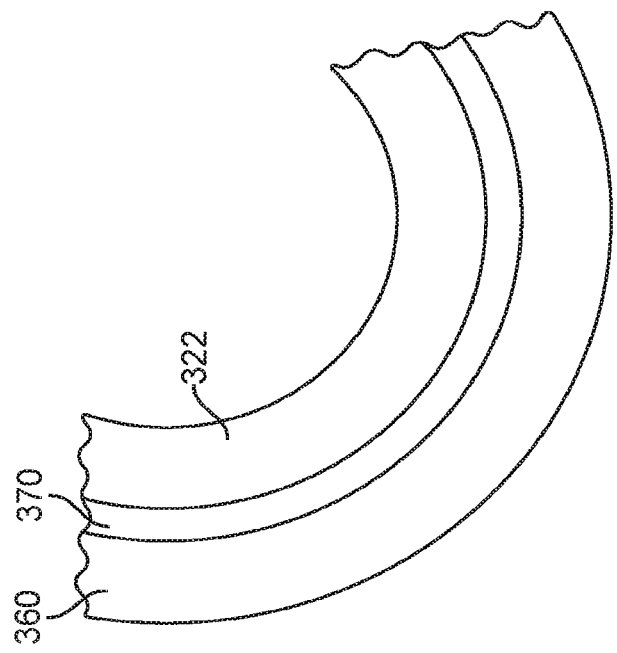
FIGS. 1H-1I depict alternate exemplary target treatment regions with reference to anatomical structure according to an exemplary embodiment of the present invention.
Figure 1H:
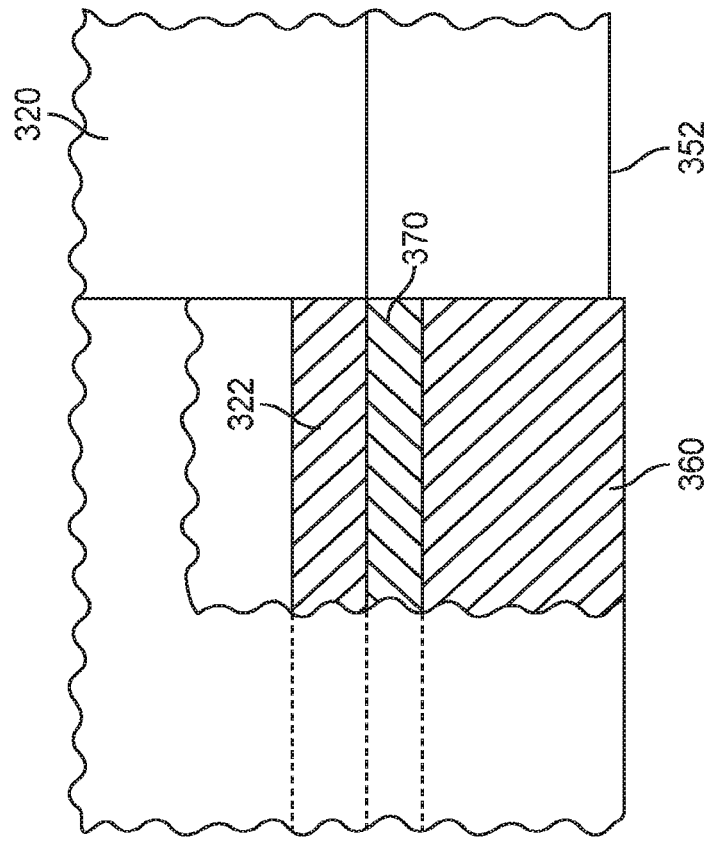
Figure 1J:
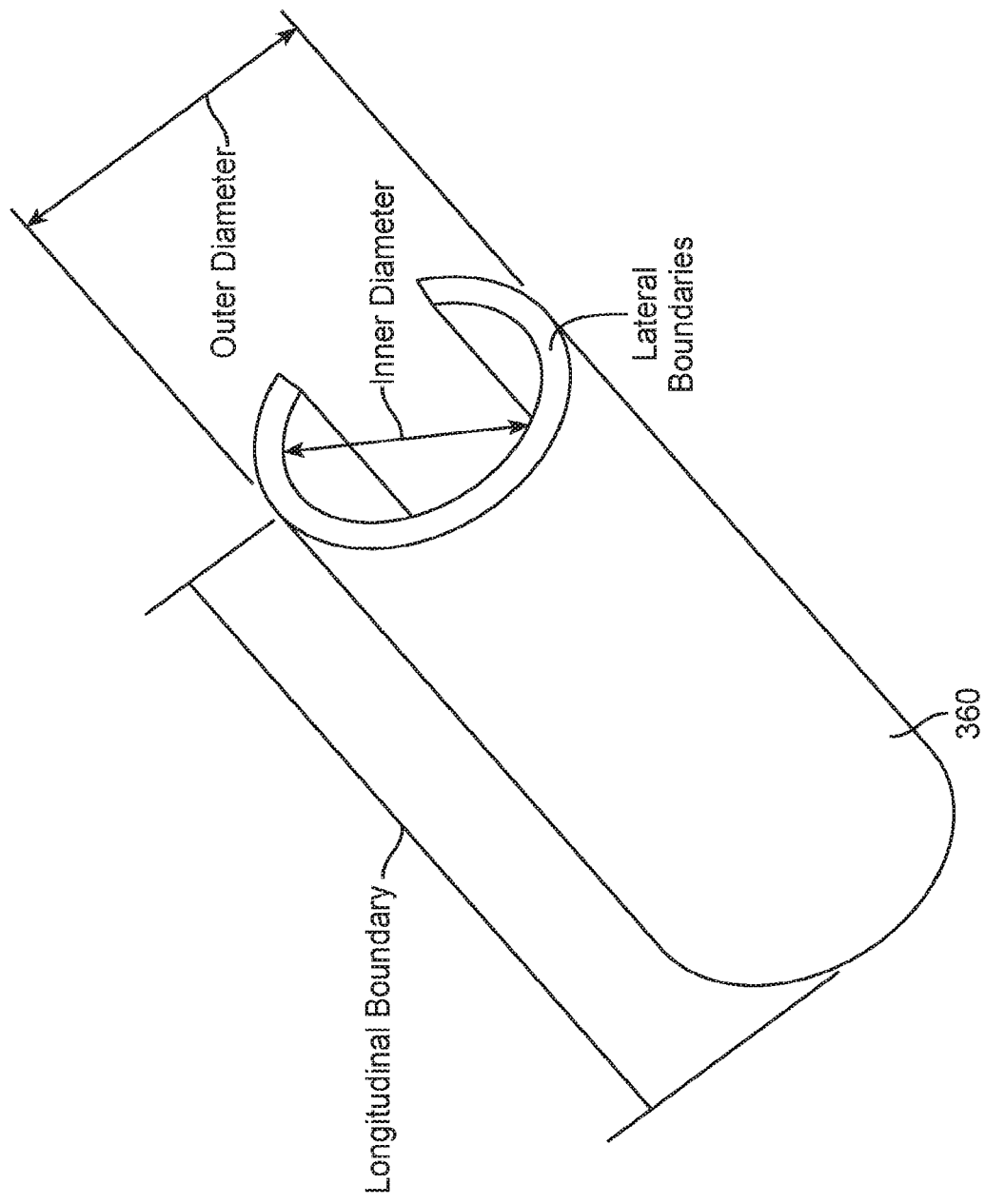
FIG. 1J depict an exemplary target treatment region without reference to anatomical structure according to an exemplary embodiment of the present invention.

As may be seen from FIGS. 1D-1G, the target treatment region 360 may be in the shape of a toroidal arc-segment, such as a generally cylindrical shape, as may be seen in the FIGS., bounded in the longitudinal direction (see FIG. 1D) and the lateral direction (see FIG. 1E). FIG. 1J depicts an isometric view of target region 360 without any anatomical structure, detailing the longitudinal boundary, the lateral boundaries, and other useful dimensions. FIGS. 1E and 1G, in view of FIG. 1J, show that the target treatment region is bounded in the lateral direction both circumferentially in that it does not completely surround the renal artery (instead forming a "C" shape, as may be seen in FIG. 1E, which depicts a cross-sectional view of the target region 360 when taken on a plane normal to the longitudinal direction 321 of the renal artery 320) and in the radial direction in that it has an inner diameter that lies at the outer diameter of the renal artery wall 322 and has an outer diameter that lies just beyond the membrane wall 352. Optionally, the target treatment region has an opening extending down the longitudinal axis of the cylinder.

It is noted that in other embodiments, the target treatment region 360 may have different longitudinal and/or lateral boundaries. FIGS. 1H and 1I correspond to FIGS. 1F and 1G, respectively, except show that the inner diameter of the treatment region 360 is located beyond the outer diameter of the renal artery wall 322. Thus, there is a space 370 separating the renal wall 322 and the treatment region 360. It is noted that in other embodiments, the inner diameter of the target treatment region 360 may be located inside the renal artery wall 322. Also, in other embodiments, the outer diameter of the target treatment region 360 may be located inside the membrane wall 352. In yet other embodiments, the target treatment region 360 surrounds the entire renal artery (i.e., it has a cross-section when taken normal to the longitudinal direction of the renal artery that is "0" shaped). In such an embodiment, the renal nerves are essentially uniformly "thinned out" within the longitudinal boundaries of the target treatment region. This is in contrast to the target treatment regions of FIGS. 1F and 1G, having the "C" shaped cross-section, where the renal nerves are destroyed within the cross-section of the "C" shape, but are left substantially unharmed outside of the cross-section of the "C" shape. Thus, the surviving renal nerves are not uniformly distributed within the longitudinal boundaries of the target treatment region. In some such embodiments where the target treatment region has an "0" shaped cross-section, the inner diameter and/or the outer diameter of the target treatment region 360 is located such that some renal nerves are not enveloped by the target treatment region, such as is the case, by way of example, with respect to the target treatment regions depicted in FIGS. 1H and 1I above. That is, some renal nerves located within the longitudinal boundaries of the target treatment region lie outside the lateral boundaries of the target treatment region. However, in other embodiments, all of the renal nerves located within the longitudinal boundaries of the target treatment region lie inside the lateral boundaries of the target treatment region.

By controlling the boundaries of the target treatment region 360 relative to the structures of the renovascular system (e.g., the renal arteries), the functionality and performance of the renal artery can be substantially maintained after the treatment for the cardiorenal disease. By way of example, the target treatment region may be controlled, relative to the renovascular structures such that the radiation directed to the renal nerves does not result in significant blockage of the renal artery. That is, even though the target treatment region envelops renal nerves, and those renal nerves are located about a renal artery of the patient, the renal artery proximate the target treatment region remains is substantially unblocked after the radiation is directed towards the target treatment regions. Alternatively or in addition to this, to the extent that radiation is delivered to the walls of the renal arteries, the dose of radiation is not sufficient to result in narrowing or stenosis of the renal arteries. In some embodiments, after completing the treatment (i.e., final completion of directing radiation to the renal nerves, after which directed radiation is sufficient to alleviate the hypertension such that no further radiation treatments are needed within at least six months, one year, eighteen months or 2 years) to maintain the alleviation of the hypertension), the inner diameter of the artery proximate the target treatment region is at least substantially the same six months after the action of directing the radiation as it was just prior to directing the radiation.

It is noted that in some embodiments of the present invention, the shapes of the target regions generally or substantially correspond to the shapes of the resulting deteriorated/destroyed renal nerves. This is because the radiosurgical system is configured to precisely control the dose level of radiation delivered to the target region such that there is a rapid and significant drop-off of the radiation dose delivered at or proximate to the boundaries of the target regions, as will be described in greater detail below.

Figure 1K:
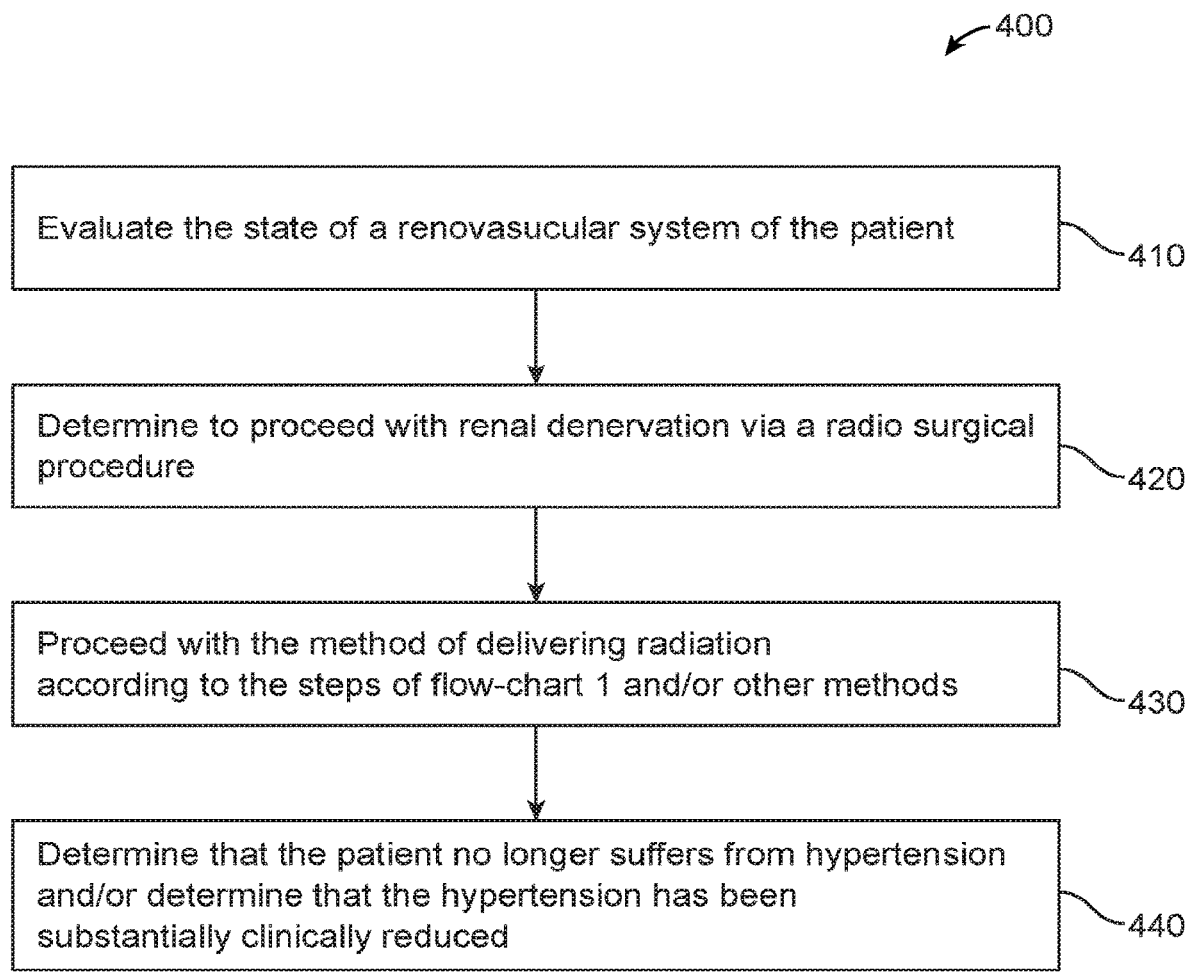
FIG. 1K schematically illustrates a method for treating a target tissue using a radiosurgical system wherein the method may utilize the method related to FIG. 1A.

FIG. 1K presents a flow-chart 400 of an expanded method according to an exemplary embodiment of the present invention, which includes the method steps of flowchart 1 detailed above. Flow-chart 400 includes step 410, which entails evaluating the state of a renovasucular system of the patient. In an exemplary embodiment, step 410 entails determining that the patient suffers from hypertension, and, optionally, also determining that the patient's renovascular system is not affected with a non-hypertension related disease in general, and a tumorous disease in particular. The determination(s) of step 410 may also include the action of evaluating at least one of a systolic or a diastolic blood pressure of the patient and determining, as a result of the evaluation, that the respective pressure correspond to a pressure indicative of hypertension. Based on the determinations and/or evaluations of step 410, a determination is made at step 420 to proceed with a renal denervation procedure including the method of delivering radiation according to the steps of flow-chart 1 and/or other methods detailed herein and variations thereof.

After step 420, the method proceeds to step 430, which entails performing steps 11 and 12 of flowchart 1 or delivering radiation via another method detailed herein. In this exemplary method, the radiation directed to the target regions in step 12 is directed in response to the determination/evaluation of step 410. After step 430, the method proceeds to step 440, which entails determining that the patient no longer suffers from hypertension and/or determining that the hypertension has been substantially clinically reduced. Step 430 may include the action of reevaluating at least one of the systolic or a diastolic blood pressure of the patient and, based on that reevaluation, making the determination about the patients hypertension depending on whether or not the respective reevaluated pressures correspond to a pressure indicative of hypertension. In an exemplary embodiment of step 440, if the reevaluated systolic or diastolic blood pressure is clinically substantially lower than the respective initially evaluated systolic or diastolic blood pressure (e.g., a reevaluated systolic blood pressure lower than the initially evaluated systolic blood pressure by about 20 mm Hg or more), a determination is made that the hypertension has been substantially sufficiently clinically reduced. In another embodiment, should it be determined that hypertension has not been sufficiently or desirably treated, and maximal radiation tolerance doses have not yet been met, then a re-ablation can be performed.

In some embodiments of the present invention, the renal denervation processes disclosed herein results in a reduction of a cardiac infarct size expansion and improvement in ventricular ejection fraction. Optionally, the methods, devices, and systems described may be used of treatment of congestive heart failure secondary to hypertension, and/or for modulation of neurohumoral chemicals that effect ion and peptide chemicals. Such treatments may be used to modulate and improve heart failure, congestive heart failure, and/or to reduce left ventricular size and/or mass.

Embodiments of the invention may be particularly well suited for treatment of moving tissues, such as tissues adjacent the real arteries, such as the renal nerves. Such embodiments may take advantage of structures and methods which have been developed for treating tumors, particularly those which are associated with treatment of tissue structures that move with respiration cycles. The cardiac cycle is typically considerably faster than the respiration cycle, and overall treatment times can be fairly lengthy for effective radiosurgical procedures on the renovascular system (typically being up to 100 minutes, depending on the treatment plan). Hence, it will often be advantageous to avoid continuous imaging of the target and adjacent tissues using fluoroscopy or the like so as to limit exposure to excessive imaging radiation. Advantageously, the invention can provide physicians and other medical professionals with adequate time for planning a proper radiosurgical course of treatment once a planning image dataset and other diagnostic measurements have been obtained.

The present invention may take advantage of many components included in or derived from known radiation delivery systems. An exemplary modified CyberKnife™ stereotactic radiosurgery system 10 is illustrated in FIG. 1. Radiosurgery system 10 includes a lightweight linear accelerator 12 mounted to a robotic arm 14. In an exemplary embodiment, the robotic arm 14 moves the linear accelerator 12 about a body of a patient during remodeling of the target regions. An image guidance system 16 includes biplane diagnostic X-ray sources 18 and image detectors 20 so as to enhance registration between robot arm 14 and the target site. As the tissues in the target region may not present a high-contrast image, image guidance system 16 may use image processing techniques to identify the location of one or more surrogate structures, with the surrogates typically including a high-contrast natural tissue structure (such as a bone or the like) or an artificial implanted fiducial marker that moves in correlation with the target tissue. Target tracking may also make use of one or more surface image cameras 22, particularly for identifying movement of the chest wall and/or the wall of the abdominal cavity corresponding to respiration. Cameras 22 may monitor light emitting diodes (LEDs) or other high-contrast fiducial markers visible on the patient's chest and/or abdomen. A patient support 24 is movably supported by an alignment arm 26 so as to facilitate bringing the patient (and treatment site) into alignment with robot arm 14. As will be understood, exemplary embodiments of the present invention include practicing the methods detailed herein using the radiosurgical system 10.

In other embodiments, the methods detailed herein may be implemented using an alternate radiosurgical system where, instead of a robotic arm 14 supporting a linear accelerator 12, a plurality of radiation sources fixed relative to the radiosurgical system may be arrayed about the body. Such an alternate radiosurgical system may still include one or more all of the features just detailed with respect to radiosurgical system 10. In an exemplary embodiment, a GammaKnife™ radiosurgical system may be used.

Figure 2:
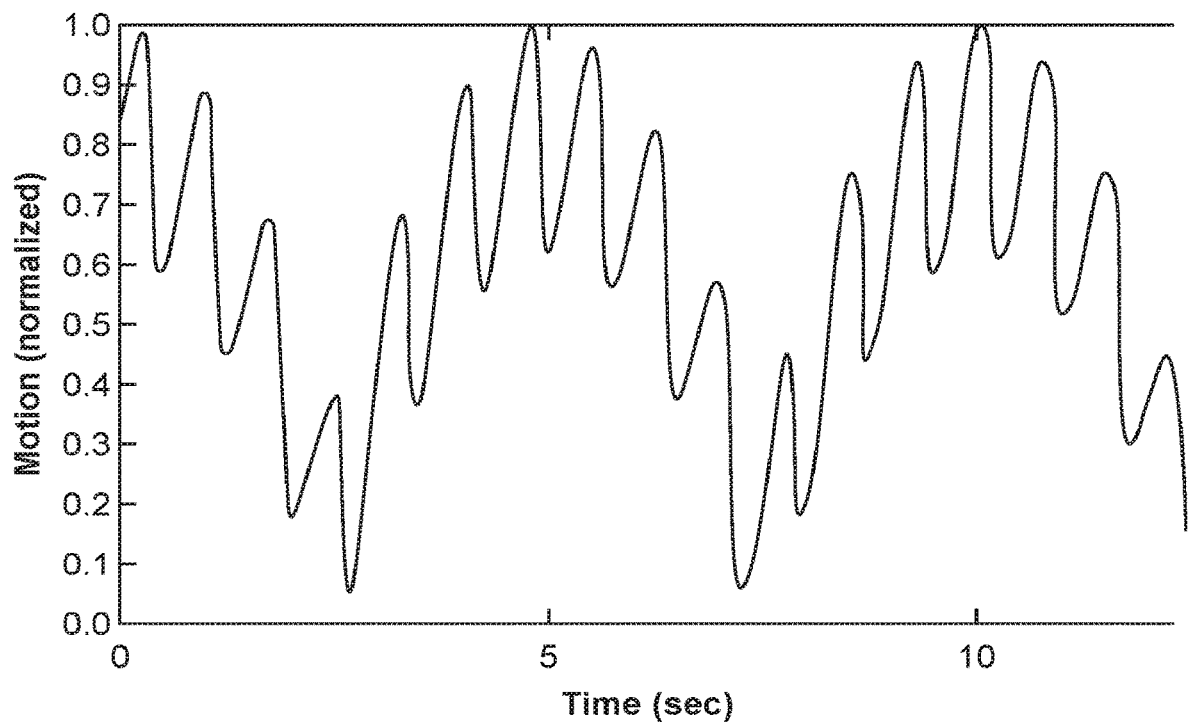
FIG. 2 is a graph showing exemplary data from the anterior/posterior motion of a point on the outer wall of a renal artery, showing movement associated with both the heart beat cycle and the respiration cycle.

FIG. 2 graphically depicts hypothetical motion of a point on a renal artery. As can be seen, the motion includes two components: a slowly varying breathing component and a more rapid cardiac component. As used herein, the cardiac component includes (i) dilation of the artery due to the increase of blood pressure and the subsequent contraction due to subsequent decrease in blood pressure of the heart cycle and (ii) motion resulting from pressure waves traveling from the outer surface of the heart and/or from tissue contiguous therewith, as a result of expansion and/or contraction of the outer surface of the heart during the heart cycle, which travel through tissue and/or fluid of the body that impinge on the artery (typically, the outside wall of the artery) and/or tissue contiguous thereto, thus causing the artery to move. Motion "i" is referred to as a "blood pressure component" of the cardiac cycle/heart cycle and motion "ii" is referred to as a "displacement component" of the cardiac cycle/heart cycle." Embodiments of the present invention may address one, some or all of these motion components. For example, robot arm 14 may move linear accelerator 12 synchronously with a target site so as to compensate both for the respiration component, and for the cardiac component of overall motion. Alternatively, synchronous movement of robot arm may track only the respiration component while disregarding the cardiac component in at least one or more degrees of freedom. In some embodiments, robot arm 14 may track the respiration component of motion with gating of linear accelerator 12 applied so as to limit the radiation beam to portions of the heartbeat cycle where the target tissues are sufficiently aligned with the robot so as to mitigate or eliminate cardiac motion-induced errors. As the significance of the different motion components in different degrees of freedom may vary, differing combinations of motion component tracking, motion component disregarding, and radiation gating may be employed. Exemplary tracking approaches are described in more detail in U.S. Patent Publication 2008/0177280 in the name of Adler et al., as published on Jul. 24, 2008 (the full disclosure of which is incorporated herein by reference.)

Figure 3:
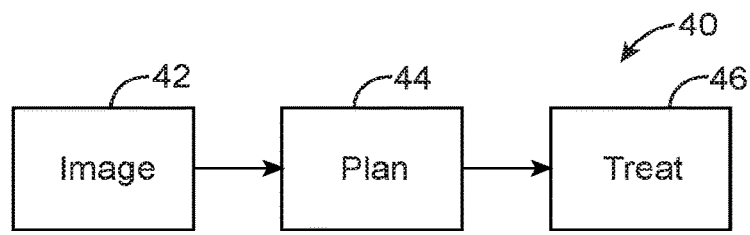
FIG. 3 schematically illustrates a method for treating a target tissue using a radiosurgical system that may utilize the methods related to FIGS. 1A and/or 1K.
Figure 4:
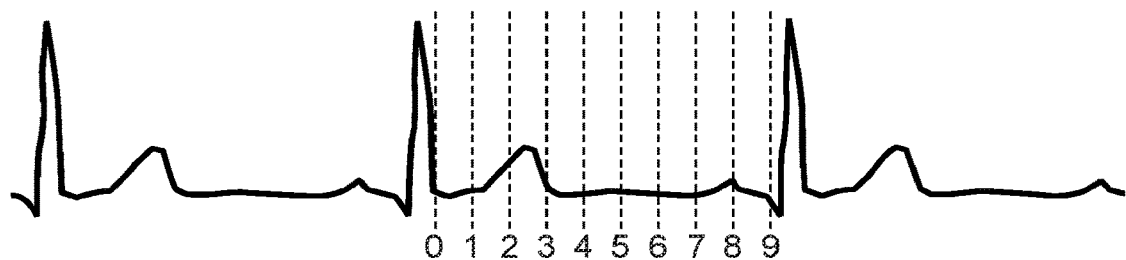
FIG. 4 is an illustration of an EKG waveform showing exemplary phases where a time sequence of CT volumes are acquired.

Referring now to FIG. 3, a relatively simple treatment flowchart 40 can represent steps used before and during radiosurgical treatment according to embodiments of the present invention. The internal tissues are imaged 42 for planning purposes, typically using a remote imaging modality such as a computed tomography (CT), magnetic resonance imaging (MRI), ultrasound imaging, X-ray imaging, PET, SPECT, optical coherence tomography, a combination of these, or other imaging modalities. With respect to radiosurgical methods for treating a patient body having a renovascular system, where the patient has hypertension, a three dimensional planning image data encompassing one or both renal arteries and/or the respective renal nerves is acquired. Note that the tissue structure which will actually be targeted for radiation remodeling (e.g., renal nerves) need not necessarily be visible in the image, so long as sufficiently contrasting surrogate structures are visible in the image data to identify the target tissue location. In an exemplary embodiment, the location of the tissue structure which will actually be targeted but not readily imaged can be sufficiently estimated with reference to structures that can be imaged and/or to the implanted surrogate. For example, the renal nerves may not be readily imaged, but their position may be estimated with reference to an imaged renal artery. The planning imaging used in many embodiments may include a time sequence of three-dimensional tissue volumes, with the time sequence typically spanning one or more movement cycles (such as a cardiac or heartbeat cycle, a respiration or breathing cycle, and/or the like). In exemplary embodiments, the image data comprises a series of CT slices through the heart so as to provide volumetric or three-dimensional image data. The time series of three-dimensional heart images may be acquired at times that are distributed throughout the heartbeat cycle, so that the image planning data effectively comprises a time series of three-dimensional image datasets providing information regarding the motion of renovascular tissues during the heartbeat. FIG. 4 shows a typical heartbeat electrocardiogram (EKG) waveform from which ten phases have been identified and for which ten associated CT volumes are acquired. In some embodiments, the target tissue may be outlined in each of the ten volumes, or the target outline may be identified in one CT volume and automatically tracked over the other CT volumes. As will be described in more detail hereinbelow, other alternatives include selecting an appropriate one of the three-dimensional image datasets from the time series, generating an average positional dataset, or the like. Regardless, acquisition of the series of three-dimensional datasets can be performed using any of a variety of commercially available CT systems.

Figure 5A:
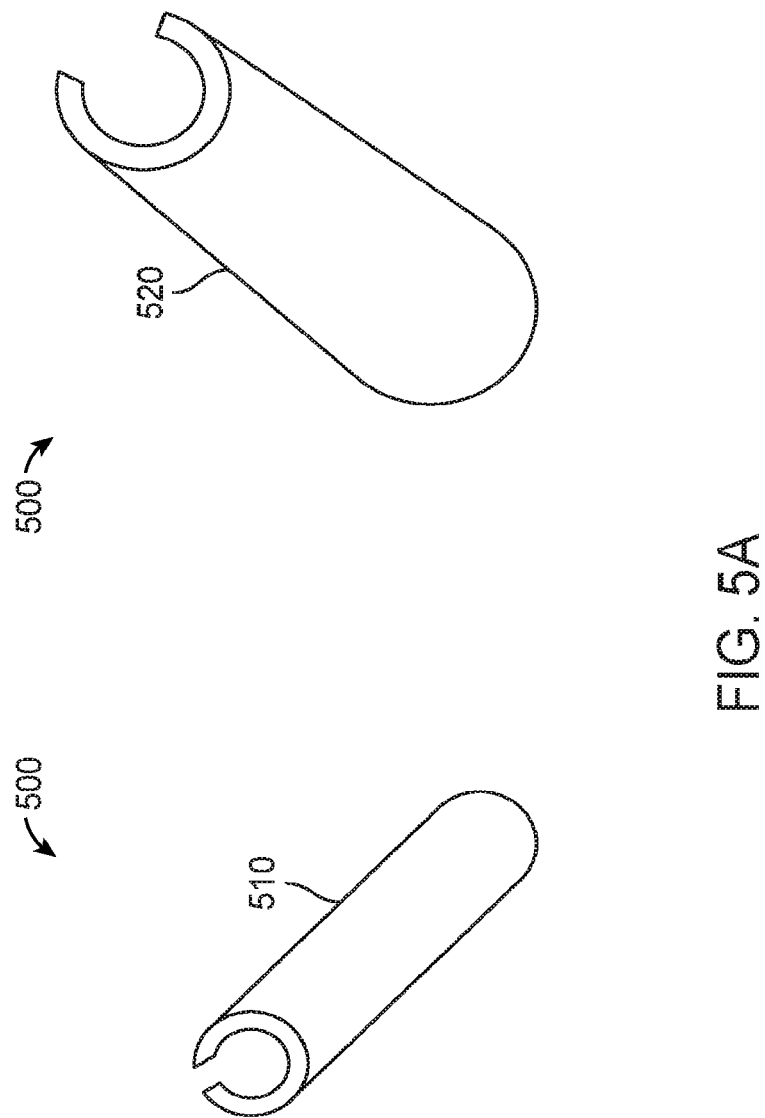
FIG. 5A depicts exemplary target treatment regions without reference to anatomical structure according to an exemplary embodiment of the present invention pertaining to a bilateral treatment for hypertension.

Referring still to FIG. 3, based on the imaging data obtained from image step 42, a plan 44 can be prepared for treatment of the tissue at the target site. The plan typically comprises a target region or regions and a series of radiation beams which intersect within the target region. The radiation dose within the target tissue should be at least sufficient to provide the desired remodeling effect. With respect to the methods of renal denervation detailed herein, the plan may entail planning an ionizing radiation treatment of a first region (in the case of a unilateral treatment) or a first and second target region (in the case of a bilateral treatment) using the three dimensional planning image data detailed above. The first and, if applicable, second target regions encompass neural tissue of or proximate to the first and second renal arteries, respectively. In the case of a bilateral treatment, the first and second target regions may comprise two spatially separated non-contiguous regions, as is depicted by way of example in FIG. 5A, which depicts a target region group 500 comprising a first target region 510 arrayed about the a first renal artery and a second target region 520 arrayed about a second renal artery. It is noted that the term target region as used herein is not limited to a region surrounding a single artery. A target region may be such that the region surrounds a majority of respective perimeters of the first and second renal arteries of the patient, the target region thus having two sections (510 and 520, respectively) separated by a space into which a therapeutic level of radiation is not directed.

Typically, the radiation dose delivered to the target regions will be sufficient to ablate renal nerves to inhibitor otherwise reduce neural communication between one or both kidneys and the central nervous system, inhibit hypertension, and/or the like. Radiation dosages outside the target tissue will in many embodiments, decrease with a relatively steep gradient so as to inhibit excessive damage to collateral tissues, with radiation dosages in specified sensitive and/or critical tissue structures often being maintained below a desired maximum threshold to avoid deleterious side effects. It is noted that in some embodiments, the target treatment regions have boundaries such that the outer diameter of the treatment region is less than the outer diameter of the renal nerves, the area between the two being an area where the radiation dose gradient substantially decreases. That is, by controlling the outer diameter of the treatment region, the gradient may be maintained within the renal nerves. As will be understood, renal denervation often entails avoiding the destruction of all of the renal nerves. Accordingly, the renal nerves located within the gradient region may be the renal nerves which are permitted to survive the renal denervation process.

Referring now to FIGS. 3 and 5, an exemplary treatment planning module and user interface allows the system user to input a desired lesion pattern with reference to a surface of a tissue. For treatment of moving tissues of the renovascular system (e.g., renal nerves arrayed about the renal arteries) so as to inhibit hypertension, a reference surface of the renal nerves may comprise the nerve/tissue interface of the renal nerves. Alternatively or in addition to this, a reference may be an extrapolated surface roughly equidistant between the membrane surrounding the renal nerves. In other embodiments, renal artery surfaces may be used as a reference surface. Such surfaces may comprise the blood/tissue interface or the inner surface of the lumen of the renal artery. Alternative embodiments may employ an outer surface of the renal artery as the reference surface, although the surface may be more easily identified from the three-dimensional planning image data by introducing imaging contrast agent during the planning image acquisition step 42.

The reference surfaces (e.g., boundary between the blood (including the added contrast) and the renal nerves and/or the arterial tissue) in each slice of the CT data can be segmented in one, some, or all of the volumetric datasets associated with the cardiac cycle phases. The segmented regions can be stacked or assembled together, and smoothing techniques can be applied between the boundaries of the slices. This allows the planning medical professionals to input an appropriate lesion pattern as a series of lines or curves relative to the renovascular tissue surface, with the lines being expanded to volumes so as to provide the desired therapeutic benefit. In such embodiments, the user may optionally define the lesion with reference to the renal artery or aortic wall surface. Once the target region has been identified, existing radiosurgical planning approaches to identification of radiation sensitive structures may be implemented. Similarly, existing radiosurgical radiation beam calculating modules may be used to determine the resulting radiation distribution.

Figure 5B:
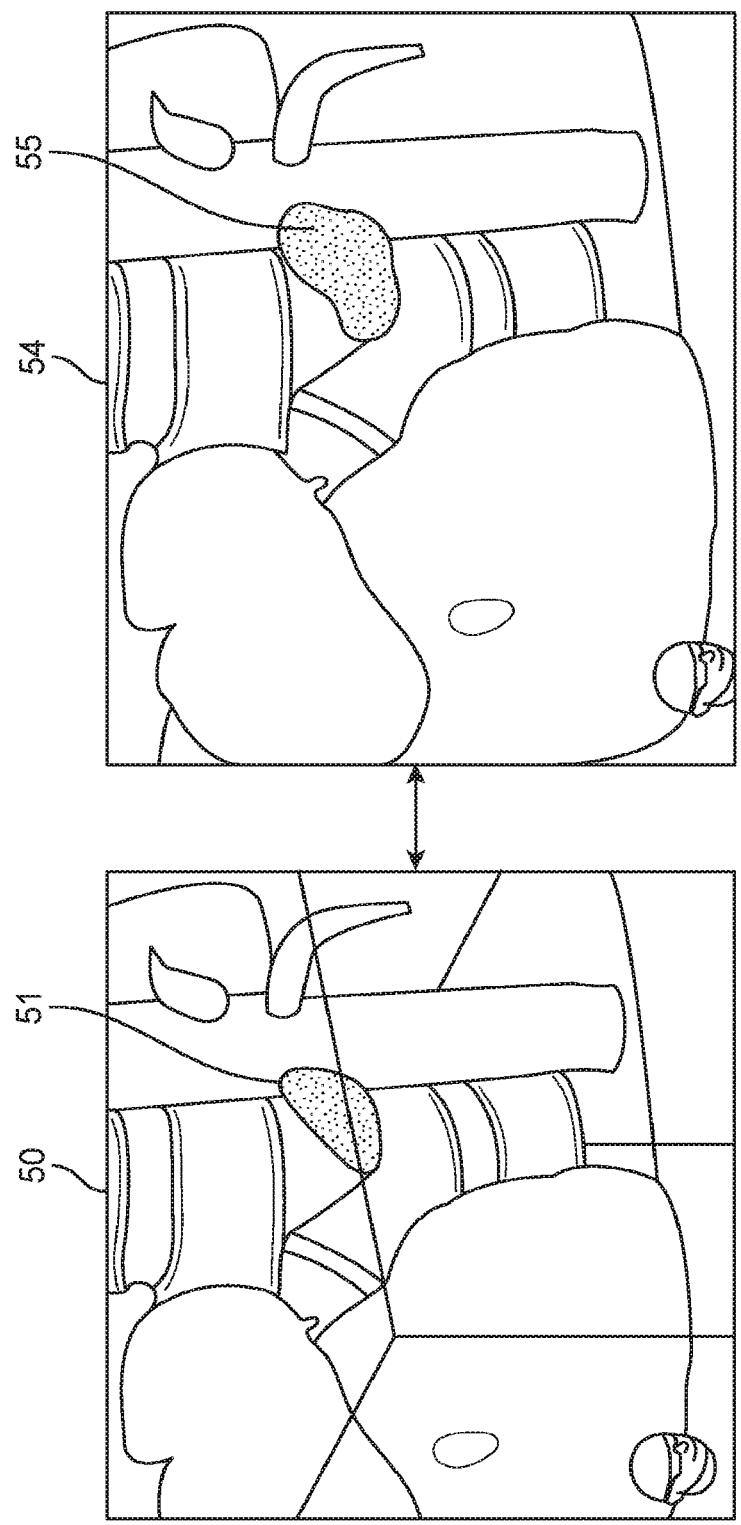
FIG. 5B graphically shows portions of a user interface display, including a planning input for a target region so as to treat hypertension, along with a graphical representation of a lesion of the renal nerves estimated by components of the treatment system.

FIG. 5B graphically shows portions of a user interface display 50 including a planning input for a target region so as to treat hypertension, along with a user interface display 54 including a graphical representation of a lesion of the renal nerves estimated by components of the treatment system for a conformal treatment plan. Along with inputting a desired lesion pattern 51 (as schematically illustrated on the left side of FIG. 5B), the planning module and user interface may output an estimate of the actual radiation exposure along the surface of a renal artery, potentially in the form of an estimated renal nerves and renal artery lesion 55 (as schematically illustrated on the right side of FIG. 5B). Estimated lesion 55 may represent the portion of renovascular tissue surface which receives a radiation dose above a necrotic threshold, optionally based on radiation beams and radiation dose output from an existing radiosurgical treatment planner. Alternative patterns may represent an estimate of tissue which will receive a sufficient dose of radiation for therapeutic remodeling so as to inhibit the hypertension. The user may interactively develop the plan based on iterative input into and output from the planning treatment module. The exemplary display of estimated lesion 55 shown on renovascular tissue surface seen in FIG. 5B shows a highlighted (false color) area of surface that receives a radiation dose higher than a first (lower) threshold and less than a second (higher) threshold. Alternative displays may indicate a tissue surface area which receives a sufficient dose to eventually cause the tissue to scar, to necrose, to ablate, and/or the like, with the indicated tissue optionally being highlighted using a color or tissue surface image which corresponds to the eventual tissue state (for example, so that scar tissue that is typically whiter than a corresponding healthy tissue is indicated by a whiter shade than the surrounding tissue, or the like).

Referring once again to FIG. 3 (along with reference to FIG. 1 and FIGS. 6A-6C) after completion of plan 44, radiosurgical treatment 46 of the renovascular system may be initiated by positioning the patient on patient support 24, bringing the patient into alignment with robot arm 14, and directing the planned series of radiation beams from the linear accelerator 12 to the target region of the renovascular system. In an exemplary embodiment, this entails remodeling the target region(s) by directing the planned radiation from outside the body toward the target region(s). In the case of a bilateral treatment, the radiation is directed to the first and second target regions in a single treatment procedure on a single day. In some embodiments, a full dose of radiation is delivered to one of the first and second target regions, followed by delivery of a full dose of radiation to the other of the first and second target regions, during the single treatment procedure on the single day. In other embodiments, partial doses are delivered to the first and/or second target regions in an alternate pattern until the full doses are delivered to the target regions. Note that the partial doses may be of about the same magnitude or may be different for the two target regions. For example, the first region may receive a 60% dose, followed by delivery of the full 100% dose to the second region, followed by delivery of the remaining 40% of the dose to the first region. Note further that these staggered doses may be delivered over a series of treatment procedures spanning respective different days. In yet other embodiments, the full dose of radiation is delivered to the first target region during a treatment procedure on a first day, and the full dose of radiation is delivered to the second target region during a separate treatment procedure on a second day.

Figure 5C:
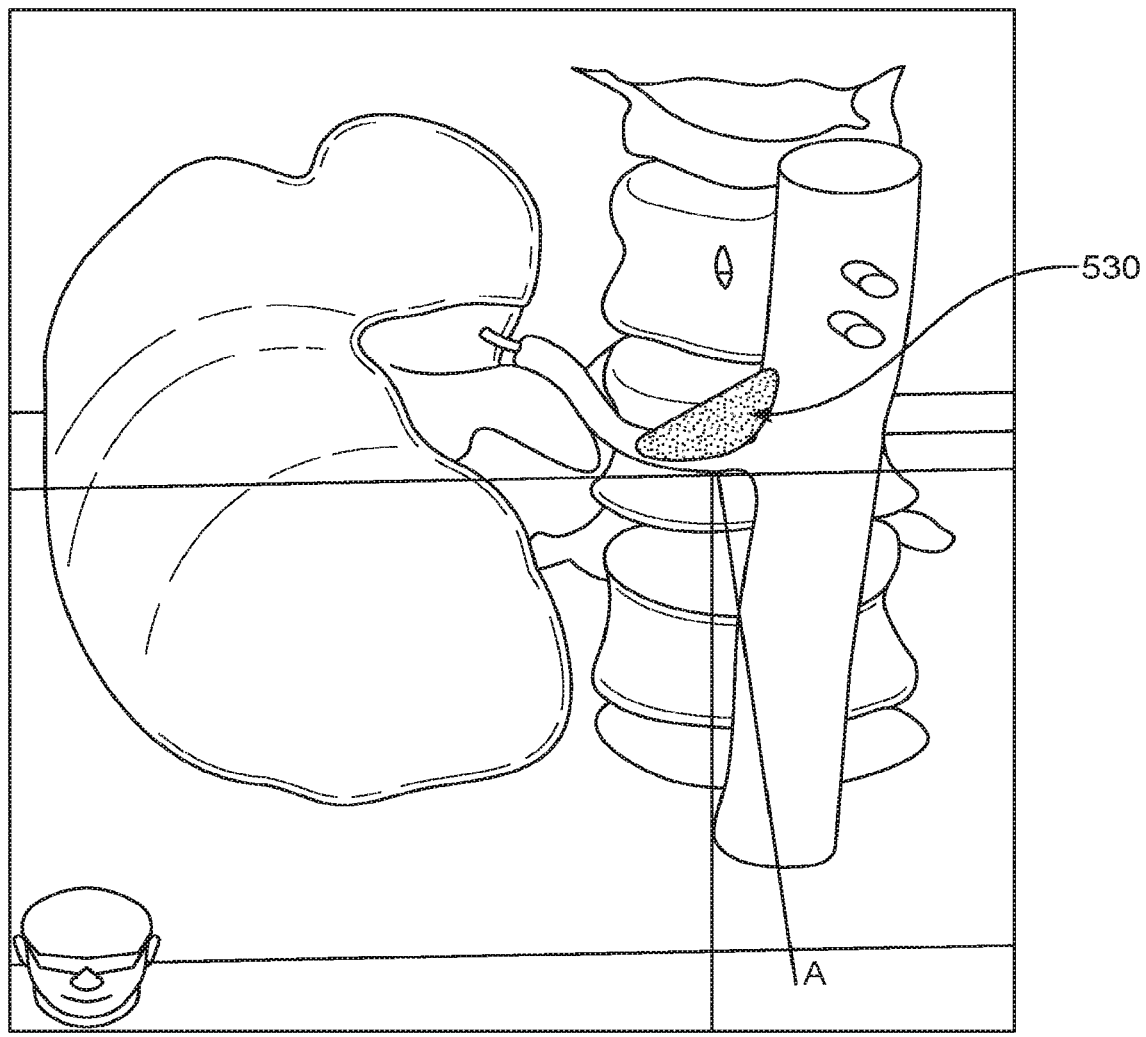
FIG. 5C depicts exemplary an isometric view of a conformal target treatment region according to an embodiment of the present invention.
Figure 5D:
FIG. 5D depicts an exemplary isometric view of radiation dose regions resulting from a conformal treatment according to an embodiment of the present invention.
Figure 5E:
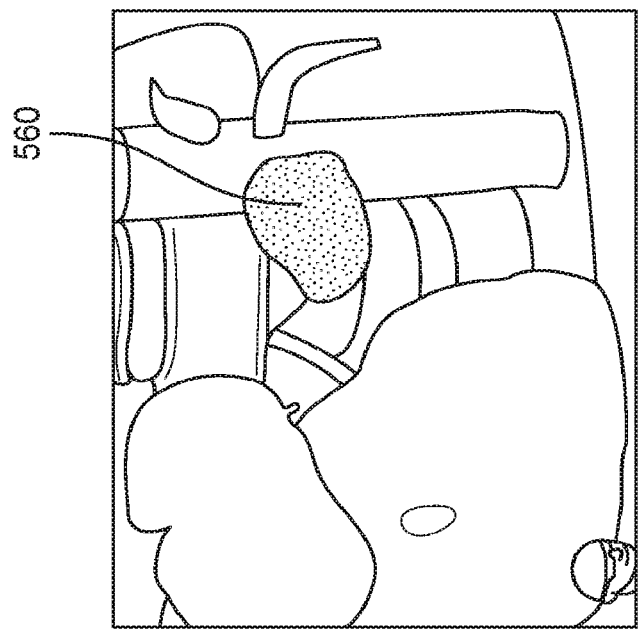
FIGS. 5E-F depict exemplary radiation clouds resulting from a conformal treatment according to an embodiment of the present invention.
Figure 5F:
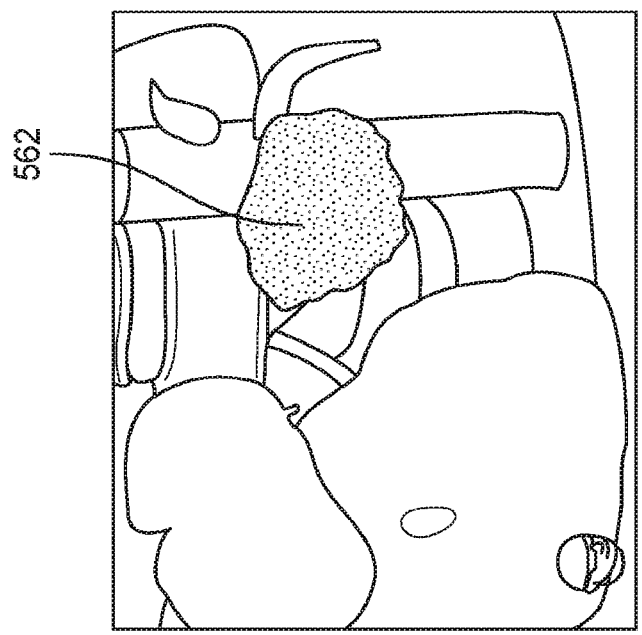
Figure 5G:
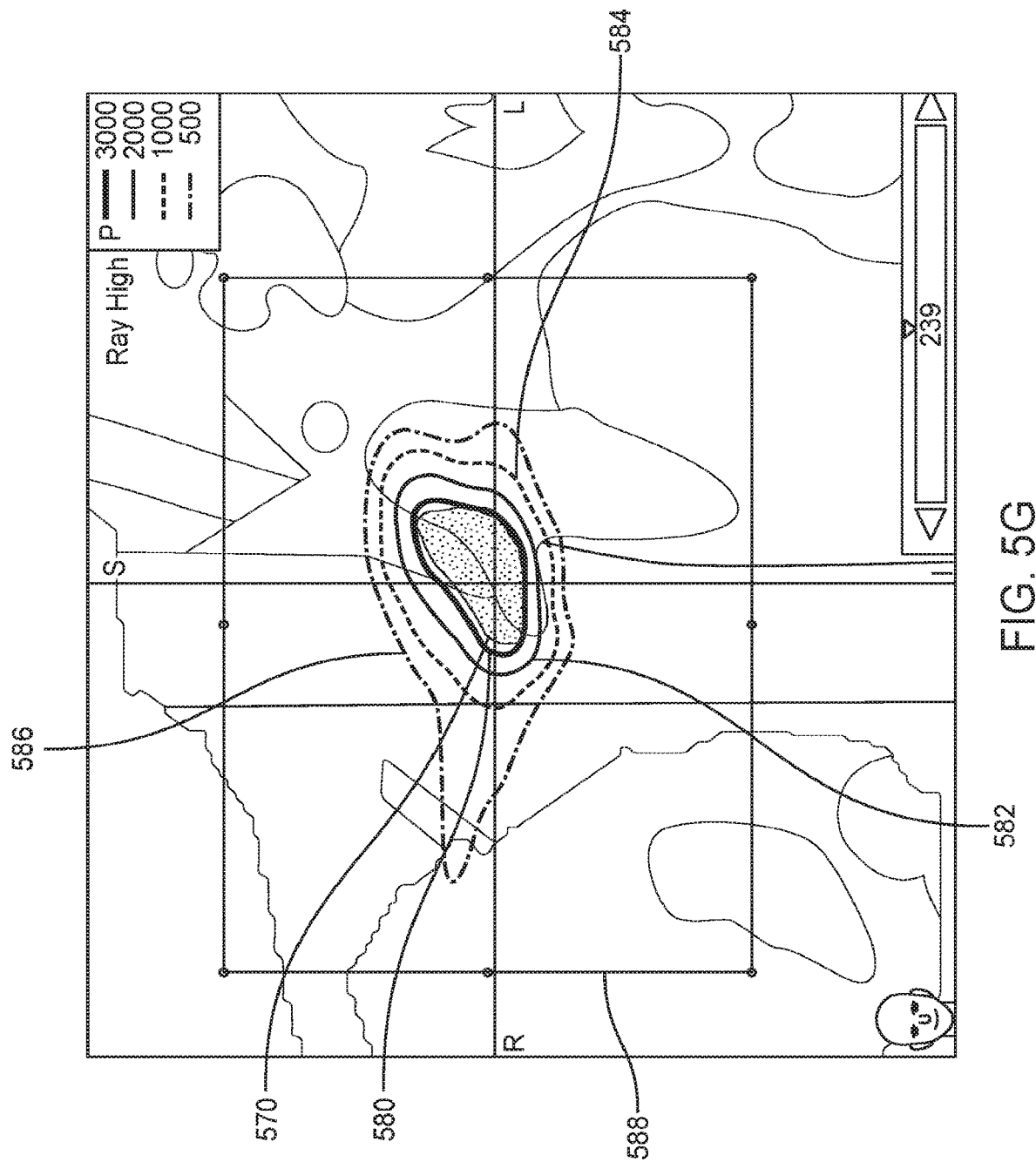
FIGS. 5G-K depict exemplary isodose lines resulting from a conformal treatment according to an embodiment of the present invention.
Figure 5H:
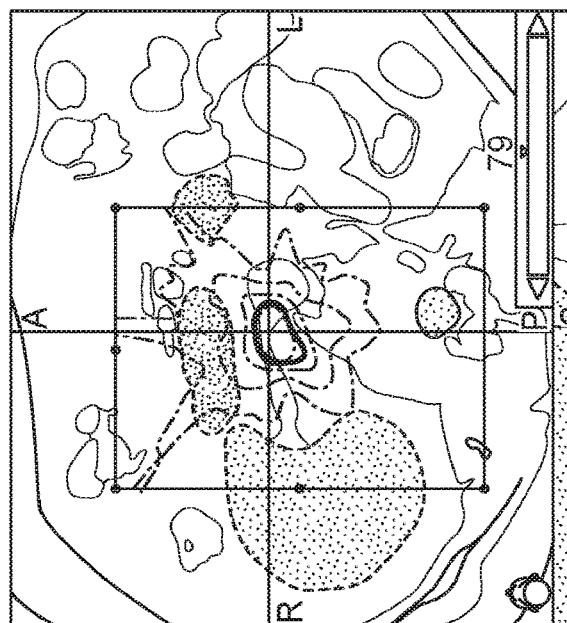
Figure 5J:
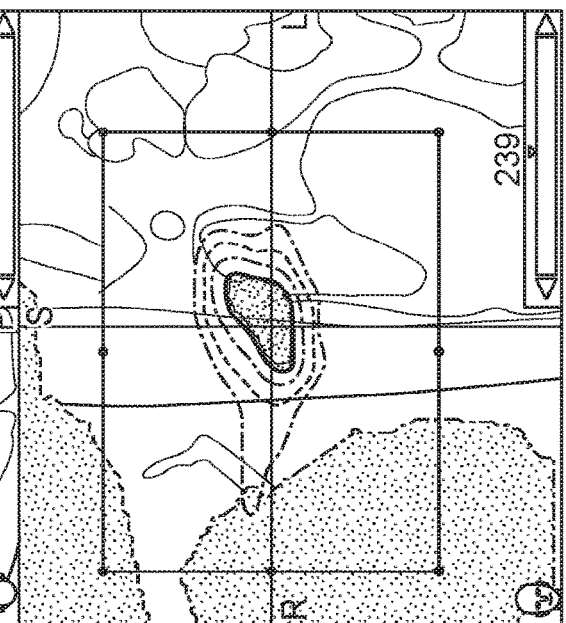
Figure 5I:
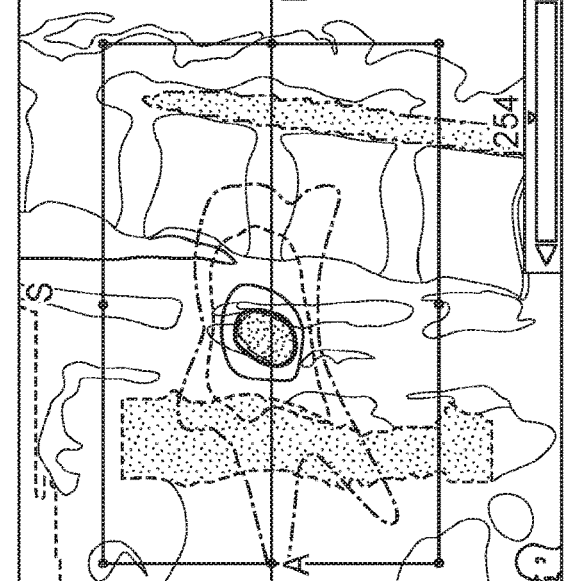

FIG. 5C depicts an exemplary conformal target treatment region 530 of the renovascular system to be imparted on that system during a radio surgical method for treating a patient having hypertension. It is noted that in other embodiments, the target treatment regions may be isocentric. While the following details an exemplary embodiment of a conformal treatment plan, other embodiments include concentric treatment plans. With respect to FIG. 5C, the size of the elements of FIG. 5C is scaled to the anatomy of an average male adult. More particularly, by implementing the methods detailed herein with respect to a conformal treatment plan, a conformal target lesion corresponding to region 530 will be imparted onto the patient's renovascular system by directing ionizing radiation to the region 530. FIG. 5D depicts an estimated three-dimensional radiation dose pattern resulting at the completion of the conformal treatment (not including later periodic treatments to address re-growth of renal nerves, etc.). The red portions 540 indicate structure subjected to about >30 Gy of radiation, the green portions 550 indicate structure subjected to about 20 to about 30 GY of radiation, and the blue portions (remainder) indicate structure subjected to about <20 Gy of radiation. The sizes of elements of FIG. 5D are scaled to the anatomy of an average male adult FIGS. 5E and 5F depict in a quasi-three-dimensional manner the outer boundaries of a 20 Gy dose cloud 560 and a 10 Gy dose cloud 562, respectively, again where size of the elements of these figures is scaled to the anatomy of an average male adult.

Figure 5K:
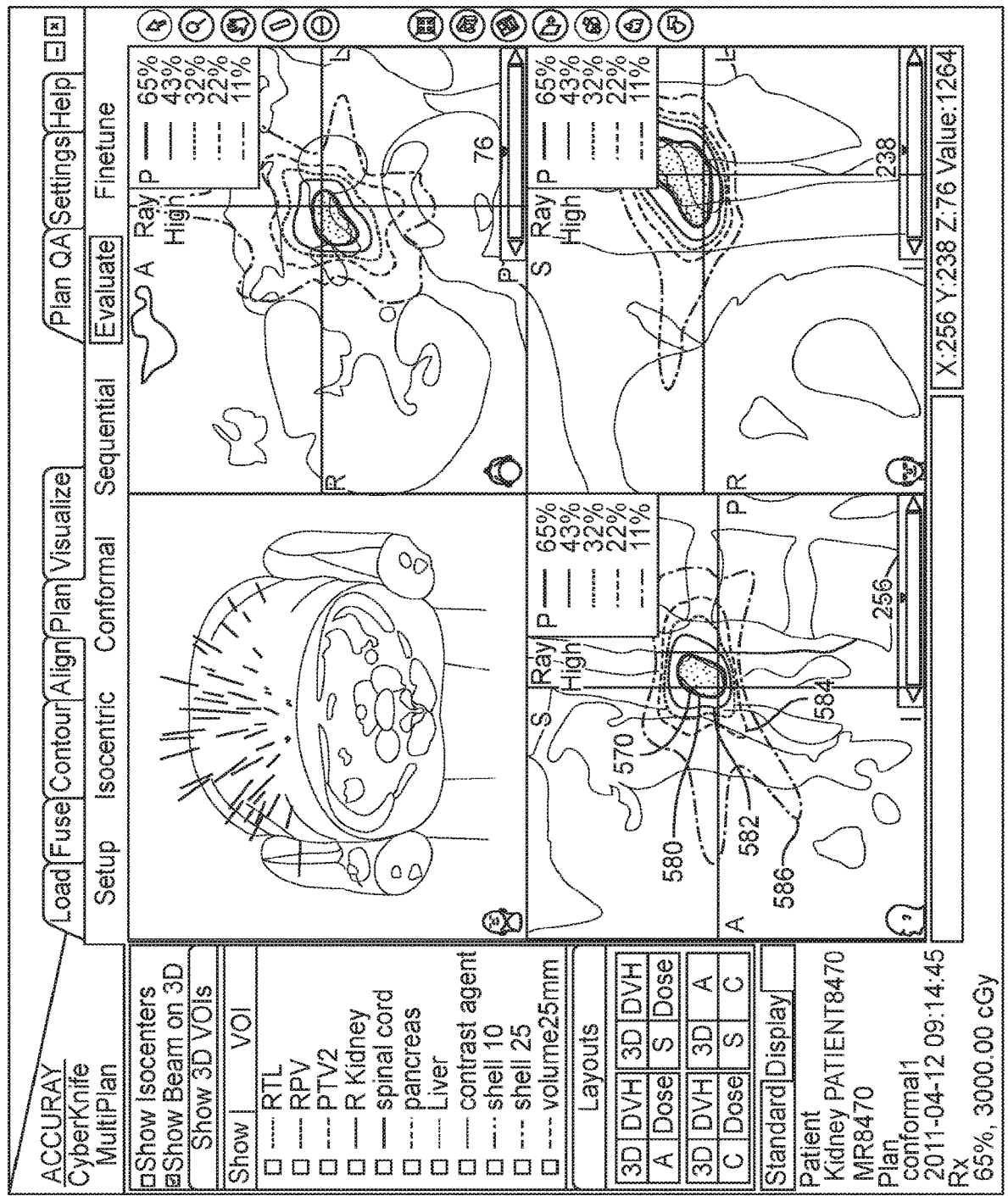

FIGS. 5G-K depict isodose lines in two-dimensional format for various planar sections taken through a patient, where the planar sections encompass structure of the renovascular system. (The information of FIG. 5K is substantially duplicative of the prior figures—FIG. 5K being presented because it presents the data in a different contrast.) FIGS. 5G-K also depict the outline of the target, which is the innermost contour, the innermost contour also having a thickness greater than the isodose lines. Starting in order from the innermost to the outermost isodose line, after the contours corresponding to target 570, the points on the innermost isodose 580 correspond to an absorbed dose of 30 Gy of radiation, and the points inside of isodose 580 receive an absorbed dose of at least 30 Gy of radiation. The points on the next innermost isodose 582 correspond to an absorbed dose of 20 Gy of radiation, and the points inside of isodose 582 receive an absorbed dose of at least 20 Gy of radiation. The points on the next innermost isodose 584 correspond to an absorbed dose of 10 Gy of radiation, and the points inside of isodose 584 receive an absorbed dose of at least 10 Gy of radiation. The points on outer isodose 586 correspond to an absorbed dose of 5 Gy of radiation, and the points inside of isodose 584 receive an absorbed dose of at least 5 Gy of radiation. It is noted that points within box 588 receive less than 5 Gy of radiation. However, it is noted that there may be areas outside a given isodose/box 588 and/or inside a given isodose/box 588 where the predicted absorbed dose is different than specified. By way of example, there may be areas near the skin that experience a dose flare and/or areas inside the isodose lines that experience a dose deficiency. The size of the elements of these figures is scaled to the anatomy of an average male adult. Along these lines, it can be seen that embodiments of the present invention result in inhomogeneous radiation delivery that delivers more than about 15 Gy within 4 mm of the outer wall of the renal arteries. It is noted that while a unilateral treatment has been depicted with respect to FIGS. 5C-5J, the data presented with respect to these figures is applicable to a bilateral treatment as well, and the opposite renovascular structure from that depicted in the FIGS. would substantially correspond to that depicted in the FIGS.

From FIGS. 5G-K, it can be seen that directing radiation from outside the body toward a targets region in accordance with a conformal treatment plan can result in a large fraction of the target region 570 receiving at least the specified prescription dose (the areas on and in isodose 580 receive the prescription dose). This prescription dose can be expressed as a percentage of the maximum dose delivered to any point in a given volume. In an exemplary embodiment, the prescription dose is 65% of the maximum dose in the field. The volume receiving $^{2/3rd}$s of the prescription dose (43% of the maximum dose, isodose 582 depicting a cross-section of that volume) has a volume of approximately 3 times the target volume (isodose 580 depicting a cross-section of that volume—all isodoses depicted in a given frame are taken on the same plane). In an exemplary embodiment, the target volume is 3.7 ml and the volume receiving $^{2/3rd}$s of the prescription dose is about 3 times that (11.1 ml).

In an exemplary embodiment, a target volume is 3.7 ml, and the volume receiving at least the prescription dose is 4.3 ml, and points within that latter volume receive at least 30 Gy of radiation. Still further with respect to this exemplary embodiment, a volume of 7.5 ml (about 2 times the target volume) receives at least 24.92 Gy of radiation, a volume of 11.1 mm (about 3 times the target volume) receives at least 20.77 Gy of radiation, a volume of 14.7 mm (about 4 times the target volume) receives at least 18.00 Gy of radiation (about ⅔rds the prescription dose), a volume of 18.7 mm (about 5 times the target volume) receives at least 15.69 Gy of radiation (about ½ the prescription dose) and a volume of 38.8 mm (about 10 times the target volume) receives at least 10.00 Gy of radiation (about ⅓$^{rd}$ the prescription dose). It is noted that in an exemplary embodiments, the just recited volumes of larger size envelop or substantially envelop the smaller volumes. From these figures, it can further be seen that directing radiation from outside the body toward a target region in accordance with a conformal treatment plan results in respective radiation dose distributions to most of the target region 570 of at least the prescription dose and a dose distribution at a boundary (isodose 586) of a volume about seven to ten times the volume of the target region 570, and approximately centered thereabout, of about one-fifth of a unit of radiation. By directing radiation to a target treatment region to obtain the exemplary isodoses FIGS. 5G-J and/or directing the radiation according to other embodiments detailed herein and variations thereof, where the target region surrounds a majority of a perimeter of a renal artery, a collateral dose of the directed radiation into the walls of the renal artery is sufficiently less than a dose of the radiation in the target region so as to inhibit tissue response-induced occlusion of the renal artery.

Figure 6A:
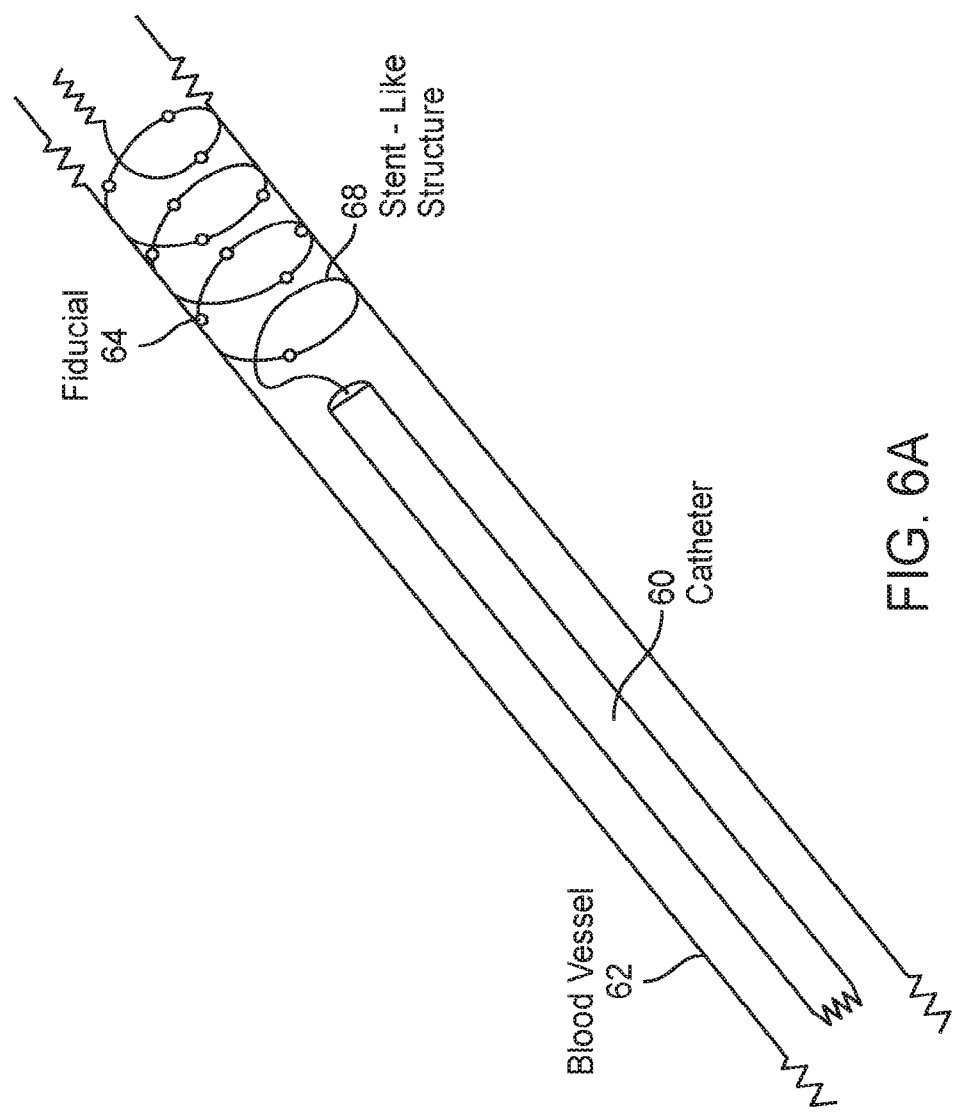

As noted above, the target region of the renovascular system (i.e., the renal nerves) may not be readily identified in the images obtained by image guidance system 16. To enhance tracking of the renal nerves, it will often be advantageous to advance a catheter 60 through a blood vessel 62, such as the renal artery, so as to couple one or more surrogate structures 64 to a tissue that moves in correlation with the target region of the renovascular system. In the embodiment of FIGS. 6A-6C, catheter 60 has a distal end 66 with astent-like structure 68. The stent-like structure 68 can be expanded atraumatically within a lumen of a renal artery so as to support fiducials 64 against the tissue surface of the surrounding luminal wall. Stent-like structure 68 can also be radially contracted and withdrawn proximally after radiosurgical treatment of the target region. The exemplary method illustrated in FIGS. 6A-6C shows a series of fiducials 64 being deployed in a non-colinear configuration in the renal artery 62. Such a non-colinear configuration facilitates defining a three-dimensional offset based on image data of the fiducials, with the exemplary offset extending between the fiducials and the target region, the target regions here represented by element 63, as seen in FIGS. 6B and 6C.

Figure 7:
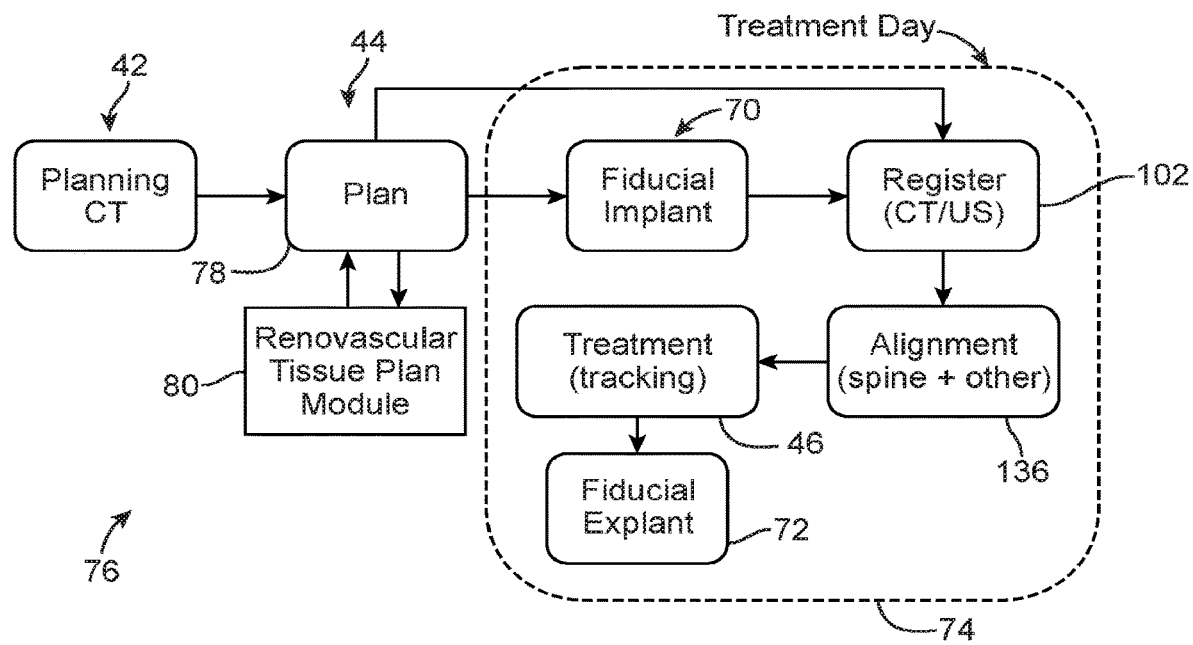
FIG. 7 schematically illustrates a radiosurgical system and method for treating a renovascular system in which fiducials are implanted into the renal artery or adjacent structures after planning of the target regions and the associated series of radiation beams.

Referring now to FIGS. 3 and 7, the time associated with acquiring images 42 and planning treatments 44 may, taken together, represent at least a significant portion of a day. The radiosurgical treatments themselves 46 may likewise take a significant amount of time, while the surgical implantation and explantation of fiducials 70, 72 also involve some time. As it is sometimes desirable to avoid leaving structures implanted in or adjacent the renovascular tissues for more time than is necessary, it may be beneficial to perform the fiducial implantation 70 and fiducial explantation 72 on a radiosurgical treatment day 74, while the imaging 42 and planning 44 are performed prior to the treatment day.

However, a result of this post-planning implantation of fiducials 70 is that the fiducial images and locations may not be available in the planning image data prior to the treatment day. Note that, for this reason, post-planning fiducial implantation may be contrary to standard radiosurgical treatment practice. Should the planning and treatment extend over two days or longer, then systemic low to medium dose anticoagulation (blood thinners) of the patient may be utilized with an indwelling catheter in the arterial system.

In light of the above, an exemplary treatment methodology 76 generally includes obtaining a planning image in the form of CT data 42 without any artificial or implanted tracking fiducials. Contrast agent will typically be used during the image acquisition to facilitate identification of the blood-heart tissue surface, and the planning image data may include a time series of three-dimensional datasets, with each three-dimensional dataset typically including a series of offset planar scans through the heart tissue.

As described above, planning may be performed using a general radiosurgical treatment plan module 78, along with a specialized renovascular treatment plan module 80. The general plan module 78 may be used during treatment of tumors and/or the treatment of arrhythmia (as is detailed, for example, in U.S. patent application Ser. No. 12/838,113, entitled Heart Treatment Kit, System, and Method for Radiosurgically Alleviating Arrhythmia, the contents of which are incorporated by reference herein in its entirety), for example, to identify isocentric or other irradiation target profiles in some of the planar CT slices of the planning image. Radiation-sensitive collateral tissues may also be identified in the planar CT scans, and based on this input the general treatment planning module may generate a series of radiation beams and associate dose information in the planes of the CT scans. So as to facilitate treatment of hypertension with tissue-surface based lesion patterns, renovascular tissue plan module 80 may interface with (and take advantage of) the capabilities of general plan module 78.

Renovascular tissue plan module 80, as with other data-processing modules described herein, will typically comprise computer processing hardware and/or software, with the software typically being in the form of tangible media embodying computer-readable instructions or code for implementing one, some, or all of the associated method steps described herein. Suitable tangible media may comprise a random access memory (RAM), a read-only memory (ROM), a volatile memory, a non-volatile memory, a flash memory, a magnetic recording media (such as a hard disk, a floppy disk, or the like), an optical recording media (such as a compact disk (CD), a digital video disk (DVD), a read-only compact disk, a memory stick, or the like). The various modules described herein may be implemented in a single processor board of a single general purpose computer, or any one or more of the modules may run on several different processor boards of multiple proprietary or commercially available computer structures, with the code, data, and signals being transmitted between the processor boards using a bus, a network (such as an Ethernet, an Intranet, or an Internet), via tangible recording media, using wireless telemetry, or the like. The code may be written as a monolithic software program, but will typically comprise a variety of separate subroutines and/or programs handling differing functions in any of a wide variety of software architectures, data processing arrangements, and the like. Nonetheless, breaking the functionality of the program or hardware into separate functional modules is useful for understanding the capabilities of the various aspects of the invention.

Renovascular tissue plan module 80, as with other data-processing modules described herein, may comprise "programming." The term programming, as used herein, includes hardware, software and firmware.

The exemplary renovascular tissue plan module 80 interfaces with the Multiplan™ planning module of the CyberKnife™ radiosurgical system or other system capable of delivering the prescribed plan. Rather than inputting shapes onto the planar CT scans, the user interface of the heart plan module 80 can define lines and/or curves on the tissue surface, with the renovascular tissue plan module identifying the associated shapes on the CT scan planes. The renovascular tissue plan module also graphically displays an estimated lesion of the heart tissue on a display of either heart plan module 80 or radiosurgical plan module 78 (as generally described above regarding FIG. 5.) This allows the medical professional or professionals planning the patient's treatment to verify that the lesion pattern is appropriate and capable of producing the desired therapeutic benefits. An exemplary renovascular tissue plan module 80 also simulates the effects of gross misalignment between the patient and/or heart and the radiosurgery treatment system 10 (with associated output to the planning medical professional(s)), and/or provides output to the planning medical professionals regarding tracking errors (for example, in 6 degrees of freedom) on the estimated lesion location and shape.

On a calendar day after plan 44 has been completed, and such as on a treatment day 74, the patient will undergo surgical implantation of the tracking surrogate or fiducial 70. In some embodiments, as will be detailed below, the fiducial or fiducials may be implanted the day prior to treatment being initiated, and/or treatment may take place on more than one day (with fiducials optionally being explanted and new fiducials being implanted between treatments). Fiducials may be implanted by advancing a distal end of a catheter through a blood vessel to a renal artery or vein, with the distal end of the elongate flexible catheter body coupling a high-contrast fiducial set to the renal artery tissue so that the fiducial moves in correlation with the target tissue. Exemplary coupling mechanisms include radially expandable balloons or stent-like structures (optionally including helical coils, braids, or the like) as described above regarding FIGS. 6A-6C. These expandable bodies may be biased to expand radially when released from a surrounding catheter sheath (such as by pulling the sheath proximally from over the expandable body) or may be expanded by introducing a fluid (typically a liquid such as saline or a gas such as air) into an anterior of a balloon, shortening a length between a proximal end and a distal end of the expandable body, or the like. The expandable body will typically be configured to contract radially such as by advancing a sheath over the expandable body, emptying inflation fluid, pulling a filament of a helical coil into a sheath, or the like. A wide variety of alternative reversibly expandable structures are known in the stent field, and many of these can be modified for use to temporarily affix a surrogate to a tissue of the heart.

Figure 7A:
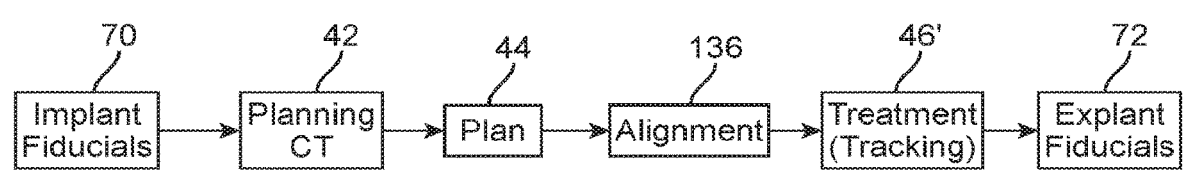
FIG. 7A schematically illustrates an alternative radiosurgical system and method for treating a renovascular system in which fiducials are temporarily implanted into the renal artery or adjacent structures before planning of the target regions and the associated series of radiation beams, and are explanted after treatment.

FIG. 7A schematically illustrates an alternative workflow that may employ many aspects of the inventions described herein. In the alternative treatment workflow 76', the fiducial implantation 70 may take place prior to acquiring a planning CT 42 or other planning image. Following acquisition of the planning image, the patient may return home for treatment on another day (so as to allow treatment planning 44 to take at least a significant portion of a day, the planning often taking one or more days to complete). Tethered intraluminal surrogate systems (in which fiducials remain tethered to an intraluminal access site by an elongate catheter body) might optionally be temporarily implanted for more than one day. Alternatively, it may be beneficial to instead employ non-tethered intraluminal surrogate systems (in which temporarily implanted and released fixation structures support the fiducials within a lumen of the renovascular system, while no catheter body extends between the vascular access site and the surrogate system). Such a non-tethered fixation structures may be configured to facilitate subsequent coupling of a catheter thereto and endoluminal recapture and retrieval of the surrogate system during fiducial explantation 72. Still further alternative embodiments of workflow 76' may employ an in-patient and/or same day treatment approach. For example, fidicial implantation 70, planning image acquisition 42, treatment planning 44, alignment of the patient with the treatment system 136, and treatment 46', and optionally even explantation 72 may be coordinated so as to be completed within one day, often with the patient remaining at the hospital or other treatment facility throughout the treatment period. In embodiments entailing remodeling a target region of the renovascular system, the directed radiation is directed to the target region with reference to the implanted surrogate(s). Related alternative embodiments may extend beyond a single day to two or three days (though typically less than a week), with at least explantation 72 (and optionally the treatment itself) occurring two days, or three days after the treatment, or within one week after the treatment), often while the patient remains at the hospital or other treatment site. Fiducial explantation 72 again typically occurs at the end of the procedure. In alternate embodiments, the surrogate(s) may be permanent implants. In this regard, the surrogate(s) may remain implanted in the body of the patient for at least a year or until dissolution, in the case of dissolving surrogates.

It is noted that at least portions of the therapeutic methods detailed herein, such as those related to FIGS. 3, 7, and 7A, may be repeated in a pattern having a standard or non-standard period of months or years, and the therapeutic methods may be intermixed with other therapeutic methods during the repetitions. Such methods may be used to destroy at least some of the renal nerves that grow back after the initial therapy to achieve intermittent periodic blocking or re-down-regulation of renal nerve activity. Indeed, such methods may include implanting permanent surrogates that may remain implanted in the patient, and remain clinically usable to practice the treatments detailed herein, for about 1, 1.5, 2, 2.5, 3, 3.5, 4, 4.5 and/or 30 years, etc. Accordingly, embodiments of the present invention may include a treatment corresponding to those of FIG. 7 or 7A without the step of fiducial explantation, followed by a treatment 0.5, 1, 1.5, 2, 2.5, 3, 3.5, 4, 4.5 and/or 30 years later corresponding to those of FIG. 7 or 7A, except the step of fiducial implantation is not executed in the latter treatment because the fiducials remain in the patent in a usable condition.

Figure 6E:
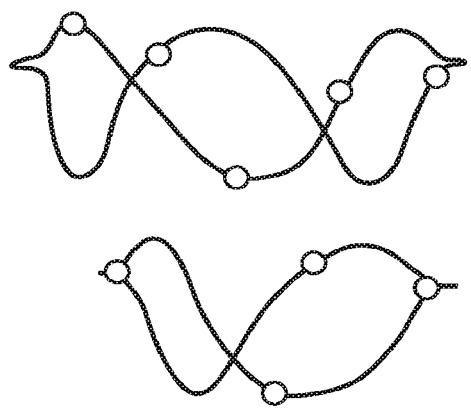
FIGS. 6D-6K show temporarily implantable surrogate systems, including catheter-based intraluminal fixation structures and/or non-tethered retrievable intraluminal fixation structures, as well as their use when deployed in a renal artery so as to provide a tracking surrogate.
Figure 6D:
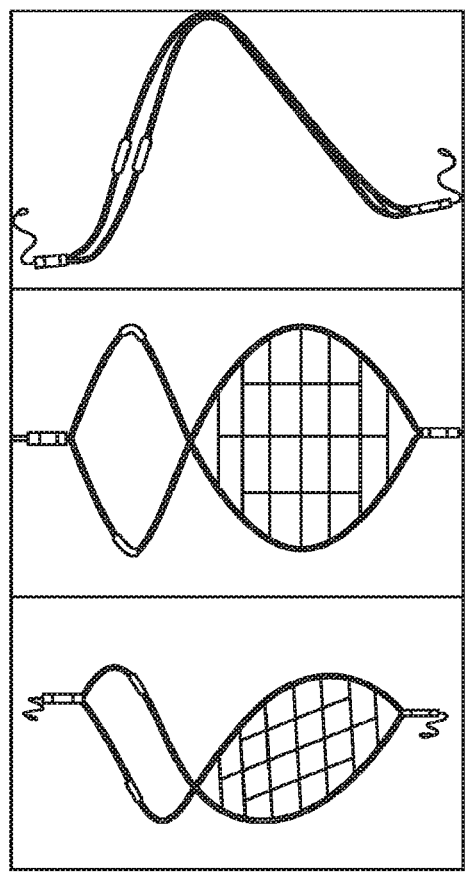

Referring now to FIGS. 6D and 6E, an exemplary non-tethered surrogate system can be understood. FIG. 6D shows a temporarily implantable fixation structure comprising two opposed helical wires coupled together. This exemplary non-tethered fixation structure can be deployed and retrieved intraluminally using catheter structures, and which can temporarily support one or more fiducials during imaging, planning, and/or treatment. The fixation structure of FIG. 6D may employ (or may be derived or modified from) a structure developed for use as a vena cava filter by Crux Biomedical Inc. of Menlo Park, CA, and the fixation components and use of this embodiment may be further understood with reference to US Patent Publication No. 2008/

0147111, published on Jun. 19, 2008 and entitled "Endoluminal Filter with Fixation," in the name of Johnson et al. (application Ser. No. 11/969,827, filed Jan. 4, 2008), the full disclosure of which is incorporated herein by reference. The methods and catheter structures used for deployment of the structure of FIG. 6D (as well as the methods and catheter structures used for recapture and retrieval) may also be understood with reference to the '111 publication. As can be seen in FIGS. 6D and 6E, for use with the radiosurgical treatment systems and methods described herein, one or more enhanced contrast passive fiducials may be affixed (directly or indirectly) to two opposed outer helical wires or other filaments coupled together at their ends, with the crossings and couplings of the wires defining frames therebetween. Alternative embodiments may employ an active fiducial affixed to the outer helical wires, with the active fiducial optionally having a tether or being self-powered. The filter filament elements shown in FIG. 6D extending between the outer helical wires may be removed or omitted, or may remain in place in some embodiments. The crossing helical wires may define two, three, or more frames (as shown in FIG. 6E).

One or more two-frame temporary intraluminal fixation structures may be implanted in the renal arteries and/or adjacent the renal nerves to support non-collinear fiducials so as to facilitate tracking of a moving tissue of the renovascular system, such as the renal artery and/or the renal nerves. Anatomical structures of the body may be identified for orientation. Target regions may be tracked with the aid of a surrogate system having multiple loops or frames temporarily implanted within a renovascular structure or a structure adjacent a renovascular structure. Prior to deployment, the non-tethered surrogate system can be pre-loaded inside a delivery and/or guiding catheter. An elongate flexible body (optionally a dilator) inside the guiding catheter acts as a plunger to push out the surrogate system to be indwelling inside a vessel. A custom delivery system can also be used. Once the treatment is complete, a retrieval catheter such as a snare can recapture and retrieve the indwelling surrogate system, for example, by grabbing onto a protrusion or hood disposed at a proximal end of the fixation structure (see FIG. 6D). The fixation structure may optionally have anchors protruding radially from an outer surface of the helical wires, similar to those provided on the Crux™ IVC filter to provide better fixation to the vessel walls. To deliver a fiducial system to the renal arteries, a flow-directed balloon catheter similar to a Swan-Ganz catheter may be used. Following this, a guide-wire can be inserted to the delivery site. The guide-wire may also be twisted while the flow-directed balloon is inflated to select a right or left renal artery. The Swan-Ganz is then withdrawn while the guide-wire is in place, and a catheter pre-loaded with the surrogate system is advanced to the target site over the wire. The surrogate system is deployed at the target site. The guide-wire and the delivery catheter may be withdrawn, leaving the surrogate system behind. Alternatively, a flow-directed balloon can be integrated with the fiducial delivery system. Hence, the surrogate system may be tethered and/or non-tethered (indwelling).

Figure 6F:
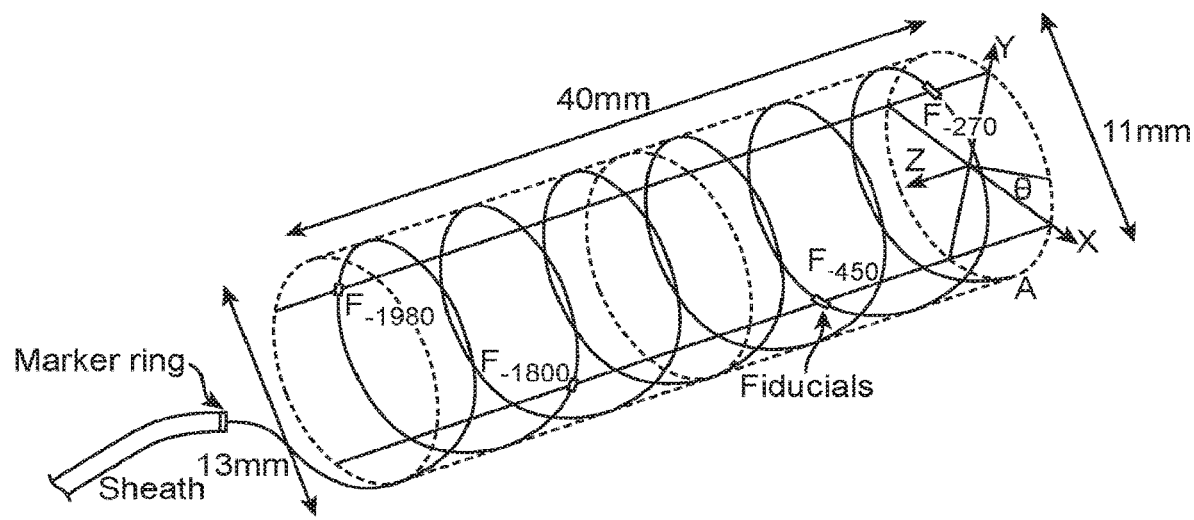
Figure 6G:
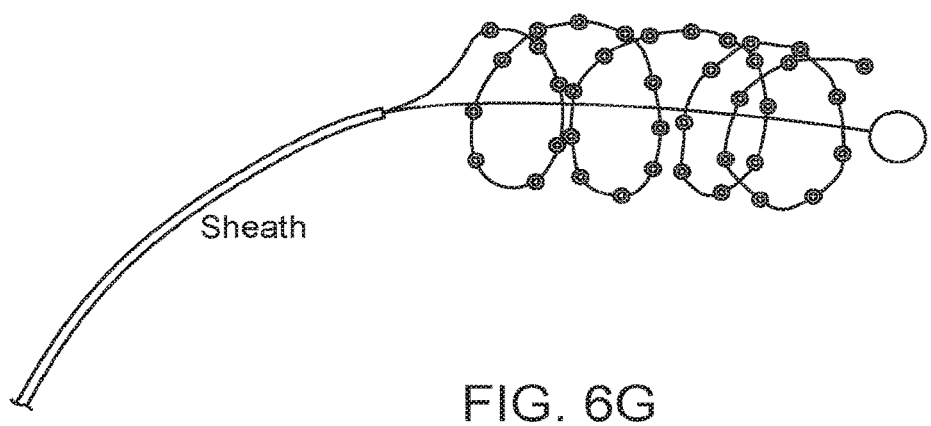
Figure 6H:
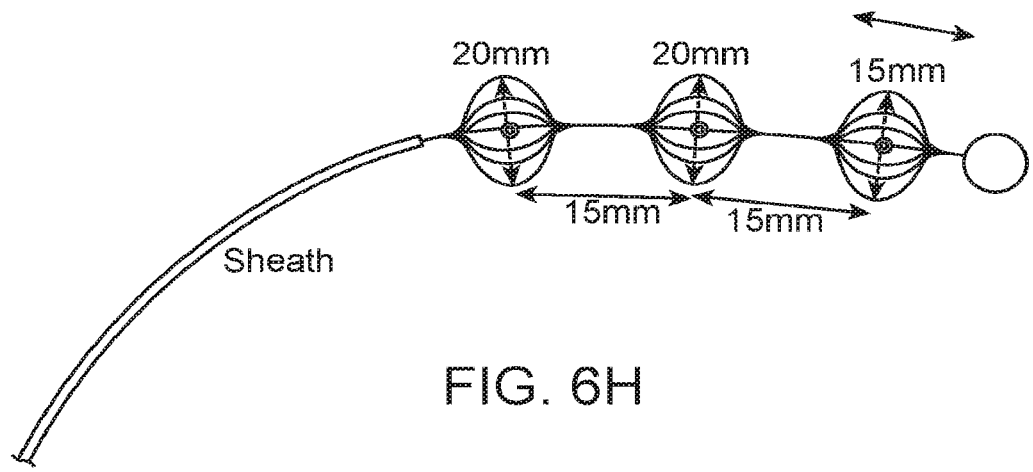
Figure 6I:
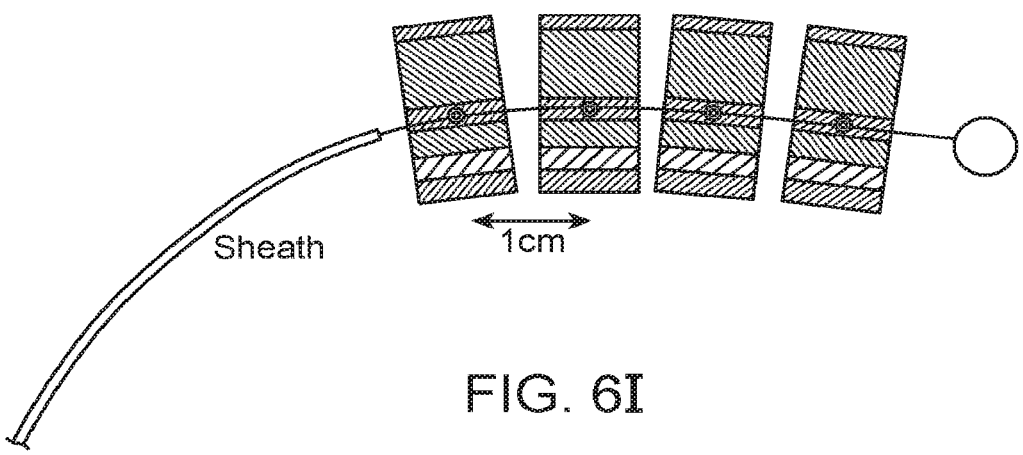
Figure 6J:
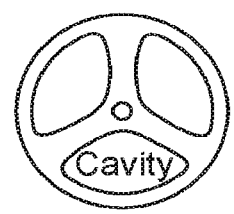
Figure 6K:
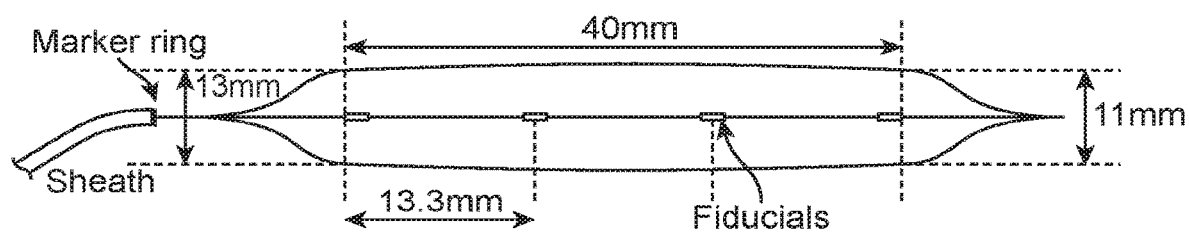

Referring now to FIGS. 6F-6K, additional alternative fixation structures are illustrated. In the embodiment of FIG. 6F, a helical stent-like fixation structure supports fiducials abutting the walls of the blood vessel in which the fixation structure is expanded, typically by releasing a helical filament structure from within an associated sheath. In the embodiment of FIG. 6G, a helical stent-like fixation structure includes a flow-directed balloon near a distal end of the surrogate system and/or deployment catheter to help guide advancement of the deployment catheter downstream within a blood vessel. Once again, the fiducials will abut the walls of the surrounding blood vessel, and the fiducials may be separated along the helical length of the fixation structure at regular or varying distances, for example, at every 1 cm. In the embodiment of FIG. 6H, an axially series of expandable basket-like structures are each defined by a circumferential series of flexible members. A pull-wire allows a length of the basket like structures to shortened and their diameter expanded in situ from outside the patient. A flow-directed balloon at the distal end of the baskets helps guide the catheter downstream, and the fiducials may remain at the center of the blood vessel when the baskets are expanded by mounting the fiducials along to the pull-wire or to another structure that remains along the center of the baskets. FIGS. 6I and 6J schematically illustrate a series of spoke and wheel balloons (optionally referred to as cartwheel balloons) with an optional flow-directed distal balloon to help guide distal advancement of the deployment catheter downstream along a blood vessel. Fiducials may again be mounted along a central portion of one or more of the balloons. FIG. 6K schematically illustrates an alternative expandable support structure comprising a braided tube with a fiducial-supporting pull wire disposed along a center of a braided tube. Shortening of the tube by pulling the pull wire relative to the proximal end of the tube results in radial expansion of the tube, with the fiducials remaining substantially along the center of the blood vessel.

In yet other embodiments of the present invention, the fiducials are gold seeds or seeds of a sufficiently detectable material that are implanted into the recipient. Implantation of such seeds may be accomplished via a catheter snaked through a blood vessel, or via a more direct method, such as through the use of a percutaneous needle. In some embodiments, the seeds are substantially non-toxic seeds, with respect to the dosages used in the methods herein, with an electron density visible on CT and/or guidance imaging.

It is noted at this time that in many embodiments, the fiducials are implanted such that the tissue to which they are attached moves in a direction and with a speed substantially the same as the movement of the renal artery, both do to respiration and due to the heart cycle (blood pressure component and/or displacement component of the cardiac cycle), including the expansive-contractive movement of the renal artery due to increasing and decreasing blood pressure. By way of example, in an embodiment utilizing a stent to carry the fiducials, such as the embodiment detailed above with respect to FIG. 6A, the stent is configured to permit the fiducials to expand and contract with the expansion and contraction of the inner wall of the renal artery resulting from the heart cycle (blood pressure component of the cardiac cycle).

Figure 8A:
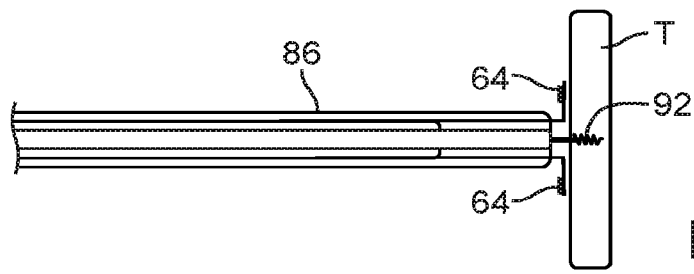
FIGS. 8A-8F illustrate alternative catheter-based surrogate systems having image-able and/or active fiducials to facilitate tracking of moving heart tissues.
Figure 8B:
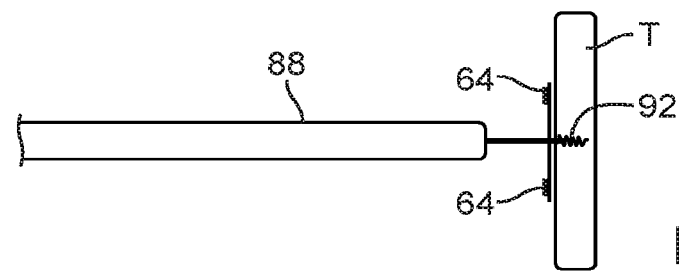
Figure 8C:
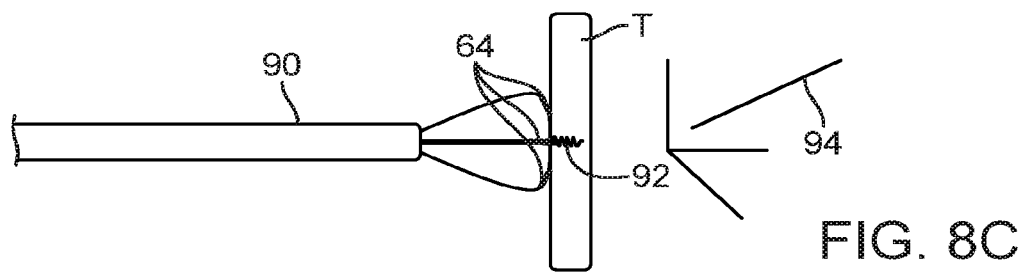
Figure 8D:
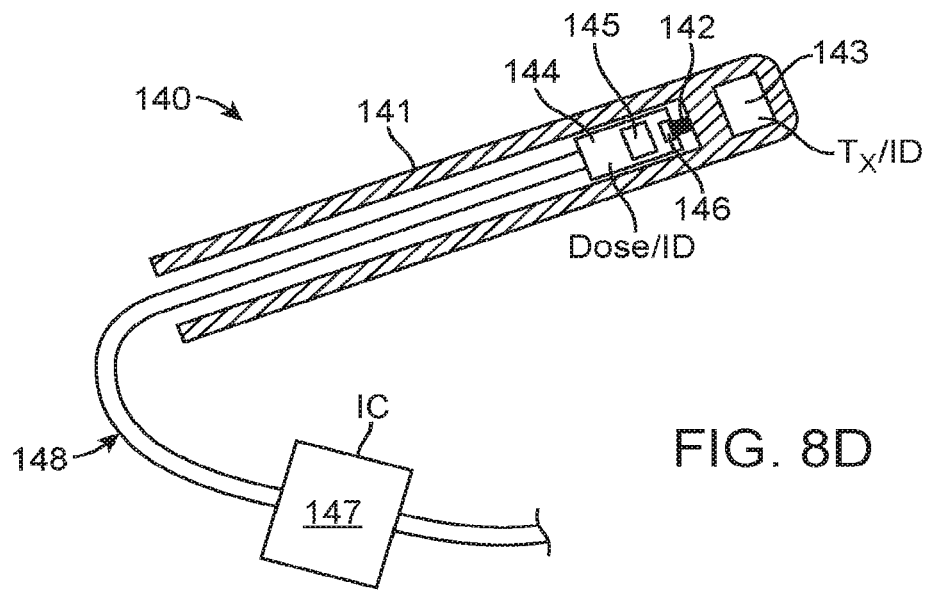
Figure 8E:
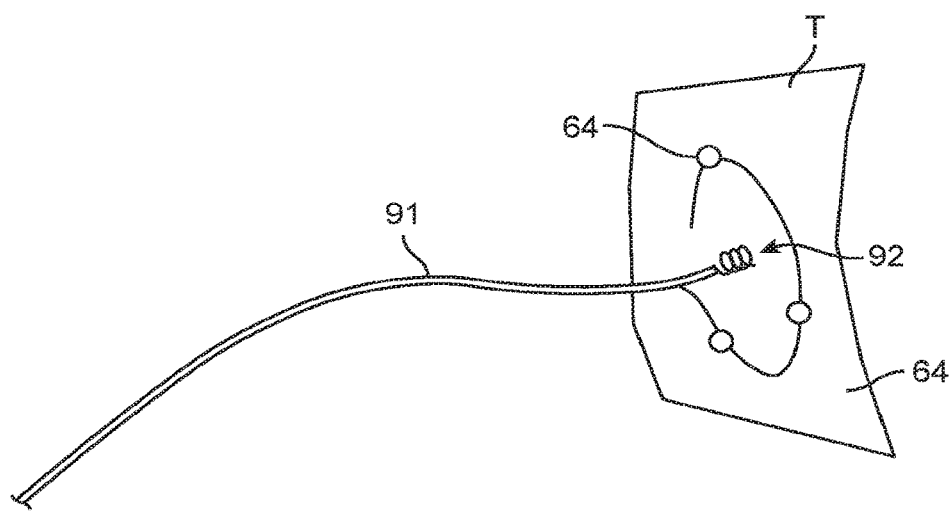

FIGS. 8A-8C and 8E schematically illustrate still further alternative catheter structures for deploying fiducials and temporarily affixing the fiducials 64 to renovascular tissue T. Catheters 86, 88, 90, 91 affix fiducials 64 to tissue T using a helical screw 92 that can be screwed into tissue T by rotating the catheter about its axis, with the exemplary helical screw being similar in structure to helical cardiac pacemaker leads. Fiducials 64 are supported by resiliently or plastically flexible members, allowing the fiducials to expand from the substantially linear configuration with the surrounding sheath to a non-colinear deployed configuration in engagement with the tissue T. The non-colinear deployed configuration of fiducials 64 enhances the accuracy with which a three-to-six-dimensional offset (shown schematically by offset 94 in FIG. 8C) can be determined relative to three-dimensional or bi-plane images of the fiducials. As the target tissue may be identified using a three-to-six-dimensional offset 94 from the fiducials during treatment, this may enhance tracking accuracy. The resilient structure of catheter 91 is biased to form an arc or lasso engaging a tissue intersecting helical screw at least partially around the helical screw. FIG. 8E shows an alternative fiducial deployment catheter 89 in which a deployable cone 89*a* disposed at a distal end of the catheter can be temporarily affixed to an endocardial tissue surface T by applying a vacuum within the catheter using a vacuum source such as a syringe 89*b* coupled to a proximal end of the catheter. A fiducial catheter 89*c* can then positioned adjacent the distal end of deployment catheter 89 by advancing the fiducial catheter distally through a port 89*e* at the proximal end of the deployment catheter. Additional monitoring or ablation devices may also be advanced distally through the port, and deployment of the cone may be effected from the proximal end of the deployment catheter using an actuator 89*f*. Fiducials 89*d* may be mounted to or near the distal end of fiducial catheter 89*d*.

A still further alternative catheter-based fiducial structure which may be adapted for use in the present invention is shown in FIG. 8D, and is described in more detail in U.S. Patent Application 2008/0292054, entitled "Device for Measuring Administered Dose in a Target" (the full disclosure of which is incorporated herein by reference). While the exemplary embodiment described in that reference comprises a urethral catheter for facilitating treatment of prostate cancer, a similar structure might be modified by inclusion of a helical screw 92 or stent-like structure 68 as described above regarding FIGS. 8A-8C, 8E, and FIGS. 6A-6C. Some embodiments may include the dose measurement components of catheter 140 shown in FIG. 8D, although many other embodiments will omit dose measurement capabilities. Regarding exemplary catheter 140, that structure includes an elongate flexible catheter body 141 provided with an electrical guide 142 and an electrical marker 143. The marker comprises a transmitter $T_x$ used to determine the position of a target area in a patient and in identification ID of the patient. The implant further comprises a combined dose and identification unit 144 having a dose sensor 145 used to detect the amount of administered dose in the target area and a dose identification Dose/ID.

The combined dose and identification unit 144 is provided with a connector 146 that is arranged to be connected to electrical guide 142, and can ensure the correct unit 144 is connected by comparing the dose identification Dose/ID and the ID of the patient in the electrical marker 143. The transmitter $T_x$ may be powered through the combined dose and identification unit 144 so as to verify position of the catheter 140, since movement of the catheter (and tissue to which the catheter is attached), determine an offset between a transmitter signal-based position of the catheter and an image-based location of the catheter, and the like. The combined dose and identification unit 144 is connected to an externally arranged integrated circuit 147 through wires 148, and the integrated circuit 147 includes the functionality associated with dose conversion as more fully described in U.S. Patent Publication 2008/0292054. Suitable alternative active fiducials often rely on electromagnetic or ultrasound transmission to or from the fiducial so as to identify a location of the fiducial (independent of any imaging system obtaining an image of the implanted fiducial with or without the surrounding tissue). Suitable electromagnetic position sensing structures may be commercially available from a variety of suppliers, including the Carto AccuNav™ catheter available from Biosense Webster, the various three-dimensional guidance tracker structures commercially available from Ascension Technology Corporation of Vermont, the ultrasound sensor and systems commercially available from Sonometrics Corporation of Canada, the EnSite™ cardiac mapping system from St. Jude Medical of St. Paul, Minnesota and variations thereof applicable to renovascular mapping, and the like. These active fiducials send and/or receive signals indicating a position of the fiducial, movement of the fiducial, and the like, with this signal being used as an input into the processor of the radiosurgical treatment system for tracking of the target tissue.

The fiducials, fixation structures, and/or surrogate systems described herein may be attached in and/or to a renal artery, as well as in and/or to other tissue structures proximate the renal arteries and/or the renal nerves. In other embodiments, the surrogates can be attached to the walls of the renal vein, aorta, inferior vena cava and/or a side branch of the aorta or vena cava. Still further alternative embodiments may be employed, including deployable or fixed annular rings supporting fiducials.

As the treatment plan will often have been developed before the fiducial implantation (although, as detailed herein, the treatment plan may be developed after fiducial implantation), tracking of the target tissue will be easier once the location of the fiducial relative to the planned target has been identified. A process for registration a treatment plan with implanted passive and/or active fiducials can be understood with reference to FIGS. 7, 10, and 11. As a starting point, a treatment plan 104 may have a known positional relationship 106 with planning image data 108 (these elements being shown schematically in FIG. 10). Relationship 106 can be established by inputting the desired lesion pattern relative to an image generated using the planning image data, as described above. So as to identify a location of fiducials 64 relative to the treatment plan 104, registration image data 110 may be acquired after fiducial implantation 70. Registration image data 110 will typically comprise three-dimensional image data encompassing both the renal artery tissue and at least some of the implanted fiducials, particularly the passive high-contrast fiducial marker structures. Identification of tissue surfaces and the like may again be facilitated by releasing contrast in the bloodstream. This facilitates segmenting the renal artery tissue surface and the heart/blood interface. The tissue/blood interface from registration image data 110 and planning image data 108 may be used to identify a relationship 112 between the plan image data set and the registration image dataset. The exemplary relationship 112 may comprise a mapping or transformation, ideally comprising a transformation matrix, offset, or the like. Rather than relying on the blood/tissue interface, alternative image/registration relationships 112 may be determined by identifying a series of discrete tissue landmarks. Note that the renovascular tissue may move significantly between acquisition of the planning image data set 108 and the acquisition of the registration dataset 110 relative to anatomical landmarks outside the renovascular system, and that the shape of the renal arteries may be deformed (even at similar phases of the beat cycle). Hence, while embodiments of the invention may employ a simple rigid transformation as the plan/registration image relationship 112, other embodiments may employ any of a variety of deformable registration techniques.

So as to facilitate identification of the plan/registration image relationship 112, registration image dataset 110 may be acquired using an image modality which is the same as that used to acquire planning image dataset 108. For example, where the planning image dataset comprises CT data, registration image dataset 110 may also comprise CT data. Alternatively, if MRI data has been used for the planning image dataset 108, MRI acquisition after fiducial implantation may be used for the registration image dataset 110. Similarly, if the planning image dataset 108 comprises ultrasound data, the registration image dataset 110 may also comprise ultrasound data. Nonetheless, other embodiments may employ a different image modality to acquire the registration image dataset than that used for acquisition of the planning image dataset. Any of a wide variety of three-dimensional image data fusion, three-dimensional rigid transformation, and/or three-dimensional deformable transformation techniques may be used despite the application of different imaging modalities.

Figure 9A:
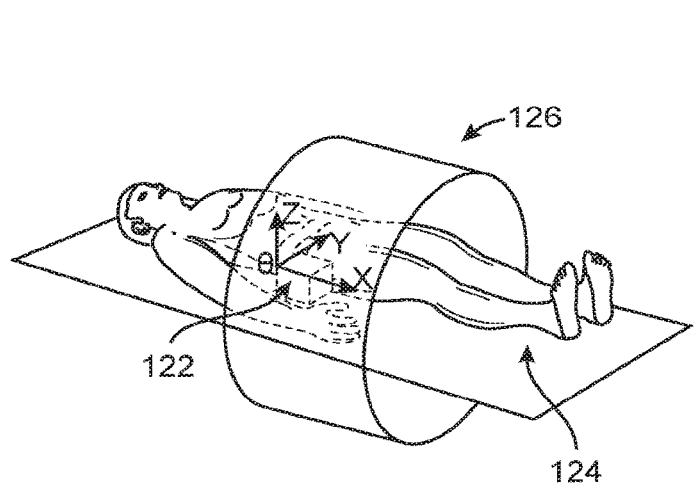
Figure 9B:
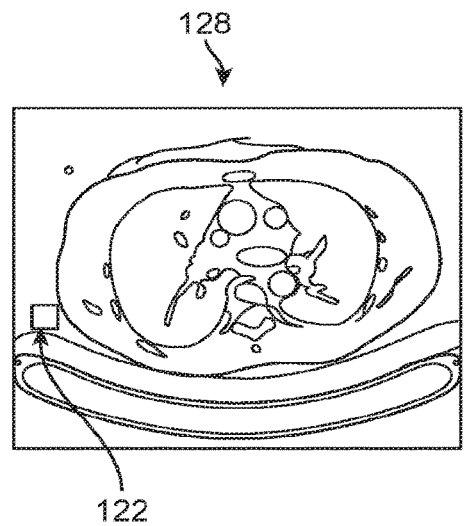
Figure 10:
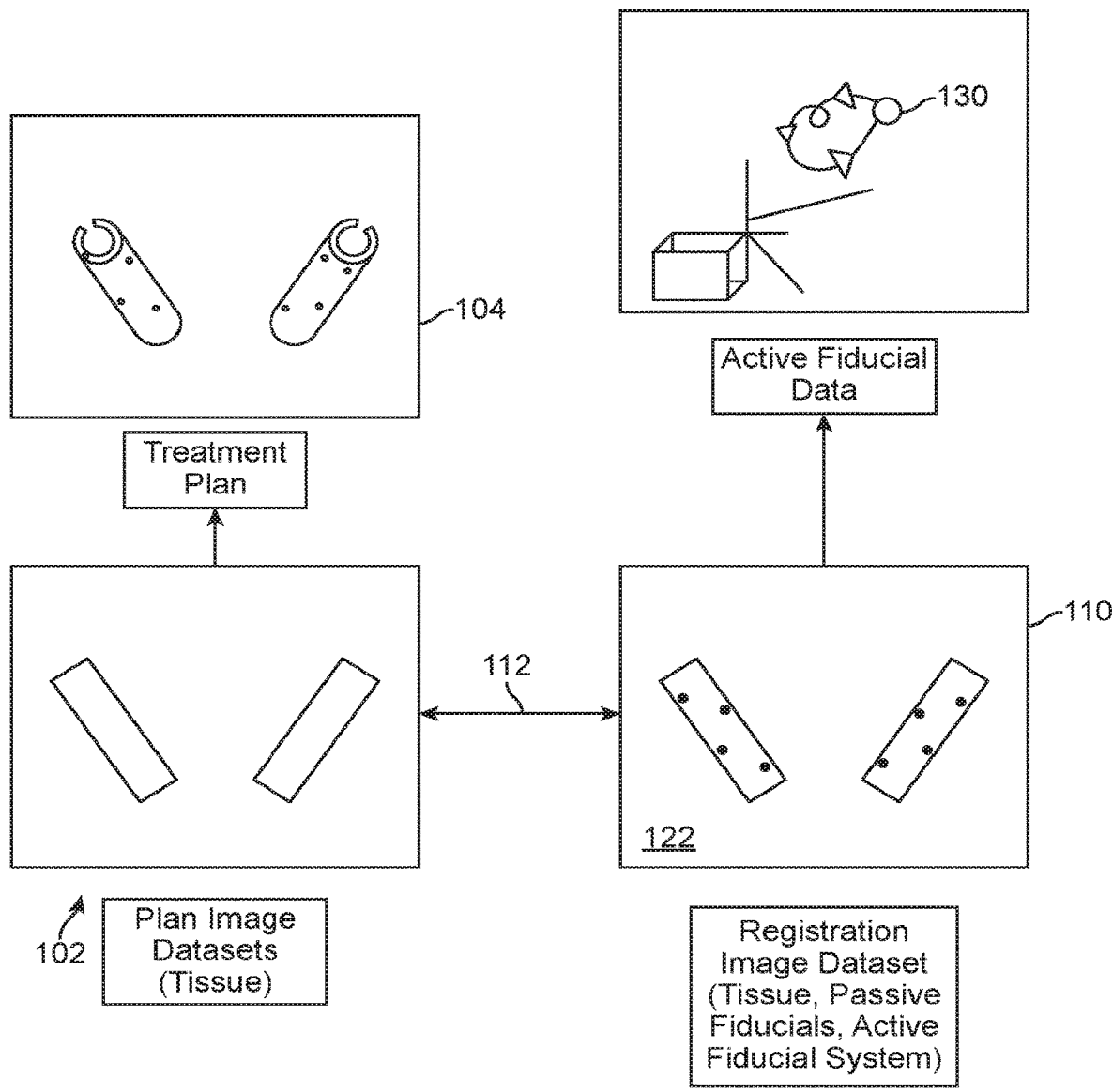
FIG. 10 schematically illustrates registration of implanted catheter-based active and/or passive fiducials with a treatment plan.
Figure 11:
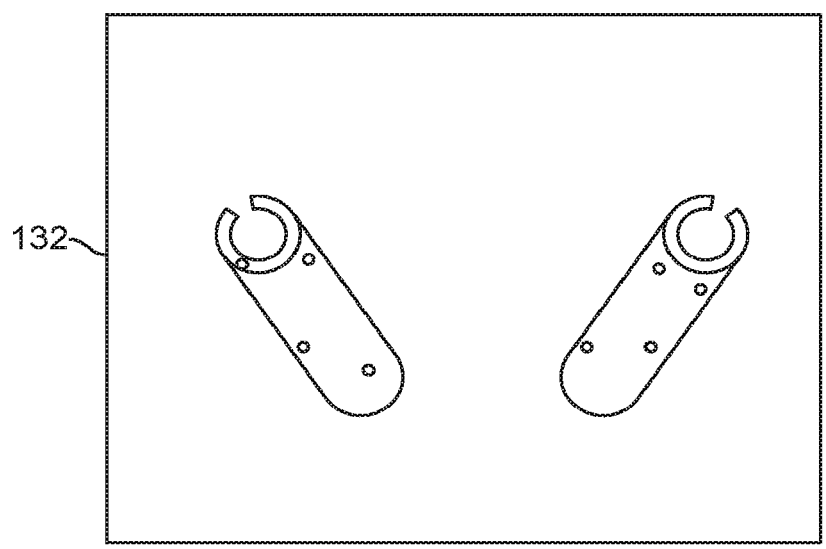
FIG. 11 graphically illustrates a registered treatment plan and passive fiducial system.

In exemplary embodiments, the registration image data 110 may include at least one component of an active fiducial system. For example, FIGS. 9A, 9B, and 10 illustrate a method and system for registering a catheter tip with a three-dimensional image dataset (such as CT data) with high absolute accuracy. Standard active catheter navigation systems may suffer from geometric distortion due to either magnetic field inhomogeneities or assumptions in electrical impedance. Analogous errors may be present in ultrasound or other navigation systems. While these tracking technologies provide good relative position measurements with respect to, for example, an image-able electrode in the coronary sinus, their absolute accuracy may not be as good as is desirable for radiosurgical treatments from outside the body.

FIGS. 9A and 9B schematically illustrate a transmitter 122 of an active fiducial catheter navigation system, with the exemplary transmitter shaped as a cube. The active fiducial may comprise a sensor disposed near the distal end of the catheter that senses the location of the position fiducial. The reference coordinate system of the active fiducial may be positioned at a corner of the cube-shaped transmitter 122. Alternative systems may replace this external transmitter with an external sensor, with the active fiducial comprising an associated transmitter. Regardless, the patient may lie on a patient support 124, and the patient support may also support the external active fiducial sensor 122 or transmitter. In some embodiments, the patient support 124 may comprise a vacuum bag or other structure so as to inhibit movement of the patient relative to the patient support, and the patient support may be movable (with the patient and the component of the navigation system mounted thereon).

The movable patient support 124, active fiducial transmitter 122, and patient are positioned for imaging, such as by being placed on a couch of a CT scanner 126. As a result, the registration image dataset (an image of which 128 is conceptually shown in FIG. 9B, the image being different with respect to the renovascular treatments detailed herein) contains the transmitter cube 122, such that the transmitter cube is visible in the CT dataset along with the patient's tissue and any other implanted fiducials.

In some embodiments, the patient support 124 and patient may be moved to a radiosurgery suite and placed on a platform, with the vacuum bag of the patient support 124 inhibiting movement of the patient relative to transmitter 122. A catheter having the active fiducial position sensor may be introduced into the patient and advanced to the desired location, allowing the active fiducial navigation system to determine position data from the active fiducial. As the position of the sensor 122 in the CT dataset is known, and location and orientation of the active fiducial navigation system is also known, and an active fiducial marker can be superimposed on the CT image dataset location identified by the navigation system of the active fiducial. Hence, a relationship between the active fiducial 130 and the tissue, passive fiducials, and treatment plan 104 may also be identified (see FIG. 10). By correlating the active fiducial position information with the phase of the heart, and by knowing a relationship of the target region to the active fiducial location throughout the heartbeat cycle (as can be determined from the time series of three-dimensional datasets in the planning image data), the active fiducial data signal may enhance tracking of the target region. This may be done for the blood pressure component and/or the displacement component of the cardiac cycle.

As a result of the registration step 102, the three-dimensional position offset (or transformation matrix or matrices) between the fiducials and the treatment plan may be determined, so that the fiducials are effectively registered with the treatment plan 132.

Figure 9C:
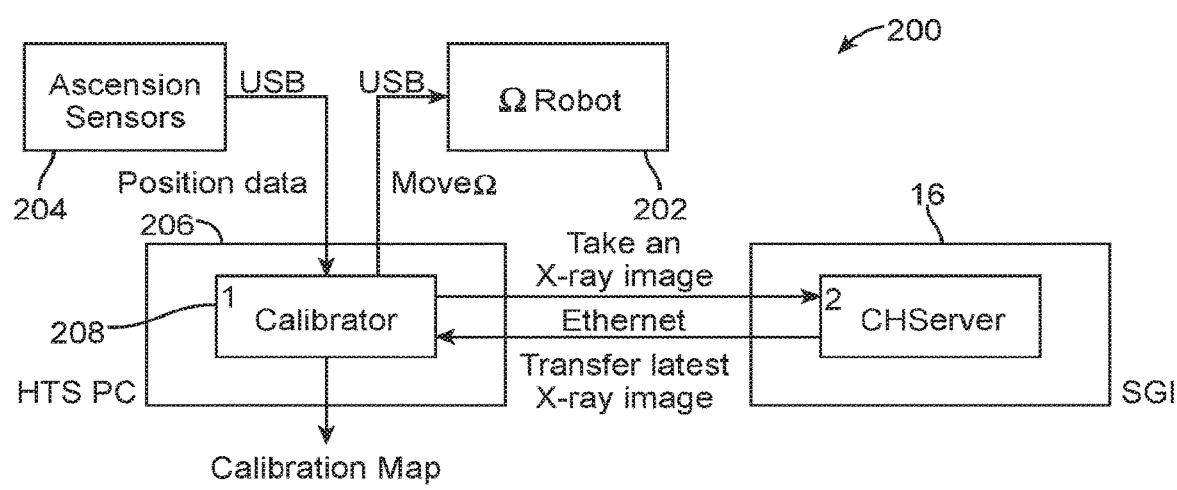
FIG. 9C is a functional block diagram schematically illustrating an exemplary active catheter calibration module.

Referring now to FIG. 9C, a block diagram of an exemplary calibration module 200 indicates an alternative system and approach for helping to register the patient tissue with a treatment plan, and/or for helping to align the patient with the radiosurgical treatment system. Calibration can, for example, be performed prior to delivering a treatment either before the patient is present on the patient support 24 or once the patient is on the patient support 24 of the radiosurgical system 10. Calibration can determine the mapping function, ϕ, between a coordinate system of an active fiducial system (such as a tracking coordinate system of an Ascension Technology Corp. 3D tracking system) and a coordinate system of radiosurgical system 10 (such as a CyberKnife™ radiosurgical robot coordinate system):

$$^{CK}p = \Phi(^{AS}p)$$

Eq. 1 where, $^{CK}p$ is a point in robot coordinate system and $^{AS}p$ is the same point in the active fiducial tracking coordinate system. The mapping function ϕ can be determined, for example, by moving an active fiducial (typically in the form of one or more position sensors) to a series of locations, ideally to a series of grid points inside a volume of interest. The grid points and/or volume of interest may be centered at or near an isocenter of the planned treatment and/or of the robot 14 supporting the linear accelerator 12 (or other radiation source). When using the exemplary CyberKnife radiosurgical treatment system, the treatment isocenter may be a point in the CyberKnife room where the axes of the two ceiling-mounted tracking cameras intersect. This may also be used as the origin of the CyberKnife coordinate system. The movement of the active fiducial between the locations or grid points may be performed using a motion platform Ω robot 202 (a separate robot manipulator for mechanically moving the active fiducials in an near the treatment site), and locations of the active fiducials may be sensed and recorded by the tracking module 206 based on both the active fiducial tracking system 204 and also the image tracking system 16 (such as the CyberKnife™ X-ray system). A least squares fit between the image tracking-based positions and the active fiducial-based positions can be used by the calibration module 206 to find the best-matching mapping function, ϕ.

A Calibrator 208 is a component of calibration module 206. Calibrator 208 will interact with a server application running on the radiosurgical system, called CHServer. CHServer will serve some requests from Calibrator 208, by communicating via an Ethernet. Calibrator 208 is also connected to the active fiducial motion platform, ΩRobot 202, and the active fiducial tracking system 204, both via USB. Calibrator 208 may:

Instruct the Ω ☐Robot to move the sensors to a specified location

Instruct the image tracking system 16 of the radio surgical system to acquire a pair of X-rays.

Capture active fiducial sensor coordinates for the present location

Download the X-rays via CHServer.

Repeat steps 1-4 until all grid points or otherwise desired locations have been visited. Once the data from all grid points have been captured, Calibrator 208 will compute the mapping function, φ, and store it in a file.

Figure 12:
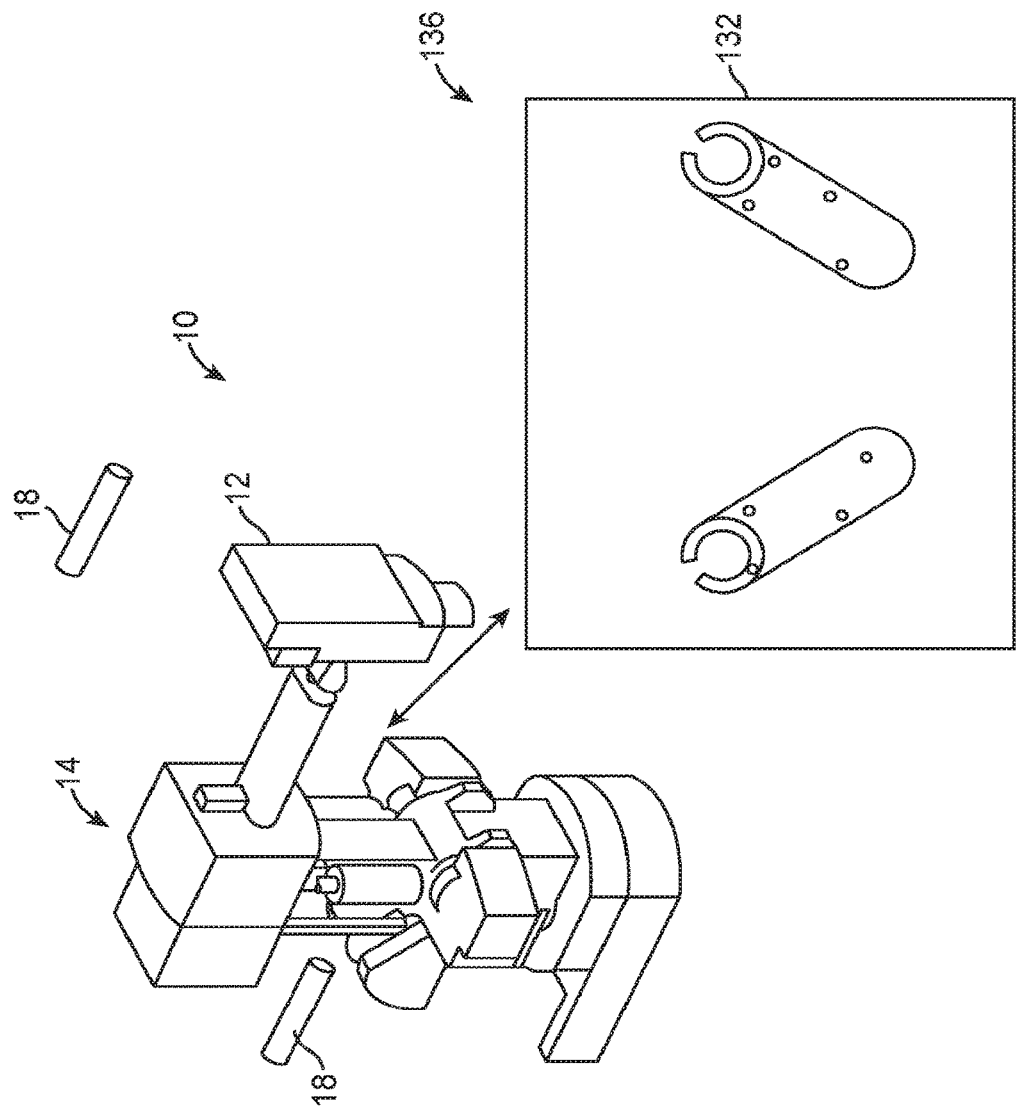
FIG. 12 graphically illustrates alignment of the treatment plan with the treatment system.

Referring now to FIGS. 7, 12, and 1, alignment 136 of the target regions of the tissue with the robot 14 will generally be performed by having the patient supported by patient support 24, and by moving the patient support using the articulated patient support system 26 so that the fiducials (as seen in the bi-plane X-ray images of image guidance system 16) are disposed at the desired location, such that the target regions of the treatment plan are aligned with the planned trajectories from linear accelerator 12. Hence, although the fiducials have in fact been implanted after the treatment plan was completed, the alignment process may proceed with reference to superimposed fiducial locations on the planning treatment data, with the alignment process, as it appears to the medical personnel performing the radiosurgical treatment, being quite similar to that applied when a pre-planning fiducial is used.

Figure 13:
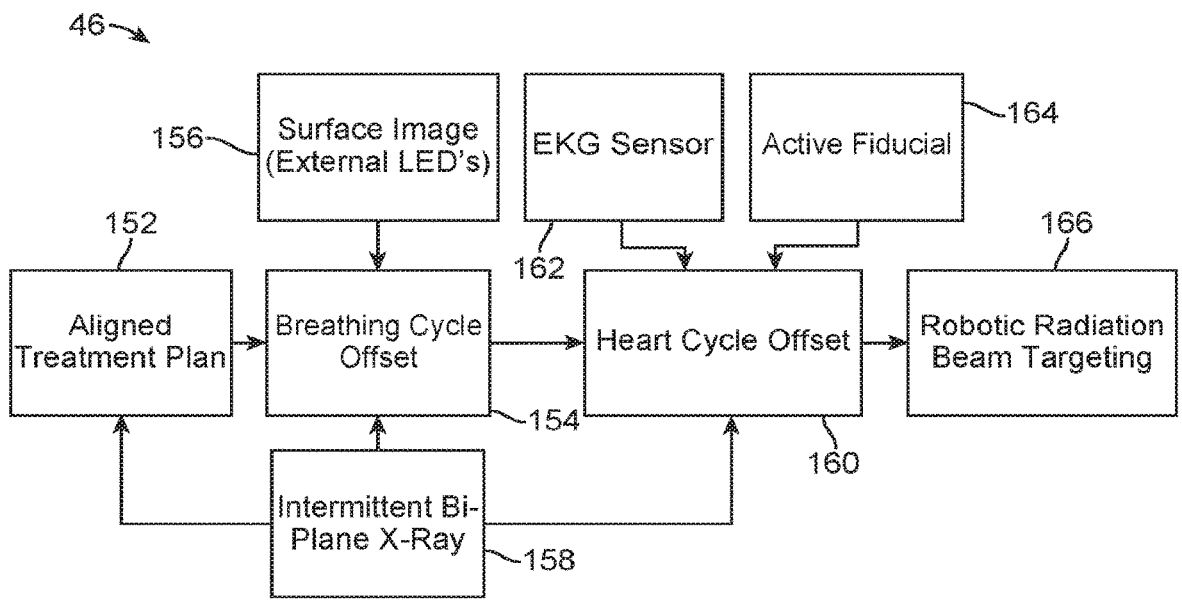
FIG. 13 schematically illustrates a method for treating a target region according to a treatment plan.

Referring now to FIGS. 7 and 13, the treatment 46 and tracking of the target tissues by the robot and linear accelerator can be generally understood. The aligned treatment plan 152 (including the planned trajectories and the superimposed fiducials, once they have been appropriately aligned with the robot 14 as described above with reference to FIG. 12) defines appropriate trajectories and beams of radiation from linear accelerator 12. As with known radiosurgical treatments, an offset is determined to compensate for the breathing cycle 154, with the breathing offset generally being determined from the respiration amplitude as identified using surface images of the patient, and specifically from external LEDs mounted on the patient's skin 156. Intermittent bi-plane X-ray data 158 can be used to revise and correct the breathing motion offset for any patient movement or the like.

A heart cycle offset 160 may also be applied to the treatment plan 152, with the phase of the heart cycle offset being identified by an EKG sensor 162 or other heart cycle monitor coupled to the patient. The heart cycle may be used to determine a renal artery movement cycle, due to the blood pressure component and/or the displacement component of the cardiac cycle. That is, the beating of the heart will result in a corresponding movement of the renal artery, such as due to an expansion of the outer diameter of the renal artery resulting from the increased pressure of the blood within the renal artery, and/or displacement of the entire renal artery. The heart cycle can be temporally correlated with the renal artery movement cycle or used as a direct proxy for the renal artery cycle. For example, movement of the renal artery may temporally lag behind a heartbeat indicator on which the treatment relies (movement due to the blood pressure component of the cardiac cycle may lag the displacement component of the cardiac cycle, or visa-versa, and one or both may lag the heartbeat indicator). This temporal lag may be exact or estimated, and factored into the heart cycle offset 160. Alternatively, in other embodiments, the heart cycle may be used without factoring in such a temporal lag. That is, the heart cycle may be used to directly determine the time of movement of a renal artery. Data or signals from the active fiducial 164 may also be used to identify the phase of renal artery motion, as well as providing an appropriate renal artery motion offset. The renal artery motion offset may, as explained above, be identified from the time series of three-dimensional datasets included in the treatment plan 152. Alternatively, the EKG sensor signals 162 and/or active fiducial signals 164 may be used for gating of the radiation beams, such that the radiation beams are only directed toward the renovascular tissue at portions of the renal artery motion cycle during which the target regions are sufficiently aligned with the plan 152. Note that some portion of the movement of the renovascular tissue located at the target regions may be disregarded, for example, with internal deformation of the tissue between the fiducials and the target regions being disregarded in favor of a fixed offset, with motions in one or more orientations having a sufficiently limited amplitude being disregarded, or the like. Regardless, once the appropriate offsets have been applied to the treatment plan, the robotic radiation beam targeting 166 can then be applied.

Figure 12A:
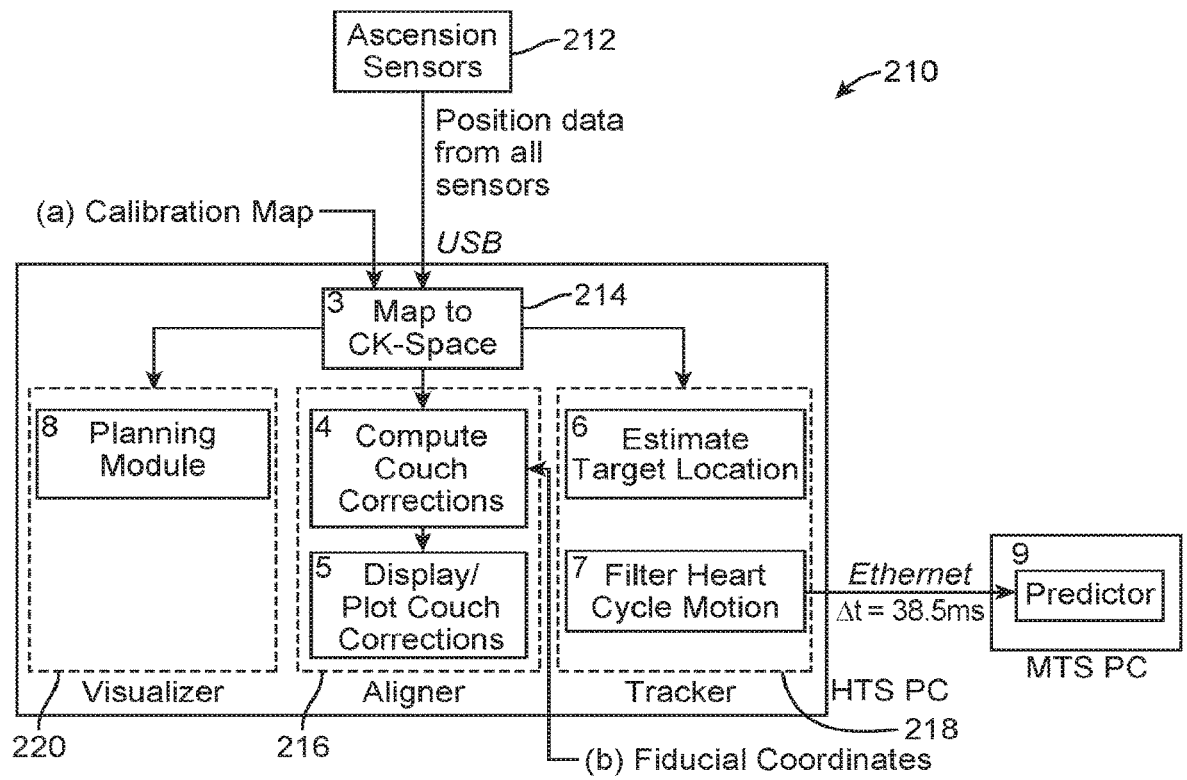
FIG. 12A is a functional block diagram schematically illustrating an embodiment of an active catheter tracking module.

Referring now to FIG. 12A, a tracking module 210 using components and techniques related to those of FIG. 9C can now be understood. For convenience, we can here assume that the alignment center in the planning CT data is disposed at a center of gravity of the fiducials. As this will often not be the case, offsets between the planning data and fiducial centers will typically be included. Tracking module 210 includes software run on a renovascular tracking computer RVTS during treatment delivery. The alignment module 206 may similarly run on the renovascular tracking computer RVTS, with the tracking module and alignment module comprising code running on a personal computer (PC) in the exemplary embodiment. The tracking module 210 receives as input the position data 212 from all the active fiducial sensors (such as the Ascension sensors) of the implanted catheter system via USB. Tracking module 210 applies the calibration map 214, φ, to this active fiducial data to compute the active fiducial locations in the coordinate system of the radiosurgical system (such as in CyberKnife™ coordinates). From this, the position data flows into 3 different paths: an Aligner 216, a Tracker 218, and a Visualizer 220.

Aligner 216 makes use of the data from the active fiducials to alter alignment of the patient with the radiosurgical system. More specifically, the active fiducial sensor data can be matched in aligner module block [4] to the fiducial coordinates from the planning CT data (specified in radiosurcial system coordinates) to determine the couch corrections. The average couch correction over a specified period can be computed and displayed to the user. The user can then apply these couch corrections and observe how couch corrections change in real-time. The block [5] may display the couch corrections to the user in a graphical form, computed as running averages.

Tracker 218 may include a tracker module block [6] configured to compute the target location from the incoming active fiducial locations. After alignment the alignment center of the patient, as defined in the planning CT coordinate system, coincides with the iso-center of the radiosurgical treatment system. If there is no motion, the output of block [6] might be (0, 0, 0). If there is motion, the output of block [6] might be the change in position from the initial or ideal position. A tracker module block [7] may remove the renovascular tissue motion from the target motion. The resulting 'respiration only' change-from-ideal motion waveform can be sent to a position predictor of the radiosurgical treatment system processor, which can apply this information per a standard data path to drive the robot.

The active fiducial data may be provided to visualizer 220, which may display the fiducial locations superimposed on CT data, optionally using display module components of the planning module. This may allow the system user to visualize the locations of the active fiducials after they have been implanted, and the like. In addition, the visualizer may display the treatment beams fired by the robot in real time using the position data measured using the active position sensor.

As can be understood from the above, patient movement may complicate radiation treatment of the renovascular system. If patient movement is not tracked, targeting can direct the beams into a time average location of the target. If a surrogate and target are rigidly coupled together and tracking of the surrogate is accurately maintained, targeting is not compromised. However, when the surrogate is offset from the target and the tissue in which the target and surrogate are disposed deform, and if the deformation between the surrogate and target are not tracked, a single imaging phase can be used to calculate the relative location of the surrogate and target. Selection of the appropriate imaging phase (from among the time series of phases at which three-dimensional imaging is acquired) can affect the accuracy of targeting. For example, if a calculation of the relative locations is performed for a phase where the surrogate to target offset is not close to the average offset throughout the heartbeat cycle, targeting based on an average surrogate location may result in dose delivery being offset from the target.

One relatively simple approach to accommodate untracked motion is to use an integration of the target volume so that the target is expanded to include the target region location throughout all phases of the target region motion (including throughout a heartbeat cycle and/or respiration cycle). Such an integrated target can ensure treatment of the target region but may increase the total treatment volume receiving relatively high doses of radiation. Alternative pursuit tracking approaches (similar to those used in the Accuray Synchrony™ tracking system) where the radiation beams move synchronously with the target tissue can be used in order to deliver dose to the target region. These existing approaches may not consider motion of radiation sensitive collateral tissues, nor motion of the surrogate relative to the target region. Gating of the radiation beam to untracked motion can also be employed, but may increase the total time to provide a sufficient dose to the target region.

In an exemplary alternative untracked treatment approach, the tissue may be analyzed as being subjected to the dose that is integrated across an untracked tissue motion. The peak dose may be delivered to the average position with some alteration of the dose distribution in areas where the dose gradient is changing in the direction of motion. For motions which are relatively small relative to the rate of change of the dose gradient, the dose distribution may only be slightly altered by the untracked motion. The more significant change between the intended dose and that actually applied to tissue may be imposed by any shift of the peak dose from its planned anatomical locations.

In this exemplary targeting approach in the presence of untracked motion, imaging of the tracking surrogate may be used to direct the radiation beams. If only a single image of the tracking surrogate is obtained there will be targeting errors resulting from the untracked motion, so that intermittent acquisition of images allow the location data to be combined so as to determine future beam directions, potentially by averaging so as to better locate the tracking surrogate. This approach may result in the beams being directed relative to the average location of the tracking surrogate relative to the target region. If the plan has been created based on this same average relative positioning, the peak dose location should correspond to the planned target region.

In light of the above, and as can be understood with reference to FIGS. 14A-14E, targeting accuracy can be enhanced in the presence of untracked motion by analysis of a time average location of the target relative to the tracking surrogate throughout renovascular and/or respiratory motion. One relatively simple method is to use this time average relative location during planning by selecting the phase where the tracking surrogate is nearest to its average relative location. Note that the precise location of the surrogate may not be known during planning, but the target structure adjacent or in the renovascular system corresponding to the target locations for fiducial implantation may be identified, so that the surrogate may be targeted for deployment at or near a location appropriate for the planned average offset. The planning phase can be chosen based on the average location of the target surrogate location relative to the target structure location.

Note that no discrete phase, as selected from the time series of three-dimensional planning datasets, may correspond exactly to the time average location. Some targeting error may remain because of this difference. Additionally, the average location of the tracking surrogate may not correspond to the average configuration of the target relative to the tracking surrogate. A somewhat more accurate solution may be to consider the time average relationship between the surrogate and the target. As shown in FIGS. 14A-D, this time average may not correspond to any particular phase in the captured time series. Nonetheless, it may be convenient and beneficial to select the closest phase to the calculated time average.

Addressing FIGS. 14A-D an example of two-dimensional relative motion between a tracking surrogate (represented by the filled circle) and the target (represented by the open circle). FIGS. 14A-D show the location of the target and circuit relative to a reference frame in four phases of cyclical renovascular tissue motion. Both the surrogate and the target move relative to the reference frame, but the target also moves relative to the surrogate.

Figure 14A:
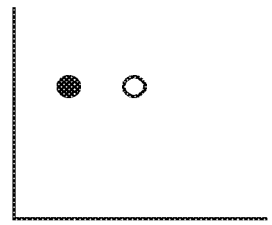
FIGS. 14A-14E schematically illustrate relative motion between a tracking surrogate and a target tissue as may be caused by tissue deformation, along with a calculated average target center.
Figure 14B:
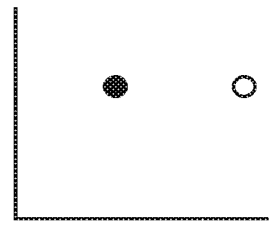
Figure 14C:
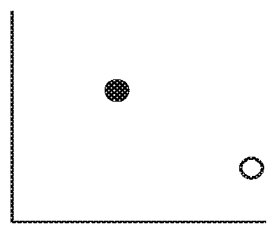
Figure 14D:
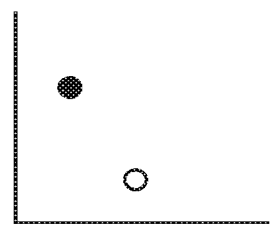
Figure 14E:
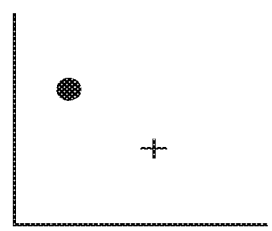

In FIG. 14E, a calculated average target center may provide accuracy advantages. The relationship between the average target center and the tracking surrogate does not necessarily match any of the discrete images of FIGS. 14A-D, but instead the configuration corresponds to an average separation between the objects.

In many radiosurgical systems, a CT volume set is used to create digitally reconstructed radiographs (DRRs). During treatment, guidance images are matched to these DRRs in order to align the patient. A DRR can conveniently be constructed from any one of the datasets for a particular phase of the time series. Hence, the target itself may be somewhat difficult to identify in the DRR, which provides motivation for use of a tracking surrogate. The offsets used to target the beams can, nonetheless, be based on the average target location of a DRR generated from a selected phase which most nearly matches the time average relationship. Alternatively, the relative location of the target and offset may use a calculated time average without relying on the DRR, so that the target location of the target in the CT volume may not correspond to a particular DRR. For example, if you have fiducial coordinates f (k,t), then the distances linking the fiducials are: $d(k,m,t)=|f(k,t)-f(m-t)|$. There will be $$M = \frac{N}{2}(N-1)$$

such link distances between fiducials, where N is the number of fiducials. The link distances can be represented as: {d(k,m,t)}, which is a M dimensional vector. Then the time average distances can be computed as:

$$\{d(k, m)\}.$$

Then compute the vector distance:

$$\Delta(t) = \sqrt{\sum_{\forall \frac{N}{2}(N-1) values} (d(k, m, t) - d(k, m))^2}.$$

Then pick the phase corresponding to the smallest Δ(t)

Figure 15:
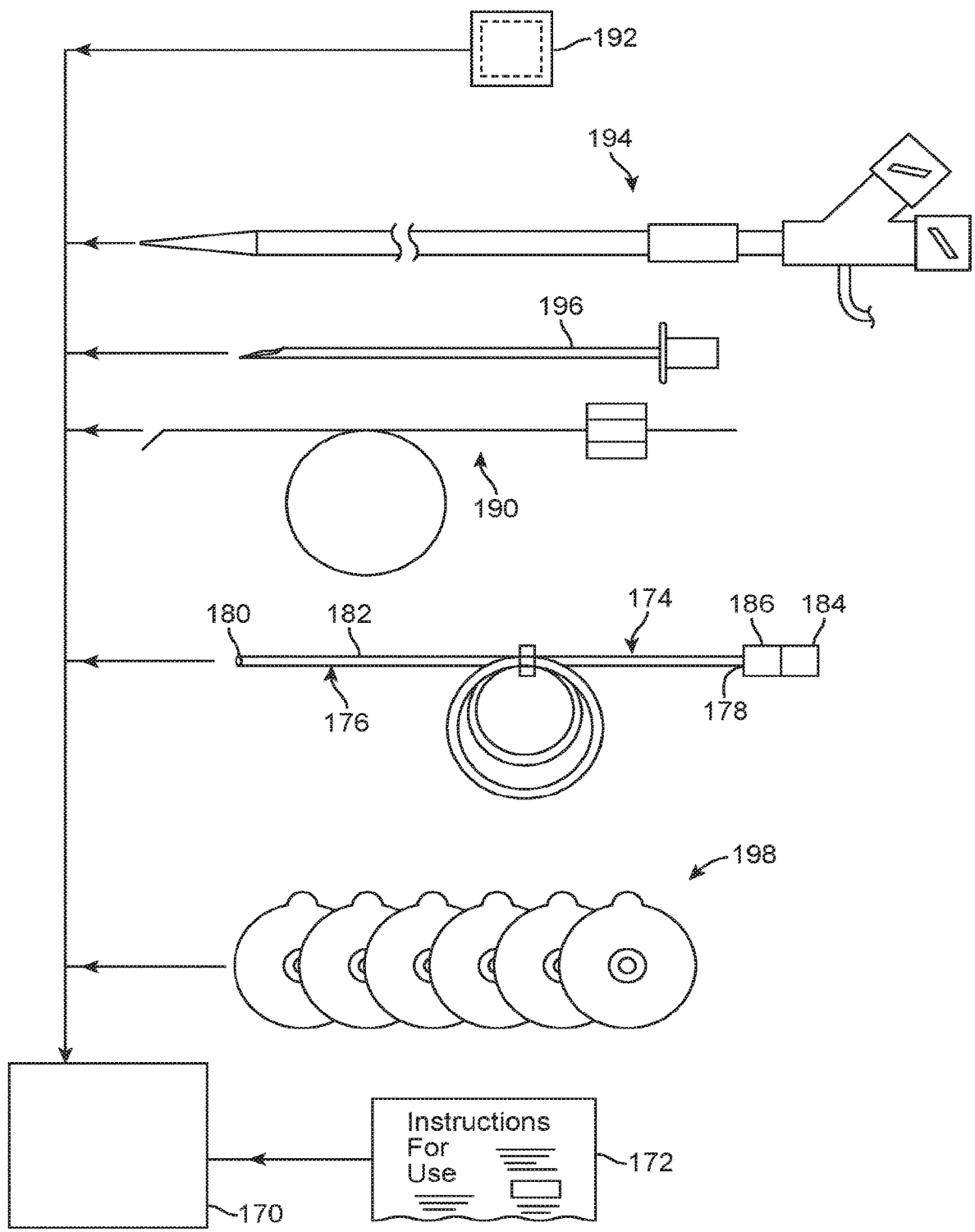
FIG. 15 schematically illustrates a kit for use with the systems and methods described herein for treatment of non-tumerous diseases of the heart.

Referring now to FIG. 15, a kit of components will facilitate radiosurgical treatments using the systems and methods described herein. These and/or other components may be included in one or more hermetically sealed packages 170, along with instructions for use 172 of the enclosed components and/or the system in general. An exemplary embodiment of the kit will include some or all disposable items used during insertion of a percutaneous catheter into a recipient to treat hypertension as detailed herein. The catheter 174 will generally have an elongate flexible body 176 extending between a proximal end 178 and a distal end 180. A sheath 182 may have a lumen receiving the catheter body 176, the sheath optionally restraining fiducials in a small profile configuration suitable for insertion and positioning, and the sheath optionally also enclosing a helical or radially expandable fixation structure as described above. Proximal hubs 184, 186 of the sheath and catheter may allow the sheath to be withdrawn proximally from over the catheter body 176, optionally using a rapid exchange approach. Similarly, the catheter may have a rapid exchange guidewire lumen for receiving a guidewire 190, or may have a through lumen for using the catheter in an over-the-wire approach. Furthermore, the catheter may have a flow-directed balloon at the distal end, which will facilitate rapid deployment of the catheter downstream into a target site. While the catheter may be inserted prior to the planning image acquisition and throughout the radiation treatment, the catheter will typically be deployed on a treatment day after image acquisition and treatment planning is complete.

As described above, the catheter can include passive fiducials which include high-contrast markers that can be readily visualized during radiosurgical treatments so as to provide a passive surrogate. Alternatively, catheter 174 may include an active fiducial which transmits or receives signals electronically, ultrasonically, electromagnetically, radioactively, or the like so as to indicate a position of the catheter (and via a known relationship between a position of the catheter and the target region, thereby indicating a position of the target). Passive fiducials may comprise, for example, small metallic structures comprising gold, platinum, iridium, and/or tantallum, or the like. The catheter may also include sensors for measuring the dose received during treatment, blood pressure, and other biometric signals.

Reviewing some exemplary components included within one or more sterile packages 170, the kit may include an iodine or other skin cleansing lotion 192, a vial of 1% xylocaine, or the like. These materials may be used to create an anesthetic skin wheal at the site of skin puncture. An introducer sheath 194 may include at least one or possibly two side ports so as to allow for blood withdrawal, infusion of multiple simultaneous drugs, and other intravenous maintenance solution transmission. Exemplary introducer sheath 194 has two ports or channels so as to allow two catheters to be positioned simultaneously. A rubber diaphragm may be found at the entrance of each port, with an exemplary introducer having a 3 mm cotton tubular cuff that is impregnated with a compound comprising silver can be advanced to the site of skin puncture along a sheath of the introducer for use as a bacteriostatic.

A needle 196 allows, when used in combination with guidewire 190 and sheath 194, venous cannulation and secure positioning of catheter 174. A set of EKG electrodes 198 allows for tracking of cardiac rhythms, while a set of LEDs or gold fiducials (or fiducials of an alternatively acceptable material) may be mounted to the chest wall for monitoring respiration. A conductor may extend along catheter body 176 so as to couple a helical fixation lead or other conductive distal structure to engage the renovascular tissue with a proximal connector of proximal hub 186. This may allow the fixation lead or other conductive structure at the distal end of the catheter to be used as a heart signal electrode for monitoring the heartbeat, alone or in addition to the other EKG electrodes. The kit package 170 may also include a patient mattress, which may be a mattress configured to limit changes in patient position such as a vacuum bag mattress, with the vacuum bag optionally having a vacuum port and/or containing discrete pellets so as to reconfiguring and affixing of a shape of the bag once the patient has been comfortably positioned on the patient support.

In use or during deployment of the catheter-based fiducial system, needle 196 (such as a 20-gauge locator needle) may be used to identify an internal jugular vein, subclavian or brachial vein, or other vein as necessary. Alternatively, and artery may be identified. A 14-gauge needle (not shown) also to be included in the kit and within package 170 may then be inserted and wire 190 placed through the inserted needle, with the needle then being withdrawn. The skin may be incised with a roughly 2 mm incision at the wire insertion site, and a dilator used (optionally at the distal end of insertion sheath 194) to enlarge the tissue track. A distal end 180 of catheter 174 may then be inserted over the needle, with the position of the distal end of the catheter being checked using X-ray or fluoroscopic guidance. The fixation structure near the distal end 180 of catheter 174 may be exposed by proximally withdrawing sheath 182 from over catheter body 176, and the distal end affixed to a target tissue of the renovascular system. Proximal hub 186 of catheter 174 may then be sutured or otherwise affixed to the skin of the patient.

Figure 8F:
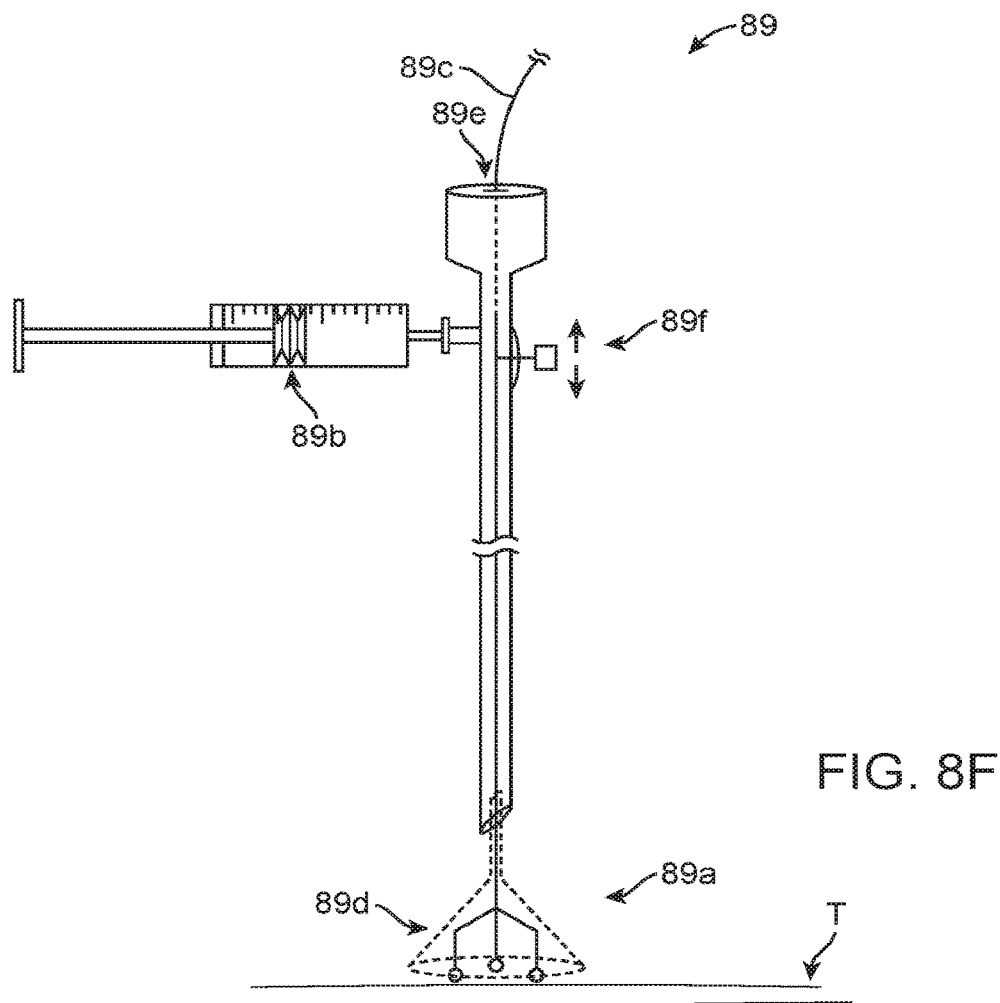

Using fluoroscopic or ultrasound guidance, an alternative affixation approach may comprise deployment of a polyethylene cone from a small profile configuration to a large profile configuration at distal end 180 of catheter 184, as described above regarding FIG. 8F. The cone may be deployed by sliding a switch on the side of the proximal portion of the catheter. A vacuum may be applied to an open end of the cone, optionally using a 10 or 20 cc syringe or the like. A stopcock may be closed to maintain the vacuum, and the syringe removed. In some embodiments, the cone may be affixed via suction to an appropriate surface.

Optionally, a detecting, pacing, or ablating electrode can be placed through a port of catheter hub 186 or through introducer sheath 194. If an active fiducial or surrogate is used, communication between the navigation system and robotic control system may be confirmed.

Some or all embodiments detailed herein and variations thereof may be practiced to achieve resolution of fluid overload with respect to conjunctive heart failure by induction or enhancement of diuresis, reduction of remodeling after a myocardial infarct and slowing of the progression of chronic renal disease to dialysis. Some or all of the therapeutic effects detailed herein may be a result of one or more of the reduction of the systemic sympathetic tone causing vasoconstriction of blood vessels, reduction of the load on the heart and/or the direct effects of denervation on the kidney(s).

Experiments

An animal experiment was conducted to record the motion of the renal artery as a target for radiosurgery in order to affect the sympathetic nerve and reduce hypertension. For this experiment, an expanding helical structure with three fiducials was placed in the inferior vena cava of a pig model through a femoral vein sheath, with the expanding structure similar to that shown in FIGS. 6C and 6D, and modified from a vascular filter structure developed by Crux Biomedical Inc of California. Separately, gold beads were surgically attached to the right renal artery and to a location near the left renal artery. Three cardiac gated CT's were acquired with these fiducials implanted: at exhale; at inhale; and at exhale where the blood pressure had been increased medically. An analysis of the CT data was made based on these experiments.

The five targets (two surgical fiducials and three fiducials on the Crux device) showed very little cardiac motion. The amplitude of cardiac motion of all of the fiducials was less than 0.5 mm. This amount of motion may optionally be treated as negligible during radiosurgical treatment—including for high-blood pressure conditions.

Comparing the locations measured for inhale and exhale showed movements of 5-7 mm with respiration. This motion may be compensated for (for example, using the Synchrony™ tracking system of the Cyberknife™ radiosurgical treatment system) for desired accuracy in radiosurgical treatment. The use of spine alignment may be an alternative but may involve margins of 3-7 mm to achieve a therapeutic result, and such margins will often be larger than is ideal.

The respiratory motion of the Crux fiducials were very similar to the motion of the sutured fiducials. The relative motion between the right renal artery fiducial and the average of the Crux fiducials was 1.6 mm. The relative motion between the left fiducial and the average of the Crux fiducials was much less −0.2 mm. A margin of 2 mm may be considered if a Crux device were used for targeting. This margin is likely manageable.

Figure 16B:
FIGS. 16A and 16B illustrate 3D renderings of an exemplary position surrogate disposed within the inferior vena cava of a system, and also shows gold bead fiducials disposed on the right renal artery and near the left renal artery.
Figure 16A:
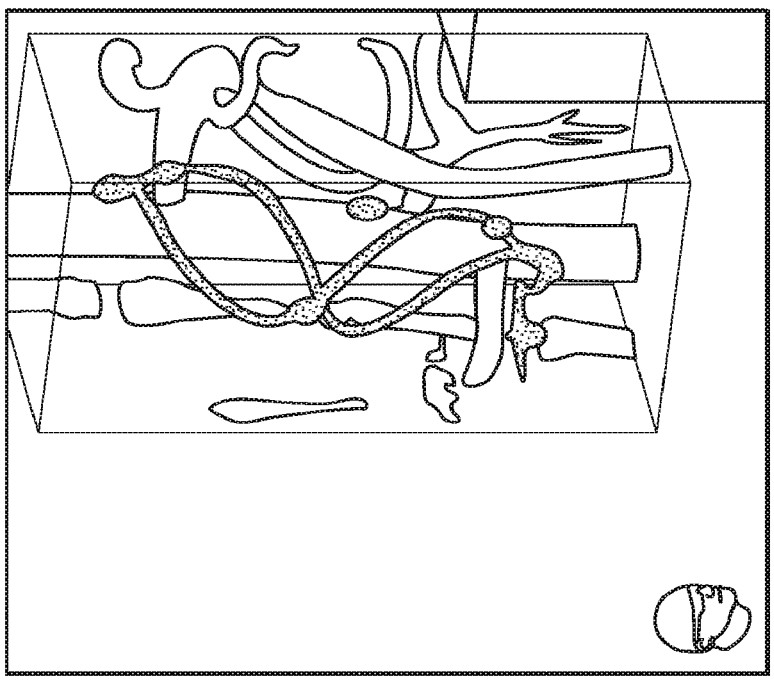

As shown in FIGS. 16A and 16B, the Crux fiducials were in close proximity to the surgically placed fiducials. The right surgically placed fiducial was placed on the right renal artery but surgical placement of the left fiducial very near the left renal artery was more challenging, so that the left surgically placed fiducial was separated somewhat from the left renal artery as shown.

The positions of the central Crux fiducial for ten cardiac phases (5%, 15%, 25%, . . . 95%) at inhale are shown in Table 1. More specifically, Table 1 provides the measured fiducial center of gravity, showing the largest amount of cardiac motion (which was the central Crux fiducial measured at inhale). These distances are expressed in mm using CT coordinates.

This measurement showed more motion than any of the other fiducials and any of the other CT sets. Although the variation in location appears to be measureable, it is clearly negligible for radiosurgery.

TABLE 1

| Fiducial center of gravity: (phase, x, y, z) | |
|---|---|
| 0 | −0.334879 33.0463 −448.703 |
| 1 | −0.332905 33.0451 −448.706 |
| 2 | −0.247289 33.0463 −449.25 |
| 3 | −0.249885 32.9588 −448.707 |
| 4 | −0.202549 33.0023 −448.586 |
| 5 | −0.287425 33.0036 −448.661 |
| 6 | −0.247289 33.0458 −448.91 |
| 7 | −0.250808 33.046 −448.919 |
| 8 | −0.292489 33.0015 −448.753 |
| 9 | −0.292446 33.0012 −448.752 |
| Mean center of gravity: | −0.273796 33.0197 −448.795 |

The positions of each of the fiducials in phase 0 (5% R-R) were compared between the inhale and exhale CT sets. Table 2 shows respiratory motion of each fiducial (top) and the relative motion between the sutured fiducials and the Crux fiducials (bottom). All distances are presented in mm using standard CT coordinates. As shown in Table 2, respiratory motion of 5-7 mm was measured for all of the fiducials.

TABLE 1

| Motion (Exhale–Inhale) | | | | |
|---|---|---|---|---|
| Fiducial | CT X | CT Y | CT Z | Mag(mm) |
| Rt. Renal Artery | 0.6487 | 0.5921 | 4.787 | 4.866905 |
| Lt. Renal Artery | −0.577 | 0.811 | 6.322 | 6.39987 |
| Superior Crux | −0.3042 | 0.805 | 7.051 | 7.103321 |
| Center Crux | −0.029 | 0.352 | 6.12 | 6.130183 |
| Inferior Crux | −0.2 | 1.959 | 5.008 | 5.38124 |
| Rt. Renal-mean(crux) | | | | |
| 0.826 | −0.446 | −1.272 | 1.582 | |
| Left Renal-mean(crux) | | | | |
| −0.399 | −0.227 | 0.262 | 0.529 | |

The motion of each of the surgically placed fiducials was compared to the average of the Crux device fiducial motions. The Crux device positions were averaged because it may be desirable, when using commercially available systems such as the CyberKnife™ radiosurgical system, to use multiple Crux fiducial implants and/or multiple fiducials on a single Crux implant, and because the CyberKnife and other systems may track the center of mass of all fiducials that the system locates. The magnitude of the difference in motion was 1.6 mm. This relative motion may degrade the targeting accuracy slightly if the Crux were used for targeting, so that 1.6 mm could be added to the margins (of either the target contours or the critical structure contours) in order to use the Crux device as a fiducial and provide the therapeutic result that is desired.

Based on the motion measurements made in the abdomen, radiosurgical treatment of the renal artery may use tracking to compensate for respiratory motion, without tracking of heartbeat-induced motion of the renal arteries. A temporary fiducial in the inferior vena cava will be sufficient for targeting the nerves near the renal arteries.

While the exemplary embodiments have been described in some detail for clarity of understanding and by way of example, a number of changes, modifications, and adaptations may be obvious to those of skill in the art. Hence, the scope of the present invention is limited solely by the appended claims.

What is claimed is:

1. A radiosurgical method for treating a patient body having a renovascular system, the patient having hypertension, the method comprising:
   receiving a desired lesion pattern and planned radiation distribution;
   determining an estimated lesion of the renovascular system based on the planned radiation;
   displaying a graphical representation of the estimated lesion;
   simulating effects of gross misalignment between the patient and a radiosurgery treatment system; and
   outputting tracking errors on the estimated lesion location and shape prior to remodeling by the radiosurgery treatment system of a target portion of the renovascular system based on the estimated lesion.

2. The radiosurgical method of claim 1, wherein the desired lesion pattern comprises a desired lesion of renal nerves in the renovascular system for treatment.

3. The radiosurgical method of claim 1, wherein the desired lesion pattern is received from a user interface of a treatment planning module.

4. The radiosurgical method of claim 1, wherein the estimated lesion comprises an estimate of renovascular tissue that receives a sufficient dose of radiation for therapeutic remodeling.

5. The radiosurgical method of claim 1, wherein the graphical representation of the estimated lesion indicates an eventual tissue state of the renovascular tissue.

6. The radiosurgical method of claim 1, further comprising displaying a graphical representation of a three-dimensional radiation dose pattern.

7. The radiosurgical method of claim 6, wherein the three dimensional radiation does pattern comprises one or more portions that indicate tissue subjected to differing levels of radiation.

8. The radiosurgical method of claim 1, wherein the graphical representation of the estimated legion comprises one or more two-dimensional planar sections through the renovascular system of the patient body.

9. The radiosurgical method of claim 8, wherein the one or more two-dimensional planar sections each comprise at least one isodose line corresponding to an absorbed dose of radiation.

10. The radiosurgical method of claim 1, further comprising:
    obtaining planning image data of the renovascular system of the patient body; and
    remodeling a target portion of the renovascular system of the patient body based on the estimated lesion.

11. A treatment system for treating a patient body having a renovascular system including a first renal artery and a second renal artery, the patient having hypertension, the treatment system including at least one computing device, the computing device configured to:
    receive a desired lesion pattern and planned radiation distribution;
    determine an estimated lesion of the renovascular system based on planned radiation;
    display a graphical representation of the estimated lesion;
    simulate effects of gross misalignment between the patient and a radiosurgery treatment system; and
    output tracking errors on the estimated lesion location and shape prior to remodeling by the radiosurgery treatment system of a target portion of the renovascular system based on the estimated lesion.

12. The treatment system of claim 11, wherein the desired lesion pattern comprises a desired lesion of renal nerves in the renovascular system for treatment.

13. The treatment system of claim 11, wherein the desired lesion pattern is received from a user interface of a treatment planning module.

14. The treatment system of claim 11, wherein the estimated lesion comprises an estimate of renovascular tissue that receives a sufficient dose of radiation for therapeutic remodeling.

15. The treatment system of claim 11, wherein the graphical representation of the estimated lesion indicates an eventual tissue state of the renovascular tissue.

16. The treatment system of claim 11, wherein the computing device is further configured to display a graphical representation of a three-dimensional radiation dose pattern.

17. The treatment system of claim 16, wherein the three dimensional radiation does pattern comprises one or more portions that indicate tissue subjected to differing levels of radiation.

18. The treatment system of claim 11, wherein the graphical representation of the estimated legion comprises one or more two-dimensional planar sections through the renovascular system of the patient body.

19. The treatment system of claim 18, wherein the one or more two-dimensional planar sections each comprise at least one isodose line corresponding to an absorbed dose of radiation.

20. The treatment system of claim 11, wherein the computing device is further configured to:
    obtain planning image data of the renovascular system of the patient body.

* * * * *